(12) United States Patent
Belfield et al.

(10) Patent No.: US 6,716,601 B1
(45) Date of Patent: Apr. 6, 2004

(54) COMPOSITIONS AND METHODS UTILIZING THE YEAST ZE01 PROMOTER

(75) Inventors: Graham P Belfield, Loughborough (GB); Caroline Oakley, Loughborough (GB)

(73) Assignee: AstraZeneca AB, Soderalje (SE)

( * ) Notice: Subject to any disclaimer, the term of this patent is extended or adjusted under 35 U.S.C. 154(b) by 0 days.

(21) Appl. No.: 09/743,194

(22) PCT Filed: Nov. 17, 2000

(86) PCT No.: PCT/SE00/02277

§ 371 (c)(1),
(2), (4) Date: Jan. 8, 2001

(87) PCT Pub. No.: WO01/38549

PCT Pub. Date: May 31, 2001

(30) Foreign Application Priority Data

Nov. 23, 1999 (SE) ................................. 9904247

(51) Int. Cl.[7] ........................ C12N 15/00; C12N 15/09; C12N 1/20; C12H 15/00; C07H 21/04; C12P 21/06

(52) U.S. Cl. ...................... 435/69.1; 435/6; 435/29; 435/91.4; 435/91.41; 435/252.3; 435/254.2; 435/320.1; 435/471; 536/24.1; 536/23.1

(58) Field of Search ................. 536/23.1, 24.1; 435/69.1, 320.1, 471, 252.3, 254.2, 91.4, 91.41, 6, 29

(56) References Cited

PUBLICATIONS

The Nucleotide Sequence of . . . ; M. Johnson et al., Nature, vol. 387, Supp. pp 87–90 (1997).
Yeast Sequencing Reports, Sequence Analysis of a 44 kb DNA . . . , M. Vandenbol et al., Yeast, vol. 11 pp 1069–1075 (1995).
Yeast Sequencing Reports, Sequence Analysis of a 37 6 kbp Cosmid . . . , P. Verhasselt et al., Yeast, vol. 13, pp 241–250 (1997).

*Primary Examiner*—Gerald G. Leffers, Jr.
(74) *Attorney, Agent, or Firm*—Nixon & Vanderhye

(57) ABSTRACT

The invention provides novel yeast promoters useful for controlling the expression of homologous and heterologous nucleic acid molecules in yeast cells. The yeast promoters are induced by a fermentable carbon source, such as glucose, or a non-fermentable carbon source, such as ethanol, or both. Therefore, expression of nucleic acid molecules encoding a polypeptide under the control of the novel yeast promoters may be regulated by varying the level of a fermentable carbon source, or a non-fermentable carbon source, or both.

12 Claims, 16 Drawing Sheets

Figure 13 YLR110C promoter region (SEQ ID NO:29)
Sequence shown: Chr XI1 370650 to 370051 (reverse orientation)

```
                1   AGAACCAAAT GGGAAAATCG AATGGGTCC AGAACTGCTT TGAGTGCTGG
                    TCTTGGTTTA CCCTTTTAGC CTTACCCAGG TCTTGACGAA ACTCACGACC
ATGCAAGCTTCGCGGCCGC         YLR-F
               51   CTATTGGCGT CTGATTTCCG TTTTGGGAAT CCTTTGCCGC GCGCCCCTCT
                    GATAACCGCA GACTAAAGGC AAAACCCTTA GGAAACGGCG CGCGGGGAGA

101   CAAAACTCCG CACAAGTCCC AGAAAGCGGG AAAGAAATAA AACGCCACCA
                    GTTTTGAGGC GTGTTCAGGG TCTTTCGCCC TTTCTTTATT TTGCGGTGGT

151   AAAAAAAAAA AATAAAAGCC AATCCTCGAA GCGTGGGTGG TAGGCCCTGG
                    TTTTTTTTTT TTATTTTCGG TTAGGAGCTT CGCACCCACC ATCGGGGACC

201   ATTATCCCGT ACAAGTATTT CTCAGGAGTA AAAAAACCGT TTGTTTTGGA
                    TAATAGGGCA TGTTCATAAA GAGTCCTCAT TTTTTTGGCA AACAAAACCT

251   ATTCCCCATT TCGCGGCCAC CTACGCCGCT ATCTTTGCAA CAACTATCTG
                    TAAGGGGTAA AGCGCCGGTG GATGCGGCGA TAGAAACGTT GTTGATAGAC

301   CGATAACTCA GCAAATTTTG CATATTCGTG TTGCAGTATT GCGATAATGG
                    GCTATTGAGT CGTTTAAAAC GTATAAGCAC AACGTCATAA CGCTATTACC

351   GAGTCTTACT TCCAACATAA CGGCAGAAAG AAATGTCAGA AAATTTTGCA
                    CTCAGAATGA AGGTTGTATT GCCGTCTTTC TTTACACTCT TTTAAAACGT

401   TCCTTTGCCT CCGTTCAAGT ATATAAAGTC GGCATGCTTG ATAATCTTTC
                    AGGAAACGGA GGCAAGTTCA TATATTTCAG CCGTACGAAC TATTAGAAAG

451   TTTCCATCCT ACATTGTTCT AATTATTCTT ATTCTCCTTT ATTCTTTCCT
                    AAAGGTAGGA TGTAACAAGA TTAATAAGAA TAAGAGGAAA TAAGAAAGGA

501   AACATACCAA GAAATTAATC TTCTGTCATT CGCTTAAACA CTATATCAAT
                    TTGTATGGTT CTTTAATTAG AAGACAGTAA GCGAATTTGT GATATACTTA
                                                           ← YLR-R      GT
              551   AATGCAATTT TCTACTGTCG CTTCTATCGC CGCTGTCGCC GCTGTCGCTT
                    TTACGTTAAA AGATGACAGC GAAGATAGCG GCGACAGCGG CGACAGCGAA
                    A          CCGGACC
```

YLR111W ORF = Underline

YLR110C ORF = Bold

YLR-F = SEQ ID NO:5

YLR-R = SEQ ID NO:6

Figure 14 YMR251WA promoter region (SEQ ID NO:30)

Sequence shown: CHR XIII 773951 TO 774800

```
  1   GCCACGGGTC AACCCGATTG GGATCACCCC ACTGGGGCCC AAGCCTGATA
      CGGTGCCCAG TTGGGCTAAC CCTAGTGGGG TGACCCCGGG TTCGGACTAT
                   AGCTAAGCTTCGCGGCCGC               YMR-F →
 51   TCCGACCTCC ATGAAATTTT TTTTTTTCTT TCGATTAGCA CGCACACACA
      AGGCTGGAGG TACTTTAAAA AAAAAAAGAA AGCTAATCGT GCGTGTGTGT

101   TCACATAGAC TGCGTCATAA AAATACACTA CGGAAAAACC ATAAAGAGCA
      AGTGTATCTG ACGCAGTATT TTTATGTGAT GCCTTTTTGG TATTTCTCGT

151   AAGCGATACC TACTTGGAAG GAAAAGGAGC ACGCTTGTAA GGGGGATGGG
      TTCGCTATGG ATGAACCTTC CTTTTCCTCG TGCGAACATT CCCGCTACCC

201   GGCTAAGAAG TCATTCACTT TCTTTTCCCT TCGCGGTCCG GACCCGGGAC
      CCGATTCTTC AGTAAGTGAA AGAAAAGGGA AGCGCCAGGC CTGGGCCCTG

251   CCCTCCTCTC CCCGCACGAT TTCTTCCTTT CATATCTTCC TTTTATTCCT
      GGGAGGAGAG GGGCGTGCTA AAGAAGGAAA GTATAGAAGG AAAATAAGGA

301   ATCCCGTTGA AGCAACCGCA CTATGACTAA ATGGTGCTGG ACATCTCCAT
      TAGGGCAACT TCGTTGGCGT GATACTGATT TACCACGACC TGTAGAGGTA

351   GGCTGTGACT TGTGTGTATC TCACAGTGGT AACGGCACCG TGGCTCGGAA
      CCGACACTGA ACACACATAG AGTGTCACCA TTGCCGTGGC ACCGAGCCTT

401   ACGGTTCCTT CGTGACAATT CTAGAACAGG GGCTACAGTC TCGATAATAG
      TGCCAAGGAA GCACTGTTAA GATCTTGTCC CCGATGTCAG AGCTATTATC

451   AATAATAAGC GCATTTTTGC TAGCGCCGCC GCGGCGCCCG TTTCCCAATA
      TTATTATTCG CGTAAAAACG ATCGCGGCGG CGCCGCGGGC AAAGGGTTAT

501   GGGAGGCGCA GTTTATCGGC GGAGCTCTAC TTCTTCCTAT TTGGGTAAGC
      CCCTCCGCGT CAAATAGCCG CCTCGAGATG AAGAAGGATA AACCCATTCG

551   CCCTTTCTGT TTTCGGCCAG TGGTTGCTGC AGGCTGCGCC GGAGAACATA
      GGGAAAGACA AAAGCCGGTC ACCAACGACG TCCGACGCGG CCTCTTGTAT

601 · GTGATAAGGG ATGTAACTTT CGATGAGAGA ATTAGCAAGC GGAAAAAAAC
      CACTATTCCC TACATTGAAA GCTACTCTCT TAATCGTTCG CCTTTTTTTG

651   TATGGCTAGC TGGGAGTTGT TTTTCAATCA TATAAAGGG AGAAATTGTT
      ATACCGATCG ACCCTCAACA AAAGTTAGT ATATTTCCC TCTTTAACAA

701   GCTCACTATG TGACAGTTTC TGGGACGTCT TAACTTTTAT TGCAGAGGAC
      CGAGTGATAC ACTGTCAAAG ACCCTGCAGA ATTGAAAATA ACGTCTCCTG

751   TATCAAATCA TACAGATATT GTCAAAAAAA AAAAAGACTA ATAATAAAAA
      ATAGTTTAGT ATGTCTATAA CAGTTTTTTT TTTTCTGAT TATTATTTTT
                                                ← YMR-R    G A
801   ATGAAGTTAT CTCAAGTTGT TGTTTCCGCC GTCGCCTTCA CTGGTTTAGT
      TACTTCAATA GAGTTCAACA ACAAAGGCGG CAGCGGAAGT GACCAAATCA
                C
```

YMR251W ORF = Underline
YMR251WA ORF = Bold
YMR-F = SEQ ID NO:7
YMR-R = SEQ ID NO:8

Figure 15 YMR107W PROMOTER REGION (SEQ ID NO:31)

Sequence shown: CHR XIII 482463 TO 483063

```
          1  AAAGAATCCA TCACTATTTG AAAAAAAGTC ATCTGGCACG TTTAATTATC
YMR107-F
AGCTAAGCTTCGCGGCCGC
         51  AGAGCAGAAA TGATGAAGGG TGTTAGCGCC GTCCACTGAT GTGCCTGGTA

101  GTCATGATTT ACGTATAACT AACACATCAT GAGGACGGCG GCGTCACCCC

151  AACGCAAAAG AGTGACTTCC CTGCGCTTTG CCAAAACCCC ATACATCGCC

201  ATCTGGCTCC TGGCAGGGCG GTTGATGGAC ATCAGCCGCC TCCCTTAATT

251  GCTAAAGCCT CCACAAGGCA CAATTAAGCA ATATTTCGGG AAAGTACACC

301  AGTCAGTTTG CGCTTTTATG ACTGGGTTCT AAGGTACTAG ATGTGAAGTA

351  GTGGTGACAG AATCAGGGAG ATAAGAGGGA GCAGGGTGGG GTAATGATGT

401  GCGATAACAA TCTTGCTTGG CTAATCACCC CCATATCTTG TAGTGAGTAT

451  ATAAATAGGA GCCTCCCTTC CTATTGCAAC TCCATAAAAT TTTTTTTTGT
                                                       MODIFICATION AT
        501  AGCCACTTCT GTAACAAGAT AAATAAAACC AACTAATCGA GATATCAAAT
                                                       GATTAGCT CTATAGTGTA

551  ATGGGTAGTT TTTGGGACGC ATTCGCAGTA TACGACAAGA AAAAGCACGC
             TACCCTACCTA YMR107-R
```

YMR107W ORF = Bold
YMR107-F = SEQ ID NO:9
YMR107-R = SEQ ID NO:10

Figure 16 ZEO1 PROMOTER REGION (SEQ ID NO:32)

Sequence shown: CHR XV 109746 TO 110346

ZEO1-F →
1    TTCAGGAGTC TCTCGCGTTA GAGCAGTACG TGGCGCAGCT AAACTCGCCG
AGCTAAGCTTCGCGGCCGC
51   GGAGGTCTGCTTCACGAGCG CGGTGTGCGC CTAGTATTGC CCCGACGGTC

101  CGGGTGCCTA TCCCTAGATT TCGTCGTGCC CCGACCCAAA TAGTTAAACG

151  TGTGGTTTAT GGGTGCACCA GGGCTTTATC GTGTTTTATA TCGATGGCGA

201  TTTGTGCCTC CAGTGTATTT TTGTATATCC AATTAAGGTT TCTTACCTAA

251  TTTTATTTTT ATCATCTTTA GTTAATGCTG GTTTGCTCTG TTTCTGCTGC

301  TTTCTGTGCG GTTCTCCTCT TCTCTTGTTT CTTCGTGTTG TCCCCCATCG

351  CCGATGGGCT TATATGGCGT ATATATATAG AGCGAGTTTT TACGTCGAAG

401  ATCATCTCAG TTTGCTTGAT AGCCTTTCTA CTTTATTACT TTCGTTTTTA

451  ACCTCATTAT ACTTTAGTTT TCTTTGATCG GTTTTTTTCT CTGTATACTT

501  AAAAGTTCAA ATCAAAGAAA CATACAAAAC TACGTTTATA TCAATTAATA
                                                GCAAATAT AGTTAATGTA

551  ATGTCTGAAA TTCAAAACAA AGCTGAAACT GCCGCCCAAG ATGTCCAACA
     TACGCTAGCAT ZEO1-R

YOL110W ORF = Underline
ZEO1 (YOL109W) ORF = Bold
ZEO1-F = SEQ ID NO:11
ZEO1-R = SEQ ID NO:12

US 6,716,601 B1

COMPOSITIONS AND METHODS UTILIZING THE YEAST ZE01 PROMOTER

BACKGROUND OF THE INVENTION

The controlled production in yeast of an enormous variety of useful proteins or polypeptides can be achieved using recombinant DNA technology. Yeast cells can be transformed with yeast expression vectors, which contain homologous or heterologous nucleic acid molecules encoding polypeptides (coding sequences). The yeast cells can then produce large quantities of the useful proteins or polypeptides in yeast cell culture.

Expression of the nucleic acid molecule encoding a polypeptide by the yeast expression vector is initiated at a region known as the promoter, which is recognized by and bound by RNA polymerase. The RNA polymerase travels along the DNA, transcribing the information contained in the coding strand from its 5' to 3' end into messenger RNA, which is in turn translated into a polypeptide having the amino acid sequence for which the DNA codes. The present invention provides novel yeast promoters useful for, inter alia, controlling the expression of homologous and heterologous nucleic acid sequences encoding proteins and polypeptides in yeast cells.

SUMMARY OF THE INVENTION

It is an object of the invention to provide novel yeast promoters, yeast expression vectors, and transformed yeast cells. It is a further object of the invention to provide a method for producing proteins and polypeptides in yeast cell culture.

In one embodiment of the invention a yeast promoter which comprises at least 17 contiguous nucleotides of an isolated and purified polynucleotide is provided. The promoter sequences are shown in SEQ ID NO: 1, SEQ ID NO:2, SEQ ID NO:3, and SEQ ID NO:4. The promoter is operative when operably linked to a nucleic acid molecule encoding a polypeptide.

As used herein, the term Apromoter@ refers to a nucleic acid sequence which is cable of initiating transcription of a nucleic acid molecule encoding a polypeptide (coding sequence); a Ayeast promoter@ is capable of initiating transcript of a coding sequence in yeast cells; and Apromoter activity@ refers to the level or amount of transcription initiation of a coding sequence, and encompasses any level above background (i.e., the level or amount that occurs in the absence of a promoter; a background level, which is normally zero).

Another embodiment of the invention provides a yeast promoter which comprises an isolated and purified polynucleotide. The promoter sequences are shown in SEQ ID NO: 1, SEQ ID NO:2, SEQ ID NO:3, and SEQ ID NO.4. The promoter is operative when operably linked to a nucleic acid molecule encoding a polypeptide.

Yet another embodiment of the invention provides a yeast promoter fragment which comprises at least 17 contiguous nucleotides of a polynucleotide. The polynucleotides are shown in SEQ ID NO: 1, SEQ ID NO:2, SEQ ID NO:3, and SEQ ID NO:4. The fragment has promoter activity as determined by cloning the fragment into a yeast expression vector, wherein the fragment is operably linked to a reporter gene, transforming yeast cells with the yeast expression vector, growing the yeast cells in yeast cell culture under conditions favorable for expression of the reporter gene, and assaying the yeast culture for a reporter protein expressed by the reporter gene. The expression of the reporter gene indicates the fragment has promoter activity.

Still another embodiment of the invention provides a yeast expression vector comprising a yeast promoter. The promoter sequences are shown in SEQ ID NO: 1, SEQ ID NO:2, SEQ ID NO:3, and SEQ ID NO:4. The promoter is operative when operably linked to a nucleic acid molecule encoding a polypeptide.

A further embodiment of the invention provides a yeast expression vector where activity of the promoter is controlled by varying the level of a non-fermentable carbon source, such as ethanol, in a medium of yeast cells in culture. The yeast cells are transformed with said yeast expression vector.

In yet another embodiment of the invention, a yeast expression vector comprising a yeast promoter which comprises at least 17 contiguous nucleotides of an isolated and purified polynucleotide is provided. The promoter sequences are shown in SEQ ID NO: 1, SEQ ID NO:2, and SEQ ID NO:4. Promoter activity is controlled by varying the level of a fermentable carbon source in a medium of yeast cells in culture, where the yeast cells are transformed with the yeast expression vector. The fermentable carbon source can be glucose.

Another embodiment of the invention provides a yeast expression vector comprising a yeast promoter. The yeast promoter comprises at least 17 contiguous nucleotides of an isolated and purified polynucleotide. The promoter sequences are shown in SEQ ID NO: 1, SEQ ID NO:2, and SEQ ID NO:4. Promoter activity is controlled by varying the level of a fermentable carbon source and a non-fermentable carbon source, such as ethanol, in a medium of yeast cells in culture, where the yeast cells are transformed with the yeast expression vector. The fermentable carbon source can be glucose. The non-fermentable carbon source can be ethanol.

Still another embodiment of the invention provides a yeast cell transformed with a yeast expression vector. The yeast expression vector comprises a yeast promoter. The promoter sequences are shown in SEQ ID NO: 1, SEQ ID NO:2, SEQ ID NO:3, and SEQ ID NO:4. The promoter is operative when operably linked to a nucleic acid molecule encoding a polypeptide.

Yet another embodiment of the invention provides a method for producing a polypeptide. A yeast expression vector is constructed where a polynucleotide encoding the polypeptide is controlled by a yeast promoter. The yeast promoter comprises at least 17 contiguous nucleotides of an isolated and purified polynucleotide. The promoter sequences are shown in SEQ ID NO: 1, SEQ ID NO:2, SEQ ID NO:3, and SEQ ID NO:4. The promoter is operative when operably linked to a nucleic acid molecule encoding a polypeptide. A culture of yeast cells is transformed with the yeast expression vector. The yeast cells are maintained in culture so that the polypeptide is expressed. The polypeptide is then recovered.

Still another embodiment of the invention provides a method for producing a polypeptide. A nucleic acid molecule encoding the polypeptide is cloned into an expression vector selected from the group consisting of pYLR110P+luc, pYMR251AP+luc, pYMR107P+luc, pZEO1P+luc, pYLR110P, pYMR251AP, pYMR107P, and pZEO1P. The nucleotide acid molecule is operably linked to a promoter of the expression vector. A culture of yeast cells is transformed with the yeast expression vector. The yeast cells are maintained in culture so that the polypeptide is expressed and the polypeptide is then recovered.

Another embodiment of the invention provides a method for producing a polypeptide. A yeast expression vector is constructed where a nucleic acid molecule encoding the polypeptide is controlled by a yeast promoter. The yeast promoter comprises at least 17 contiguous nucleotides of an isolated and purified polynucleotide. The promoter sequences are shown in SEQ ID NO: 1, SEQ ID NO:2, and SEQ ID NO:4. Yeast cells are transformed with the yeast expression vector and are maintained in culture medium. The expression of the nucleic acid molecule encoding the polypeptide is controlled by varying the level of a fermentable carbon source, such as glucose, in the culture medium. The polypeptide is then recovered.

Still another embodiment of the invention provides a method for producing a polypeptide. A yeast expression vector is constructed where a nucleic acid molecule encoding the polypeptide is controlled by a yeast promoter. The yeast promoter comprises at least 17 contiguous nucleotides of an isolated and purified polynucleotide. The promoter sequences are shown in SEQ ID NO: 1, SEQ ID NO:2, SEQ ID NO:3, and SEQ ID NO:4. The promoter is operative when operably linked to a nucleic acid molecule. A culture of yeast cells is transformed with the yeast expression vector. The yeast cells are maintained in culture medium and the expression of the nucleic acid molecule encoding the polypeptide is controlled by varying the level of a non-fermentable carbons source, such as ethanol, in the culture medium. The polypeptide is then recovered.

Another embodiment of the invention provides a method for producing a olypeptide. A yeast expression vector is constructed where a nucleic acid molecule encoding the polypeptide is controlled by a yeast promoter. The yeast promoter comprises at least 17 contiguous nucleotides of an isolated and purified polynucleotide. The promoter sequences are shown in SEQ ID NO: 1, SEQ ID NO:2, and SEQ ID NO:4. A culture of yeast cells is transformed with the yeast expression vector. The yeast cells are maintained in culture medium and the expression of the nucleic acid encoding the polypeptide is controlled by varying the level of a fermentable carbon source, such as glucose, and a non-fermentable carbon source, such as ethanol, in the culture medium. The polypeptide is then recovered.

Yet another embodiment of the invention provides a method of identifying a promoter fragment with promoter activity by generating a fragment comprising at least 17 contiguous nucleotides of an isolated and purified polynucleotide. The polynucleotides are shown in SEQ ID NO: 1, SEQ ID NO:2, SEQ ID NO:3, and SEQ ID NO:4. The fragment is cloned into a yeast expression vector, so that the fragment is operably linked to a reporter gene. Yeast cells are transformed with the yeast expression vector and grown in yeast cell culture under conditions favorable for expression of the reporter gene. The yeast culture is assayed for a reporter protein expressed by the reporter gene. Expression of the reporter gene indicates the fragment has promoter activity.

BRIEF DESCRIPTION OF THE DRAWINGS

FIG. 13 schematically illustrates the YLR110C promoter region.

FIG. 14 schematically illustrates the YMR251WA promoter region.

FIG. 15 schematically illustrates the YMR107W promoter region.

FIG. 16 schematically illustrates the ZEO1 promoter region.

DETAILED DESCRIPTION OF THE INVENTION

Figure 1:
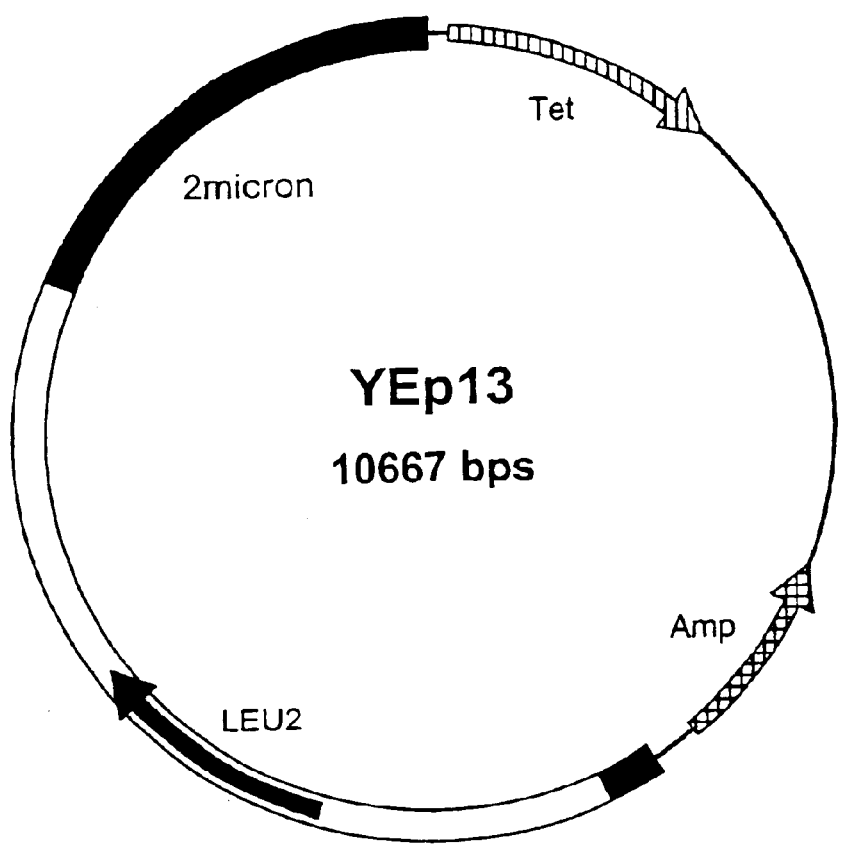
FIG. 1 is a map of YEp 13 expression vector.

Novel yeast promoters whose activity can be controlled by a fermentable carbon source, such as glucose, or a non-fermentable carbon source, such as ethanol, or both have been identified. The yeast promoters are useful for, inter alia, the high level production of proteins or polypeptides in yeast cell culture.

Yeast Promoters

The isolated and purified promoter polynucleotides of the invention are shown in SEQ ID NO:1 (the YLR110C promoter), SEQ ID NO:2 (the YMR251WA promoter), SEQ ID NO:3 (the YMR107W promoter), and SEQ ID NO:4 (the ZEO1 promoter). Yeast promoters comprising as little as 17 nucleic acids have been determined to function as promoters. The yeast promoters of the invention comprise at least 17, 25, 50, 75, 100, 150, 200, 250, 300, 350, 400, 450, 500, 600 or 700 contiguous nucleic acids of an isolated and purified polynucleotide up to the maximum length provided in any one of the sequences presented he rein, that is, SEQ ID NO: 1, SEQ ID NO:2, SEQ ID NO:3, and SEQ ID NO:4.

Preferably, the promoter polynucleotides are isolated free of other components, such as proteins and lipids. The polynucleotides can be made by a cell and isolated or can be synthesized n the laboratory, for example, using an automatic synthesizer or an amplification method such as PCR.

Naturally occurring variants and artificial sequence variants (that is, those which do not occur in nature) of the promoters are included in the invention. Variants of the promoters and/or fragments thereof have, along their entire length, sequence identity of at least 90%, and preferably greater than 95% as determined by the Smith-Waterman homology search algorithm as implemented in MPsrch™ program (University of Edinburgh) using an affine gap search with the following search parameters: gap open penalty: 12, gap extension penalty: 1.

Fragments of the full-length promoters are also functional as promoters. A promoter fragment of at least 17 contiguous nucleotides may occur at any position along the full-length promoter as shown in SEQ ID NO: 1, SEQ ID NO:2, SEQ ID NO:3 or SEQ ID NO:4. Accordingly, promoter activity of 17 or more contiguous nucleotides occurring anywhere along the full-length promoter can be analyzed. Fragments of 17, 25, 50, 75, 100, 150, 200, 250, 300, 350, 400, 450, 500, 550, 600, 650 or 700, nucleotides of the promoters may be constructed by, for example, subjecting an isolated promoter to restriction endonucleases, to 5'- or 3'-deletion mutagenesis, to PCR, or to site specific deletion. A combination of these methods can also be used to generate fragments of a promoter.

The invention further embodies a hybrid promoter, i.e., a promoter that comprises more than one promoter or more than one fragment of a promoter from which it was derived. The promoter fragments can be derived from more than one of the promoter sequences shown in SEQ ID NO: 1, SEQ ID NO:2, SEQ ID NO:3 and SEQ ID NO:4. The promoters and fragments can be constructed as described above, ligated together, and cloned into a yeast expression vector. Where a promoter comprises nucleotides from at least two polynucleotides selected from the group consisting of SEQ ID NO: 1, SEQ ID NO:2, SEQ ID NO:3 and SEQ ID NO:4, at least 5,6,7, 8,9,10,25,50,75,100,150,200,250,300,350, 400, 450, 500, 550, 600, or 650 contiguous nucleotides are derived from each of the lynucleotides to form a promoter of at least 17 nucleotides. Alternatively, each of the full-length promoters can be combined with another full-length promoter or with fragments of other promoter.

The yeast promoters, fragments of the promoters, and hybrid promoters are useful for controlling expression of a protein or polypeptide when the yeast promoter is operably linked to a nucleic acid molecule encoding the protein or polypeptide.

Determination of Promoter Activity

Promoters and fragments of promoters can be assayed for promoter activity by cloning a fragment of a promoter, or a full-length promoter, or a hybrid promoter into a yeast expression vector so that is operably linked to a reporter gene, i.e., a coding sequence for a reporter protein. The yeast expression vector is transformed in yeast cells, which are grown in yeast cell culture, under conditions favorable for expression of the reporter gene, for example, under conditions providing a fermentable and/or non-fermentable carbon source. Expression of the reporter gene, as determined by an assay for the amount of a reporter protein expressed by the reporter gene, indicates that the promoter has activity.

For example, to determine if a promoter has activity, i.e. is operative, expression of a reporter gene by a promoter of the invention may be compared to expression of the reporter gene by a reference promoter such as PBR1 (Cottingham et al. (1991) Eur J Biochem 196(2):431–8; Sleep et al. (1991) Biotechnology 9(2):183–7; Finnis et at. (1992) Yeast 8(1) :57–60; Meldgaard et al.(1995) Glycoconj J 12(3):380–90; Bach et al. (1996) Receptors and Channels 4(2):129-39. A promoter, a fragment of a promoter, or a hybrid promoter of the invention is operative if it expresses at least 25% of the amount of a reporter protein as the full-length PBR1 promoter in a medium containing a non-fermentable carbon source, or a fermentable carbon source, or both. Preferably, an operative promoter expresses at least 50%, 75%, 100%, 200%, 300%, 400%, or more of the amount of a reporter protein as the full-length PBR1 reference promoter.

Assays for promoter activity are useful for identifying yeast promoters with high activity and the specific nucleotide sequences of the promoters that are necessary for promoter activity.

Yeast Expression Vectors

The yeast promoters of the invention, which comprise isolated and purified polynucleotides selected from the group consisting of SEQ ID NO: 1, SEQ ID NO:2, SEQ ID NO:3, and SEQ ID NO:4 or fragments thereof, can be used to construct yeast expression vectors.

Yeast expression vectors are any vectors capable of autonomous replication within a yeast host organism or capable of integrating into the yeast genome. Yeast expression vectors are useful for introducing foreign DNA into yeast cells. Typical yeast expression vectors include yeast integrative plasmids (YIp), yeast replicating plasmids (YRp), yeast expression plasmids (YXp), yeast centromere-containing plasmids (YCp), and yeast episomal plasmids (YEp). Preferably, a yeast expression vector can be selected and maintained in both yeast and *E. coli*.

Yeast expression vectors, typically plasmids, incorporate the yeast promoters of the invention to control expression of nucleic acid molecules encoding heterologous or homologous proteins or polypeptides. The nucleic acid molecules are operably linked to a promoter in the yeast expression vector. A wide range of heterologous eukaryotic and prokaryotic proteins or peptides may be expressed by the vectors of the invention.

Expression vectors incorporating the promoters can be constructed by inserting into a vector a nucleic acid molecule encoding a protein or polypeptide (coding sequence) which is to be expressed. The coding sequence can be inserted at a restriction site which is provided downstream of a translation start codon controlled by the promoter. The coding sequence must be inserted in the correct translational reading frame.

Alternatively, the polynucleotide can itself be provided with a translational start codon followed directly by a coding sequence. Where the promoter does not contain a translational start codon, a restriction site is provided so that the coding sequence can be inserted in the correct reading fame and so that its translational start codon is correctly positioned in relation to the promoter. The coding sequence can encode heterologous or homologous or eukaryotic or prokaryotic polypeptides or proteins. In a preferred embodiment the coding sequence encodes a fusion protein. The coding sequence may further comprise a signal sequence.

In addition to the promoters of the invention, other components can be added to the expression vectors of the invention. For example, yeast selective markers, such as LEU2 or TRP1, which allow for selection of yeast cells that have been effectively transformed by the vector can be added. A yeast replication origin, such as the replication origin of the 2-micron plasmid or the autonomous ARS replication segment can be added. Upstream activating sequences and transcription terminator sequences may be added. Further, at least a portion of a bacterial plasmid, such as found in YEp13, can be added to enable the yeast expression vector manipulated in an intermediate bacterial host system, such as *Escherichia coli*.

The expression vector may also comprise a reporter gene which encodes, for example, β-galactosidase or luciferase. The reporter gene can be under the control of a promoter of the invention. Where the reporter gene, ie., coding sequence, is linked to a gene encoding a desired protein, assaying the level of expression of the reporter protein can quickly and easily determine the level of expression of the desired protein.

The expression vectors of the invention can be used to direct the fermentable carbon source- and/or non-fermentable carbon source-induced high level expression of proteins or polypeptides in yeast. The promoters of the invention can be induced by the presence of a fermentable carbon source, such as glucose, or a non-fermentable carbon source, such as ethanol, or both. That is, the promoters have greater promoter activity in the presence of a fermentable carbon source, or a non-fermentable carbon source, or both than in the absence of a fermentable carbon source, or a non-fermentable carbon source, or both. Promoters YLR110C, as shown in SEQ ID NO: 1; YMR251WA, as shown in SEQ ID NO:2; and ZEO1, as shown in SEQ ID NO:4, can be induced by a fermentable carbon source, such as glucose, or by a non-fermentable carbon source, such as ethanol, or by both. Promoter YMR107W, as shown in SEQ ID NO:3, can be induced by a non-fermentable carbon source, such as ethanol. Thus, the amount of expression of a homologous or heterologous nucleic acid molecule encoding a protein operably linked to the promoters of the invention can be controlled by varying the amount of an available fermentable carbon source, such as glucose, or a non-fermentable carbon source, such as ethanol, or both.

Transformed Yeast Cells

Yeast cells can be transformed with the yeast expression vectors of the invention. Transformation can be accomplished by well known methods, including, but not limited to electroporation, calcium phosphate precipitation, and microinjection. The yeast expression vectors of the invention can be used to transform yeast cells, including, but not limited to *Saccharomyces cerevisiae, S. uvarum, S. carlsbergensis, Saccharomycopsis lipolytica, Schizosacchromyces pombe*, and *Ktuyveromyces lactis*.

Transformed yeast cells containing a yeast expression vector can be grown in an appropriate medium for the yeast. A fermentable or non-fermentable carbon source can be added to the yeast culture medium in order to control the activity of the promoter.

Methods of Production of Proteins

Yeast cells transformed with expression vectors comprising a promoter of the invention can be used to produce proteins and polypeptides. Under proper cell culture conditions, preferably in the presence of a fermentable or non-fermentable carbon source, or both, the promoters of the invention will control expression of a nucleic acid molecule encoding polypeptide operably linked to the promoter.

The protein or polypeptide can be retained within the yeast cell. The yeast cells can be then harvested, lysed, and the protein obtained and substantially purified in accordance with conventional techniques. Such techniques include, but are not limited to chromatography, electrophoresis, extraction, and density gradient centrifugation.

In a preferred embodiment of the invention, the protein or polypeptide to be recovered will further comprise a signal peptide capable of transporting the protein or polypeptide through the membrane of a transformed yeast cell. The protein or polypeptide can be recovered from the culture medium by, for example, adsorption or precipitation.

Further, the proteins and polypeptides may be produced as a fusion protein, which includes not only the amino acid sequence of the desired protein, but also one or more additional proteins. Affinity purification protocols can be used to facilitate the isolation of fusion proteins. Typically, a ligand capable of binding with high specificity to an affinity matrix is chosen as the fusion partner for the desired protein. For example, fusion proteins made with glutathione-S-transferase can be selectively recovered on glutathione-agarose and IgG-Sepharose can be used to affinity purify fusion proteins containing staphylococcal protein A.

Preferably, the protein or polypeptide of interest can be separated from the remainder of the fusion protein., The fusion protein can be constructed so that a site for proteolytic or chemical cleavage is inserted between the protein of interest and the fusion partner. For example, sites for cleavage by collagenase, Factor Xa protease, thrombin, and enterokinase, have been inserted between the fusion partner and the protein of interest. The protein of interest can be also cleaved from the remainder of the fusion protein by chemical cleavage by, for example, hydroxylamine, cyanogen bromide (CNBr), or N-chlorosuccinamide.

The following are provided for exemplification purposes only and are not intended to limit the scope of the invention described in broad terms above. All references cited in this disclosure are incorporated by reference.

EXAMPLE 1

Preparation of Yeast Samples

*S. cerevisiae* strain 11C.

This example describes the growth of haploid *Saccharomyces cerevisiae* strain 11C. It has the genotype: ade2-161, trp1-Δ63, ura3-52, lys2-801, leu2Δ1 &/or leu2–112, his3Δ200 &/or his4-519. 11C was generated by crossing the strains YPH500 (Mat a ura3-52 lys2-801 ade2-161 trp1-Δ63 his 3Δ200 leu2Δ1) (Sikorski and Hieter. (1989) A system of shuttle vectors and yeast host strains designed for efficient manipulation of DNA in *Saccharomyces cerevisiae. Genetics* 122: 19–27) and AH22 (MATa leu2-3 leu2-112 his4-519) (Hinnen et al. (1978) Transformation of yeast. *Proc. Natl. Acad. Sci. USA* 75: 1929–1933).

Three sterile 500 ml conical flasks, each containing 100 ml sterile YPD broth (Sigma, Cat No. Y-1375) were inoculated with sterile 10 μl loops of differing quantities of the *S. cerevisiae* strain 11C from a freshly streaked YPD plate (Sigma, Cat No. Y-1500), and grown in an orbital shaker at 30° C., 200 rpm, overnight. The growth of 11C in the three flasks was measured by absorbance at 600 nm. One flask was deemed to be at the late exponential growth phase (1.98 ODU ml at 600 nm), and this culture was used to inoculate (50 ml o/n culture per flask) 2 identical 5L sterile conical flasks (labeled E and L), each containing 1L sterile YPD broth to a final concentration of ~0.1 ODU ml. Flasks E and L were grown in an orbital shaker at 30° C., 200 rpm. 10 ml samples were collected at times indicated below (Table 1). The samples were treated as follows: their growth was determined (A600nm), the possibility of contamination was checked (using a light microscope), cells were harvested in a benchtop centrifuge (~2000×g for 5 minutes), and the supernatant removed and frozen at −20 C. (samples labeled E0–E3, and L0–L5).

TABLE 1

Growth of cultures E and L as measure by absorbance at 600 nm.

| Time Point | Time after inoculation (min) | Growth of flask E (ODU) | Growth of flask L (ODU) |
| --- | --- | --- | --- |
| T0 | 0 | 0.099 | 0.099 |
| T1 | 310 | 0.37 | 0.36 |
| T2 | 410 | 0.71 | 0.72 |
| T3 | 455 | 0.97 | 0.92 |
| T4 | 775 | — | 3.64 |
| T5 | 1420 | — | 6.05 |

After 455 minutes, a time deemed to be late exponential growth phase in glucose, flask E (i.e. early) was harvested (~2000×g for 5 minutes), split into 50 ml aliquots, and frozen at −80° C. After 1420 minutes, a time deemed to be growth on ethanol, flask L (i.e. late) was harvested (~2000×g for 5 minutes), split into 50 ml aliquots, and frozen at −80° C.

Determination of Glucose and Ethanol concentration

Supernatant samples (E0–E3, and L0–L5) were defrosted, and their ethanol and glucose contents were measured using ethanol (Boehringer, Cat. No. 176290) and glucose (Boehringer, Cat. No. 176251) detection kits according to manufacturers instructions. The concentrations determined are shown below in Table 2.

TABLE 2

Glucose and Ethanol concentrations in supernatants of cultures E and L at different time points.

| Sample | Time after inoculation (min) | Glucose level in media (g $L^{-1}$) | Ethanol level in media (g $L^{-1}$) |
| --- | --- | --- | --- |
| E0 | 0 | 20.0 | 0.0 |
| E1 | 310 | 21.8 | 0.3 |
| E2 | 410 | 21.8 | 0.8 |
| E3 | 455 | 21.2 | 0.87 |
| L0 | 0 | 20.0 | 0.0 |
| L1 | 310 | 22.2 | 0.36 |
| L2 | 410 | 22.0 | 0.62 |
| L3 | 455 | 20.0 | 0.87 |
| L4 | 775 | 11.8 | 5.2 |
| L5 | 1420 | 0.0 | 11.8 |

It can seen in Table 2 that at the point of culture harvest for E (E3, 455 minutes), the cells were still utilizing glucose as a carbon source, while at the point of culture harvest for L (L5, 1420 minutes), glucose was exhausted, and the cells were utilizing ethanol as a carbon source. Calibration values used to calculate glucose concentrations are shown in Table 3.

Calibration values used to calculate ethanol concentrations are shown in Table 4.

TABLE 3

Glucose standards

| GLUCOSE STANDARDS g/l | OD A340 |
| --- | --- |
| 0 | 0 |
| 0.2 | 0.246 |
| 0.4 | 0.461 |
| 0.6 | 0.726 |
| 0.8 | 0.967 |
| 1 | 1.227 |

TABLE 4

Ethanol standards

| ETHANOL STANDARDS g/L | OD A340 |
| --- | --- |
| 4.72 | 0.041 |
| 9.44 | 0.083 |
| 18.88 | 0.166 |
| 37.76 | 0.322 |
| 56.6 | 0.534 |
| 75.5 | 0.664 |
| 94.4 | 0.846 |

EXAMPLE 2

Analysis of RNA Levels From Yeast Dimorphic Growth Samples

Total RNA Isolation

To RNA was isolated from 300 ml of culture using the hot phenol protocol. The frozen ye t pellets were resuspended in lysis buffer (4 ml) (0.5 ml Tris-CL (1M, pH 7.5), 1.0 ml EDTA 0.5 M), 2.5 ml 10% SDS, and 46.0 ml dd$H_2O$) and an equal volume of acid phenol was added an vortexed. Following incubation at 65° C. for one hour (with occasional vigorous vortexing) the mixture was placed on ice for 10 minutes then centrifuged (10 minutes). The aqueous layer was transferred to a fresh centrifuge tube and mixed with an equal volume of phenol at room temperature. The mixture was centrifuged and an equal volume of cloroform was mixed with the aqueous layer in a fresh centrifuge tube. Following centrifugation the aqueous layer was transferred to a fresh centrifuge tube and sodium acetate (to a final concentration of 0.3M) and two volumes of 100% ethanol was added to precipitate the RNA. The mixture was placed at −20 C. for 30 minutes then centrifuged for 10 minutes to pellet the RNA. The RNA pellet was washed 2–3 times with 70% ethanol hen allowed to dry at room temperature. The pellet was resuspended in ddH2O (200–500 $\mu$). The RNA was quantitated by measuring OD 260–280. Yield of total RNA was ~4.5 mg from each culture.

Poly A+RNA Purification

Poly A+RNA was purified from total RNA using Qiagen Oligotex mRNA Midi Kit (Qiagen, Cat. No. 70042). 2 mg of total RNA was used as starting material and made up to a volume of 500 $\mu$l with DEPC treated $H_2O$. To this 500 $\mu$l buffer OBB (2×binding buffer) and 55 $\mu$l oligotex suspension was added. The "Oligotex mRNA SpinColumn Protocol" from, the kit protocol booklet was followed. The pelleted mRNA was washed in 200 $\mu$l 75% ethanol, dried and resuspended in 10 $\mu$l DEPC treated $H_2$. Yield of Poly A+RNA was ~8 $\mu$g for each sample.

cDNA Synthesis cDNA was synthesized using the protocol for GeneChip Expression Analysis Manual using reagent from Gibco BRL Life Technologies Superscript Choice System cat. No. 18090-019. For each sample 5 $\mu$g Poly A+RNA was added to 100pmol of T7-(dT)$_{24}$ primer (sequence: GGCCAGT-GAATTGTAATACGACTCACTATAGGG AGGCGG-(T) 24, HPLC purified) (SE ID NO:15) in a total of 8 $\mu$l (made up to volume with DEPC treated $H_2O$). The reaction mixture was incubated for 10 minutes at 70° C. in a Perkin Elmer PE9600 thermalcycle then put on ice. The following reagents were added to the reaction mixture: 4 $\mu$l 5× first s rand cDNA buffer; 2$\mu$l 0.1M DTT; and 1 $\mu$l 10 mM dNTP mix. The reaction mixture was mixed and incubated at 37° C. for 2 minutes in a Perkin Elmer PE9600 thernocycle. 5 $\mu$l SuperScript II reverse transcriptase was then added. The mixture was incubated at 37° C. for 1 hour in a Perkin Elmer PE9600 thermocycler.

The first strand cDNA reaction was placed on ice and the following reagents added: 91 $\mu$l DEPC treated $H_2O$; 30 $\mu$l 5×second strand reaction buffer; 3 $\mu$l 10 mM dNTP mix; 1 $\mu$l 10 units/$\mu$l E. coli DNA ligase; 4 $\mu$l 10 units/$\mu$l E. coli DNA Polymerase I; and 1 $\mu$l 2units/$\mu$l RNase H. The mixture was incubated at 16° C. for 2 hours in a Perkin Elmer PE9600 thermalcycler. 2 $\mu$l 5 units/$\mu$l T4 DNA Polymerase was then added. The mixture was incubated or a further 5 minutes at 16° C. in a Perkin Elmer PE9600 thermalcycler. 10 $\mu$l 0.5M EDT was then added.

The double stranded DNA was cleaned up by phenol extraction. The reaction product transferred to a 1.5 ml eppendorf tube and 162 $\mu$l Tris pH 8.0 saturated phenol was added. The tube was mixed by vortexing, the tube was then centrifuged in a microfuge at 13,000 rpm for 5 minutes. The top fraction was recovered and cDNA precipitated by addition of 60 $\mu$l 7.5M ammonium acetate plus 4001 $\mu$l absolute ethanol. This was immediately centrifuged in microfuge at 13,000 rpm for 20 minutes. The supernatant fraction was discarded, the pellet was washed in 75% ethanol and then air-dried. The pellet was resuspended in 20 µl DEPC treated H₂O Synthesis of Biotin-Labeled cRNA by In Vitro Transcription (IVT)

Reagents from Ambion MEGAscript T7 kit, cat. No. 1334, were used for the synthesis of biotin-labeled cRNA by in vitro transcription (IVT). The NTP Labeling mix comprised 7.5 mM ATP; 7.5 mM GTP; 5.625 mM UTP; 1.875 mM Biotin-16-UTP (Enzo cat No. 42814); 5.62 mM CTP; and 1.875 mM Biotin-11-CTP (Enzo cat No. 42818). The IVT Labeling reaction comprised: 14.5 µl NTP Labeling mix; 2 µl 10 ×Ambion Transcription Buffer; 1.5 µl Double strand cDNA (from above); and 2 µl Ambion T7 Enzyme Mix.

The reaction mixture was incubated for 6 hours at 37° C. in a Perkin Elmer PE9600 thermalcycler. The biotinylated CRNA was cleaned up using Qiagen RNeasy kit, cat No. 74103. The RNeasy kit protocol was followed exactly. RNA was eluted in 2 aliquots of 30 µl DEP treated H₂O. The RNA was precipitated by addition of 6 µl 3M sodium acetate pH 5.5 plus 75 µl absolute ethanol. The RNA was allowed to precipitate overnight at −20° C. Samples ere centrifuged in a microfuge at 13,000 rpm for 20 minutes to pellet the RNA. The supernatant fraction was discarded and the pellet was washed in 1 ml of 75% ethanol and then allowed to air dry. The pellet was then resuspended in 20 µl DEPC treated H₂O. The yield of RNA was ~40 µg for each sample.

RNA Fragmentation

11 µg of cRNA was fragmented. 8 µl of 5× Fragmentation buffer (200 mM Tris-Acetate pH 8 1, 500 mM potassium acetate, 150 mM magnesium acetate) plus 11 µg cRNA made up to 20 µl with DEPC treated H₂O was used. The reaction mixture was incubated 94° C. for 35 minutes in a Perkin Elmer PE9600 thermal cycler.

Hybridization to GeneChip Microarray

The hybridization mix comprised: 20 µl (11 µg) of fragmented cRNA; 2.2 µl of control oligo B2 (50 mol/µl) (sequence: 5'Biotin-GTCAAGATGCTACCGTTCAG 3' HPLC purified) (SEQ ID NO:16); 2.2 µl Herring Sperm DNA (10 mg/ml); 110 µl 2× Buffer (2mM NaCl, 20 M Tris pH 7.6, 0.01% Triton X-1 00); and 85.6 µl DEPC treated H₂O. The hybridization mix heated to 95° C. l na Techne hot block for 5 minutes, followed by incubation at 40° C. for 5 minutes. The hybridization mix was clarified by centrifugation in microfuge at 13,000 rpm for 5 minutes.

200 µl of supernatant to added to the Genechip cartridge (GeneChip cartridge was previously pre-wetted with 200 µl 1×Buffer and incubated for 10 minutes at 40° C. in the rotisseric box of a GeneChip hybridization over 320 (cat No. 800227) at maximum rpm. The sample was hybridized to the microrray overnight at 40° C. in a GeneChiphybridization over inthe rosseric at maximum rpm.

Washing and Stainig of Probe Arrays

The hydridization mix was recovered from the GeneChip cartridge and put back in the tube containing the remainder of the sample. 200 µl 6×SSPE-T (6×SSPE plus 0.005% Triton X-100 was applied to the chip and pipetted in and out twice. This process was repeated twice more. Another 200 µl 6×SSPE-T was applied to the cartridge and the cartridge was then incubated for 1 hour at 50° C. at maximum rpm in the GeneChip hybridization oven. The 6×SSPE-T was removed and 200 µl 0.5×SSPE-T was added to cartridge. The cartridge was incubated for 15 minutes at 50° C. at maximum rpm in the GeneChip by hybridization oven. The 0.5× SSPE-T was removed and the cartridge was re-filled with 200 µl 6×SSPE-T.

The stain solution comprised: 190 µl 6×SSPE-T; 10 µl of 20 mg/ml acetylated BSA; and 2 µl mg/ml conjugated streptavidin:phycoerythrin (Molecular Probes cat. No. S-866). 200 µl 6×SSPE-T was removed from the GeneChip cartridge and 200 µl of stain solution added. The cartridge was incubated at ambient temperature in a GeneChip hybridization oven at maximum rpm in the rotisserie for 10 minutes. The stain solution was removed and the cartridge was washed by adding 200 µl 6×SSPE-T and pipetting this in and out of the cartridge t . This process was repeated six times. The cartridges were then completely filled with 6×SSPE-T and any bubbles removed. Hybridization, washing and staining was repeated using the same hybridization mixes until both samples had been hybridized to each of the four yeast chip sub-set arrays.

Data Collection

Data was collected by scanning the hybridized chips on a Hewlett-Packard GeneArray scanner. A "halo" effect (appearance of stain non-specifically across the array image) was seen on one of the scanned images: yeast growing in glucose rich media, sub-set C array. Scanning of this array was aborted after one scan and the chip was washed twice with 200 µl 6×SSPE-T and then re-filled as before. This array was then re-scanned three times and the data collected was the average of these three scans. All other arrays were scanned four times without problems and the data collected was the average of the four scans.

EXAMPLE 3

Isolation of Promoters and Construction of Expression Vectors.

PCR Amplification of Promoter Regions from Genoinic DNA

Based on the *Saccharomyces cerevisiae* genomic sequence in the GenEMBL nucleotide database oligonucleotide primers were designed to amplify the genomic sequence 5' to the following ORFs: YLR110C (Johnson et al. (1997) Nature 1997 May 29;387(6632 Suppl):87–90), YMR251WA (common name HOR7) (Bowman et al. (1997) Nature May 29;387(6632 Suppl):90–3), YMR107W (Bowman et al. (1997) Nature May 29;387 (6632 Suppl) :90–3), and YOL109W (common name ZEO1) (Dujon et al. (1997) Nature May 29;387(6632 Suppl):98–102). The region amplified was the non-coding region separating the selected ORF and the next predicted *Saccharomyces cerevisiael* ORF in the 5' direction, with a minimum length of 500 bp.

Sequence of Oligonucleotide Primers used to Amplify Promoter DNA

| YLR110C-F | ATGCAAGCTTCGCGGCCGCCGTCTGATTTCCGTTT | SEQ ID NO:5 |
|---|---|---|
| YLR110C-R | CCAGGCCGCATATGTCATATAGTGTTTAAG | SEQ ID NO:6 |
| YMR251WA-F | AGCTAAGCTTCGCGGCCGCCTTTCGATTAGCACGCAC | SEQ ID NO:7 |

-continued

| | | |
|---|---|---|
| YMR251WA-R | AGATACCTT<u>CATATG</u>TTATTATTAGTC | SEQ ID NO:8 |
| YMR107W-F | AGCT<u>AAGCTT</u>CGCGGCCGCGCAGAAATGATGAAGG | SEQ ID NO:9 |
| YMR107W-R | ATCCATCC<u>CATATG</u>TGATATCTCGATTAG | SEQ ID NO:10 |
| ZEO1-F | AGCT<u>AAGCTT</u>CGCGGCCGCGGAGGTCTGCTTCACG | SEQ ID NO:11 |
| ZEO1-R | TACGATCG<u>CATATG</u>TAATTGATATAAACG | SEQ ID NO:12 |

PCR reactions were set up for each primer pair as follows: For YMR251WA and ZEO1 90 µl of Reddy-Load PCR (1.1X) mix, 3.5 mM MgCl$_2$. (Advanced Biotechnologies, cat. no. AB-0628); 2 µl of forward primer (100 µM); 2 µl of reverse primer (100 µM); 1 µl of S. cerevisiae genomic DNA (Promega G310A, lot 8347702, 276 µg/ml); and 5 µl of H$_2$O were combined.

For YLR110C and YMR107W 90 µl of Reddy-Load PCR (1.1X) mix, 1.5 mM MgCl$_2$ (Advanced Botechnologies, cat.no. AB-0575); 2 µl of forward primer (100µM); 2 µl of reverse primer (100 µM); 1 µl of S. cerevisiae genomic DNA (Promega G310A, lot 8347702, 276 µg/ml): and 5 µl of H$_2$O were combined.

The thermocycling was carried out as follows: For the YMR251WA promoter: 94° C. for 5 minutes followed by 30 cycles of: 94° C. for 30 seconds, 60° C. for 30 second, 72° C. for 1 minute, followed by 72° C. for 5 minutes. The reaction mixtures were then held at 4° C. For the YMR107W and ZEO1 promoters: 94° C. for 5 minutes followed by 30 cycles of: 94° C. for 30 seconds, 45° C. for 30 seconds, 72° C. for 1 minute; followed by 72° C. for 5 minutes. The reaction mixtures were then held at 4° C. For the YLR110C promoter: 94° C. for 5 minutes followed by 30 cycles of: 94° C. for 30 seconds, 50° C. for 30 seconds, 72° C. for 1 minute; followed by 72° C. for 5 minutes. The reaction mixtures were then held at 4° C.

The PCR solutions were loaded onto an LMP gel and the bands were purified using Wizard PCR reps (Promega, cat. no. A7170) according to protocol, eluted in 50 µl, ethanol precipitated, and resuspended in 20 µl. A map of the YLR110C promoter region is shown in FIG. 13 and SEQ ID NO:29. A map of the YMR251WA promoter region is shown in FIG. 14 and SEQ ID NO:30. A map of the YMR107W promoter region is shown in FIG. 15 and SEQ NO:31. A map of the ZEO1 promoter region is shown in FIG. 16 and SEQ ID NO:32.

Cloning Promoter Regions Into a Yeast Vector Containing the Luciferase Gene

Figure 2:
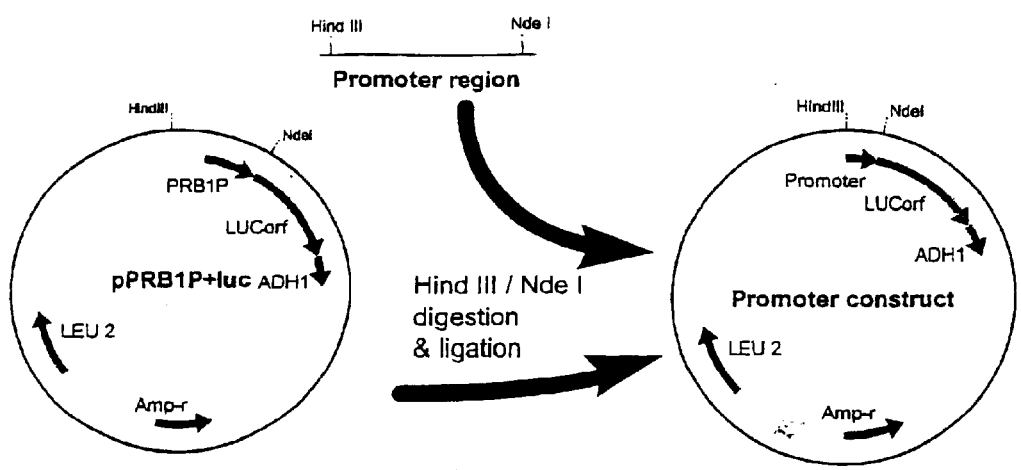
FIG. 2 schematically illustrates construction of YLR110C and YMR251WA promoter constructs.
Figure 3:
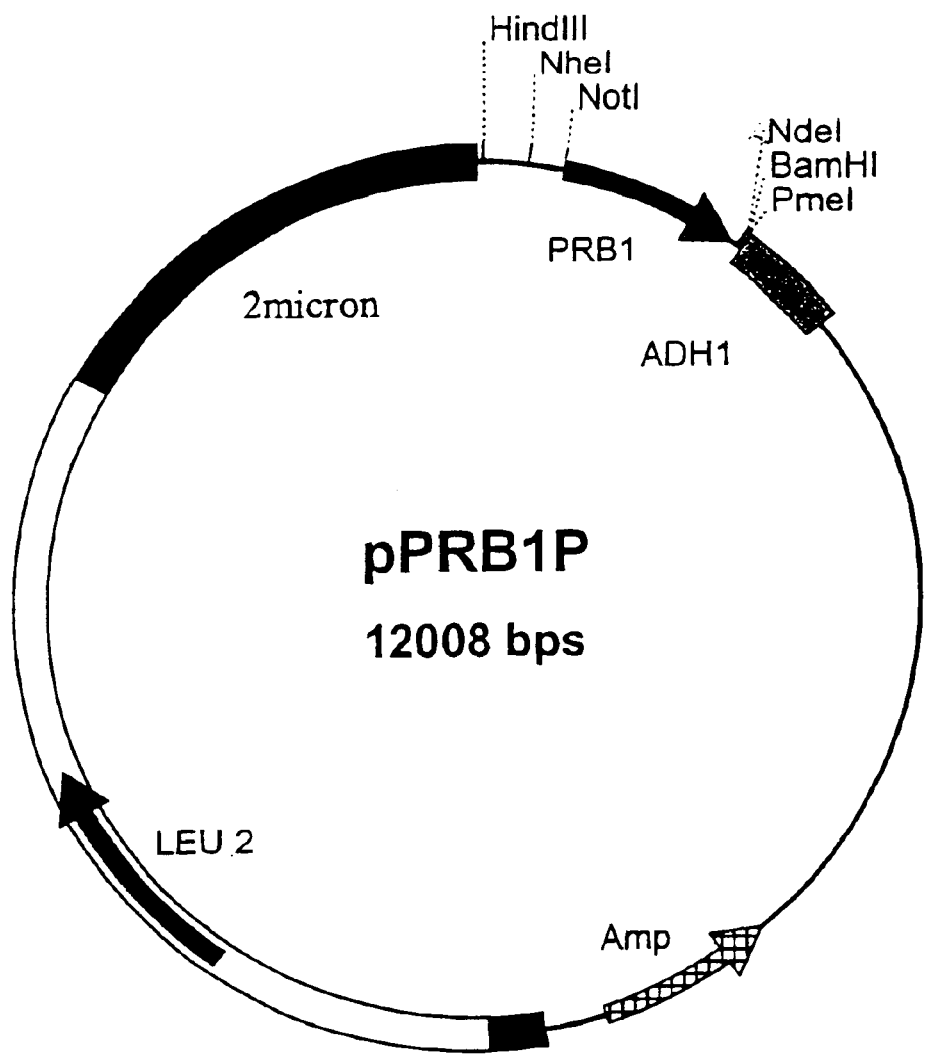
FIG. 3 is a map of pPRB1P.
Figure 4:
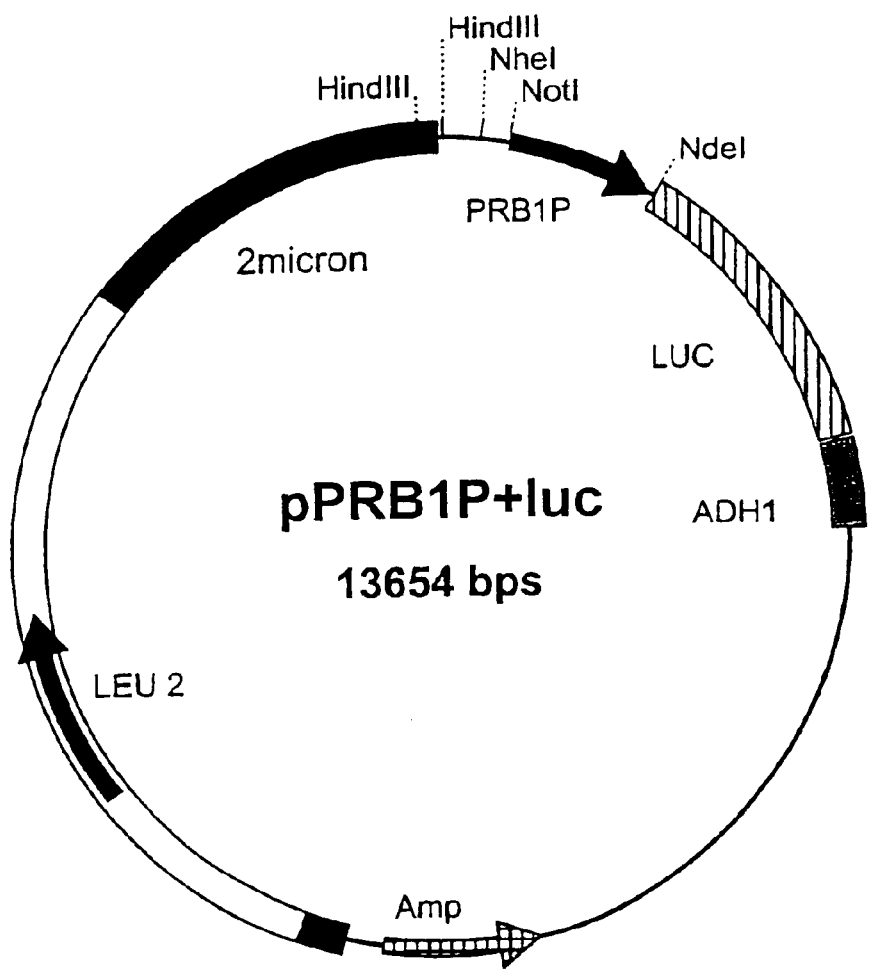
FIG. 4 is a map of pPRB1P+luc.
Figure 5:
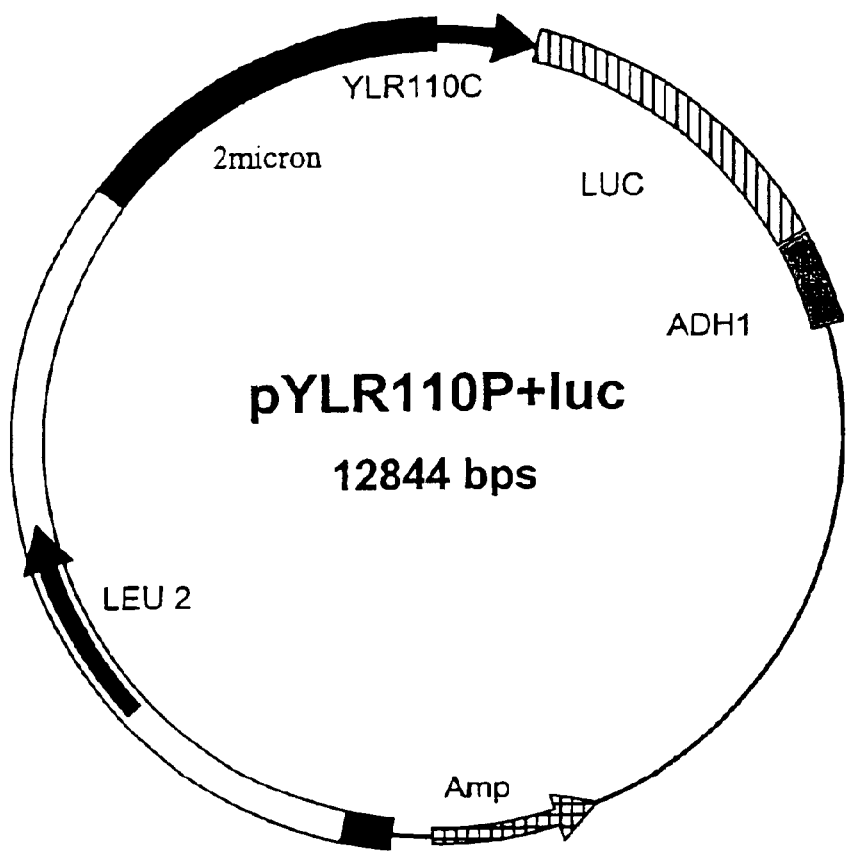
FIG. 5 is a map of pYLR110P+luc.
Figure 6:
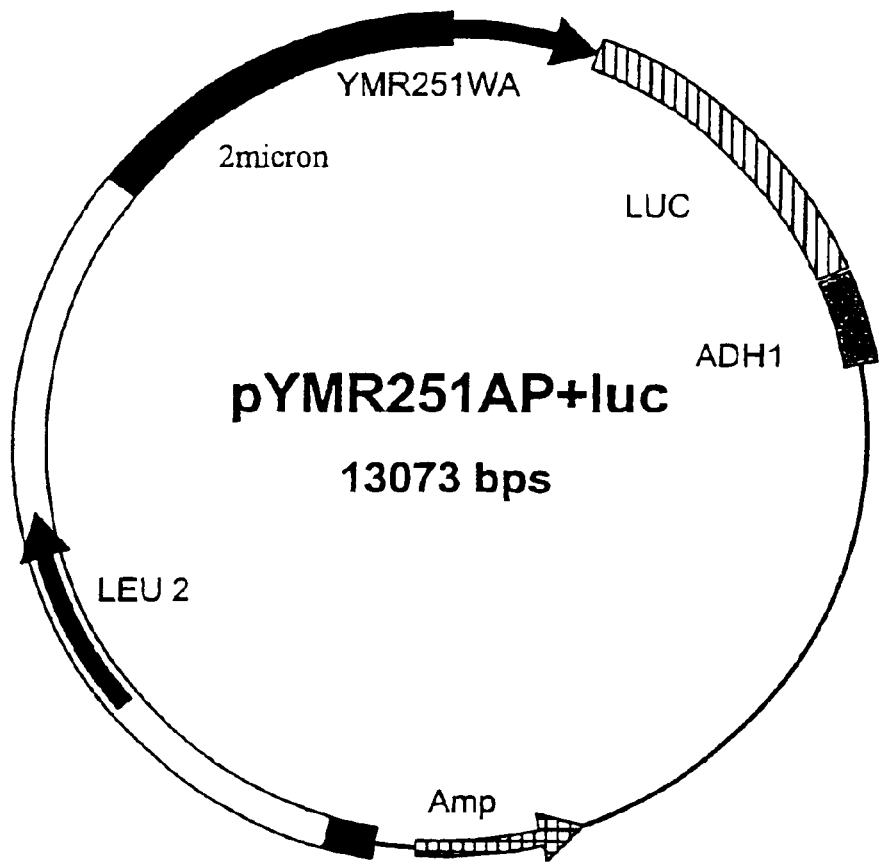
FIG. 6 is a is a map of pYMR251AP+luc.
Figure 7:
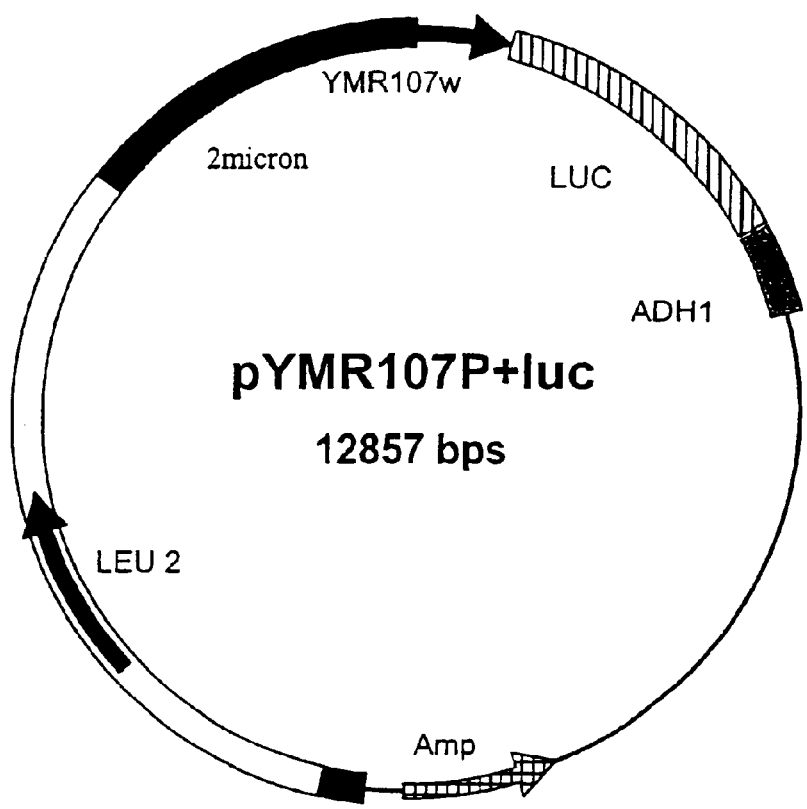
FIG. 7 is a map of pYMR107P+luc.
Figure 8:
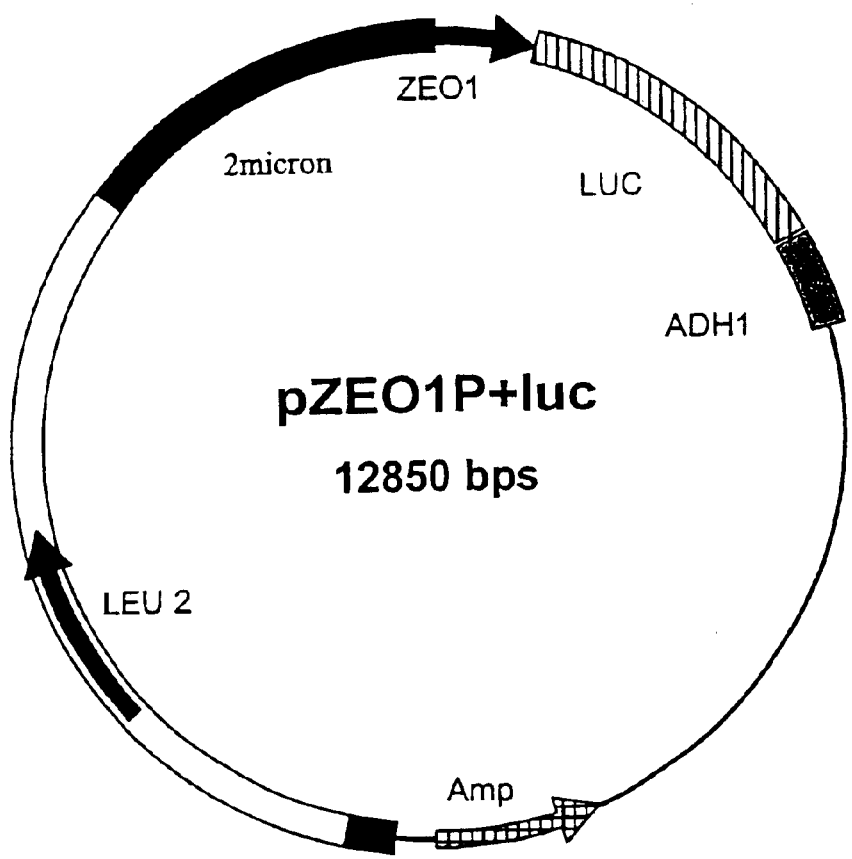
FIG. 8 is a map of pZEO1P+Iuc.

The PCR products representing the regions upstream of the YLR110C and YMR251W ORFs were cloned into the suitably digested YEp13-based multicopy yeast expression vector pPRB1P+luc. A map of YEp13 is shown in FIG. 1. The Accession number for YEp13 is U03498. A map of pPRB1P is shown in FIG. 2. The sequence of pPRB1P is shown in SEQ ID NO:27: A map of pPRB1P+luc is shown in FIG. 3 and the sequence is shown in SEQ ID NO:28. The PRB1 promoter was removed from the vector by digesting with the restriction enzymes HindIII/and NdeI. The digested backbone was then ligated wit a HindIII/NdeI digested PCR product. See FIG. 4.

The PCR products described below, and maxi-prepped pPRB1 P+luc were digested as follows. 60 µl of pPRB1+luc (328 µg/ml), 10 µl of Hind III (Life Technologies, cat.no. 5207-012, 10 units/µl), 10 µl NdeI (Amersham, cat.no. E0216Y, 20 units/µl), 10 µl NEBuffer 2 (NEB, cat no. 007-2), and 10 µl of H$_2$O 14 µl YLR110C, 2 µl of Hind III (Life Technologies cat.no. 15207-012, 10 units/µl Nde I (Amersham, cat.no. E0216Y, 20 units/µl), and 2 µl NEBuffer 2 (NEB, cat.no. 007-2). 14 µl YMR251WA, 2 µl of Hind III (Life Technologies, cat.no. 15207-012, 10 units/µl), 2 µl Nde I (Amersham, cat.no. E0216Y, 20 units/µl), and 2 µl NEBuffer 2 (NEB, cat.no. 007-2). The solutions were allowed to react at 37° C., for hours.

The (Double digested pPRB1P+luc backbone was purified on an LMP gel using Wizard PCR preps (Promega, cat. no. A7170), and then ethanol precipitated. The remaining digestion products were also ethanol precipitated. The pPBR1P+luc digests were resuspended in 60 µl of H$_2$O and the PCR product digests were resuspended in 20 µl.

Ligation reactions were then carried out between each promoter region and the digested pPRBP1+luc at 16° C. overnight. The PCR products representing the regions upstream o the following ORFs; YMR107W and ZEO1, were prepared, restricted, and ligated essentially as described above, however BCL restriction buffer B and different amounts of PCR product/volumes were used.

Transformation of Ligation Products into *E.coli*

The products of the ligations described above were transformed into *E. coli* (Invitrogen's One-Shot TOP10 Competent cells, cat.no. C4040-10) according to manufacturers protocol. In each case 5µl of the ligation product was added to the cell suspension. The total final cell suspension was plated out onto L-amp plates and incubated overnight at 37° C.

Colonies were picked from the plates and PCR screened using the PCR primers used to amplify the promoters originally. Two positive colonies from each ligation were grown in 5 ml overnight cultures and their plasmids were purified (Promega Wizard Plus SV Mini-preps, cat. no A1330). The eluted DNA was ethanol precipitated and resuspended in 20 µl of water. Analytical restriction digests were carried out to confirm the presence of the correct promoter. Clones containing all four promoter constructs were obtained.

The new constructs were named as follows:

| | |
|---|---|
| pPRB1 + luc backbone + YLR110C promoter = pYLR110P + luc | SEQ ID NO: 19 |
| pPRB1 + luc backbone + YMR251WA promoter = pYMR251AP + luc | SEQ ID NO: 20 |
| pPRB1 + luc backbone + YMR107W promoter = pYMR107P + luc | SEQ ID NO: 21 |
| pPRB1 + luc backbone + ZEO1 promoter = pZEO1P + luc | SEQ ID NO: 22 |

Map of pYLR110P+luc, pYMR251AP+luc, pYMR107P+luc, and pZEO1P+luc are shown in FIGS. 5, 6, 7, and 8, respectively. Plasmid DNA (pYLR110P+luc and pYMR251P+luc) was prepared for transformation into yeast and sequencing using the QIAGEN Plasmid Maxi kit (Cat.no. 12162). The DNA concentrations of the maxi-preps (measured by absorbance at 260 nm) were: pYLR110P+luc 463 µg/ml; pYMR251AP+luc 346 µg/ml; pYMR107P+luc ~300 µg/ml; and pZEO1P+luc ~720 µg/ml. The remaining plasmids were transformed into yeast as Wizard Plus SV Mini-prep DNA, and maxi-prep DNA was obtained for sequencing using the Gibco BRL Concert Plasmid Maxi kit (Cat no. 11452).

Sequencing of Promoter Constructs

DNA (of each of the four promoter constructs were sequenced using the ABI PRISM BigDye Terminator Cycle Sequencing Kit (PE Applied Biosystems, part no. 4303153) was used to carry out the sequencing reactions. Each reaction contained 8 µl of Reaction Mix and 1 µl of 3.2 µM. The volumes of template DNA and H$_2$O added are as follows: 1.1 µl of pYLR0P+luc template and 9.9 µl of water; 1.4 µl of pYMR251AP+luc template and 9.6µl of water; 2.0 6.0 µl of pYMR107P+luc template and 9.0-5.0 µl of water; and 0.5-1.5 µl of pZEO1P+luc template and 10.5-9.5 µl of water.

The thermocycling protocol is described in the ABI protocol, the PCR products were ethanol precipitated by adding 3M NaOAc and absolute Ethanol, standing at room temperature for 15 minutes, centrifuging for 20 minutes and washing with 250 µl of 70% ethanol. The precipitated DNA was resuspended in 3 µl of loading dye and 2 µl of each suspension as analyzed on an PE-AB 377 automated sequencer.

The following promoter constructs pYLR10P+luc and pYMR251AP+luc were each sequenced using four primers:

Yep 3 F2: CCTCAATTGGATTAGTCTCA-SEQ ID NO:13-aligns to the Yep13 backbone, 290 bp 5' of the Hind III site.

Luc R1: CACCTCGATATGTGCATCTG -SEQ ID NO:14-aligns to the Luc ORF, 150 bp 3' of the NdeI site.

Forward PCR primer: forward primer used to PCR clone promoter, i.e., SEQ ID) NO:5 and SEQ NO: 7.

Reverse PCR primer: reverse primer used to PCR clone promoter, i.e., SEQ ID NO:6 and SEQ ID 0:8.

The remaining promoter constructs (pYMR107P+luc and pZEO1P+luc)were each sequence using primers Yep 13 F2 and luc R1. Cobining the data from all primers completely sequenced the promoter regions and spanned the cloning sites of the original vector.

Deviations from Published Genomic Sequences

All sequences differ by a few base pairs around the ATG, this results from the creation of an NdeI site at the 3' end of the promoter. In addition, the following further alterations from published sequences were identified.

pYMR 107P+luc: In the initial construct (for which luciferase reporter data is described), a cloning artifact led to the junction between the promoter region and the LUC ORF in pYMR107W+luc to have the sequence: CATATATG (where ATG is the luciferase translational tart site). This sequence was modified by site directed mutagenesis to create the sequence CATATG, which generates a novel NdeI site at the promoter/luciferase junction. Subsequent luciferase expression analysis confirmed that expression from the NdeI site modified pYMR107P+luc construct did not differ significantly from the original construct, threfore the sequence of the corrected CATATG construct is included herein.

Other Modifications pYMR 107P+luc: Cloning artifacts created an additional HindIII site and linker to the 5' (ie., outside) of the Pymr107p+luc and promoters:

Instead of:

hindiIII NotI promoter 5'

AAGCTT-CGCGGCCGCG-NNNNNNN SEQ ID NO:17

The sequence is:

hind II hindIII NotI promoter 5'

AAGCTT-AGCT-AAGCTT-CGCGGCCGCG-NNNNNNN SEQ ID NO:18.

EXAMPLE 4

Luciferase Assays of Promoter Activity

Transformation of *S. cerevisiae* with Promoter Constructs.

*S. cerevisiae* strain 11C was transformed with five promoter constructs. This strain carries six metabolic markers, Ade, Trp, Ura, Lys, Leu and His. It has the genotype: ade2-161, trp1-D63, ura3-52, lys 2-801, leu2D1 &/or leu2-3 &/or leu2-112, hisD200 &/or his D200. 11C was generated by crossing the strains YPH500 (Mat a ura3-52 lys2-80 1 ade2-161 trp1-D63 hisD200 leu2D1) and AH22 (MATa leu2-3 leu2-112 his4-519 can1.

11C cell is were streaked from a glycerol stock onto a YPD plate and grown at 30° C. for two day . The cells were transformed with the five, plasmids, pYLR110P+luc, pYMR251AP+luc, pYMR107P+luc, & pZEO1P+luc and pPRB1P+luc to act as a control. The transformations were carried out using the Quick and Easy method (Gietz, R. D. and R. A. Woods 1994, *Molecular Genetics of Yeast: Practical Approaches* pp. 121–134. 10 ml of plasmid as added to the transformation mix in each case. The whole transformation mixes were plated out onto -Leu plates and incubated at 30° C. for three days. Three individual colonies from each transformation plate were picked and used to inoculate 10 ml YPD culture. The 10 ml cultures were incubated in an orbital shaker set to 200 rpm and 30° C. Cells ere harvested from the cultures at two points. First, at a point at which the OD of the culture was close to 1.0, at which time a 4 m1 sample was taken. Second, a 3 ml sample was taken after an incubation time of 45 hours. The ODs and incubation time of each sample is shown in Table 5. For all harvested samples, the cells were immediately spun down at 3000 rpm and 4° C., washed in 5 ml of dH$_2$O. repelleted and frozen at −20 C.

TABLE 5

| Plasmid | Clone number | OD at time of harvesting first 4 ml sample | Incubation time at harvesting of first sample (hours) | OD at time of harvesting second 3 ml sample |
|---|---|---|---|---|
| pPRB1P + luc | 7 | 0.98 | 24.5 | 4.80 |
| | 8 | 0.68 | 28 | 5.56 |
| | 9 | 1.15 | 28 | 5.66 |
| pYLR110P + luc | 8 | 1.12 | 28 | 5.50 |
| | 9 | 0.48 | 28 | 4.38 |
| | 10 | 1.16 | 24.5 | 5.51 |
| pYMR251AP + luc | 8 | 1.20 | 24.5 | 4.99 |
| | 9 | 1.05 | 27 | 4.71 |
| | 10 | 1.15 | 27 | 5.18 |
| pYMR107P + luc | 1 | 1.06 | 27 | 5.47 |
| | 2 | 0.49 | 28.5 | 4.54 |
| | 3 | 0.97 | 25.5 | 5.58 |
| pZE01P + luc | 1 | 1.02 | 28.5 | 4.84 |
| | 2 | 0.62 | 28.5 | 4.97 |
| | 3 | 0.42 | 28.5 | 4.31 |

Analysis of Luciferase Activity

All of the samples were analyzed for luciferase activity, using the LucLite Luciferase Reporter Gene Assay Kit (Packard, cat.no 6016911). The cells were prepared by resusspending in PBS and diluting to a final concentration of 6×10⁶ cells/ml. 100 ml of each cell suspension was pipetted into wells in duplicate on two 96 well plates, so that each well contained 6×10⁵ cells. The plates were incubated at 30° C. for 10 minutes. 100 ml of a 1 in 2 dilution of reconstituted substrate was added to each well, and the plate was further incubated at room temperature for 10 minutes. The luminescence was then measured using the Packard TopCount. The luminescence readings obtained after 0.03 min are shown below in counts per second (CPS) in Table 6.

EXAMPLE 5
Isolation of Active Promoter Fragments

Operative fragments of the YLR110C, YMR251WA, YMR107W and ZEO1 promoters can be generated using restriction endonucleases, 5' or 3' deletion mutagenesis, PCR, site specific deletion, or a combination thereof. For example, purified pYLR1P+luc, pYMR251AP+luc, pYMR107P+luc or pZEO1P+luc plasmids, as generated in Example 3, can be subjected to restriction endonucleases to generate fragments of the YLR110C, YMR251WA, YMR107W or ZEO1 promoters. Restriction endonuclease

TABLE 6

| Plasmid | Clone number | First sample Readings | (CPS) | Average | Average | Second sample Readings | (CPS) | Average | Average |
|---|---|---|---|---|---|---|---|---|---|
| pPRB1P + luc | 7 | 35890 | 35690 | 35790 | 34898 | 20322 | 20975 | 20648 | 19867 |
| | 8 | 25498 | 25276 | 25387 | 24495 | 52997 | 51778 | 52388 | 51607 |
| | 9 | 24137 | 27797 | 25967 | 25075 | 49192 | 46971 | 48081 | 47300 |
| pYLR110P + luc | 8 | 52354 | 53618 | 52986 | 52094 | 41789 | 38904 | 40346 | 39565 |
| | 9 | 105299 | 99776 | 102537 | 101645 | 85562 | 84468 | 85015 | 84234 |
| | 10 | 107531 | 109226 | 108379 | 107486 | 22507 | 22436 | 22471 | 21690 |
| PYM4251AP + luc | 8 | 71993 | 69797 | 70895 | 70003 | 40869 | 40202 | 40536 | 39755 |
| | 9 | 98853 | 98389 | 98621 | 97729 | 51159 | 49828 | 50493 | 49712 |
| | 10 | 83210 | 87546 | 85378 | 84485 | 70091 | 74576 | 72334 | 71553 |
| pYMR107P + luc | 1 | 9046 | 8650 | 8848 | 6790 | 29413 | 28505 | 28959 | 28124 |
| | 2 | 3996 | 4009 | 402 | 1945 | 24391 | 23915 | 24153 | 23318 |
| | 3 | 3018 | 3236 | 3127 | 1069 | 23866 | 23408 | 23637 | 22802 |
| pZE01P + luc | 1 | 64137 | 63162 | 63649 | 61592 | 47469 | 45769 | 46619 | 45784 |
| | 2 | 19579 | 18329 | 18954 | 16897 | 44910 | 42982 | 43946 | 43111 |
| | 3 | 87572 | 90317 | 88944 | 86887 | 142414 | 142262 | 142338 | 141503 |

TABLE 7

| Promoter | mRNA levels | Luciferase Expression Glucose | Luciferase Expression Ethanol |
|---|---|---|---|
| PRB1 | Ethanol Induced | 1.00 | 1.00 |
| YLR110C | Highly Ethanol and Glucose Induced | 3.03 | 1.22 |
| YMR251WA | Highly Ethanol and Glucose Induced | 2.92 | 1.35 |
| YMR107W | Ethanol Induced | 0.21 | 0.95 |
| ZEO1 | Very Highly Ethanol and Glucose Induced | 3.62 | 2.89 |

Three promoters give higher levels of expression than PRB1 at both ODs, these are: YLR110C, YMR251WA, and ZEO1. The promoter showing the greatest fold induction is YMR107W.

Creatine Vectors with Promoters but Without the Luciferase Gene

Figure 9:
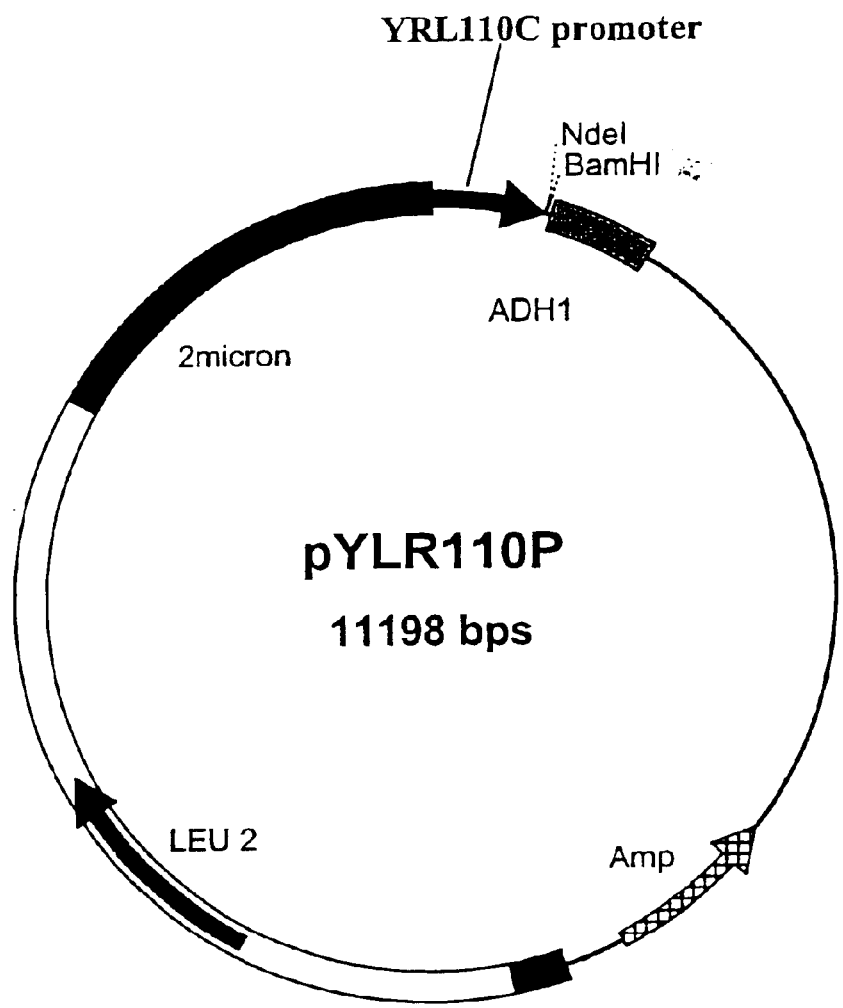
FIG. 9 is a map pYLR110P.
Figure 10:
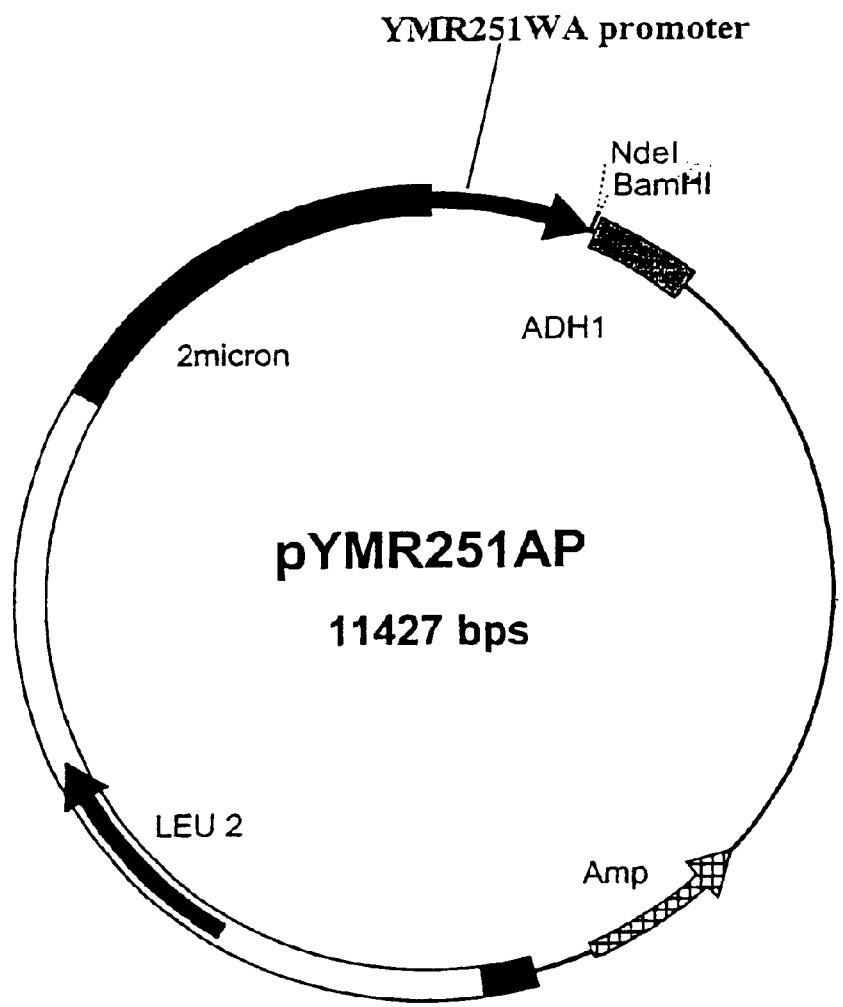
FIG. 10 is a map of pYMR251AP.
Figure 11:
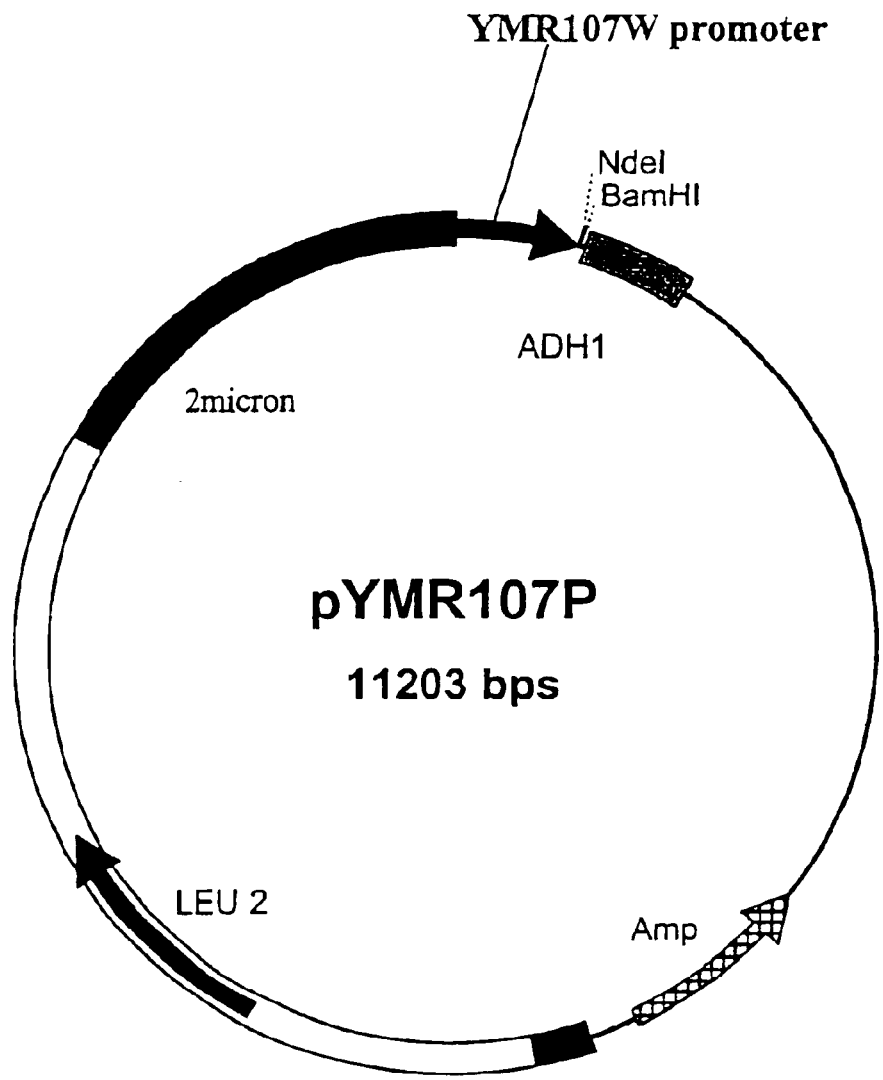
FIG. 11 is a map of pYMR107P.
Figure 12:
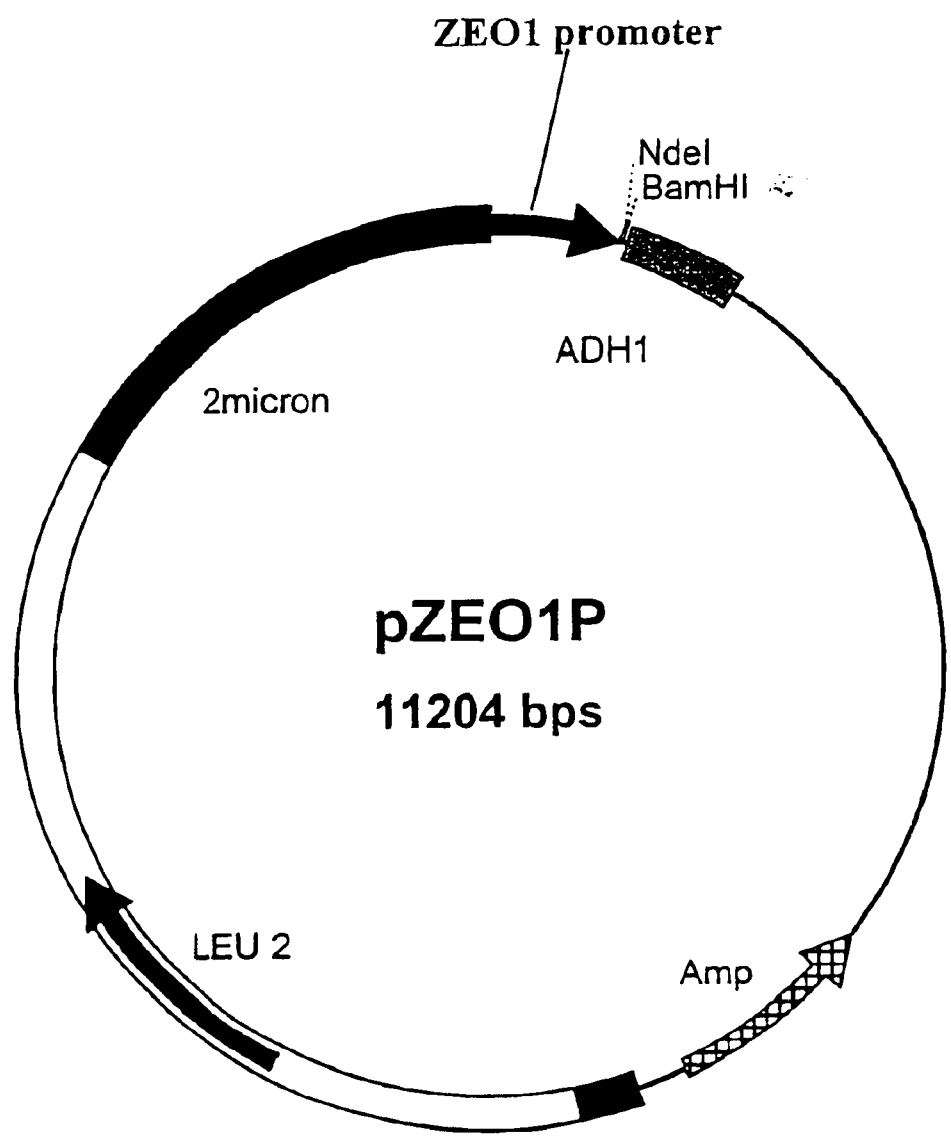
FIG. 12 is a mapo of pZEO1P.

Based on the analysis of luciferase expression four further promoter constructs have been made. The lack the luciferase gene and can be used to clone nucleic acid molecules encoding polypeptides of interest downstream of the promoters such that they drive expression of the nucleic molecules of interest. The sequences of these four plasmids are named: G1: pYLR110P (SEQ ID NO:23) (map at FIG. 9); G2: pYMR251AP (SEQ ID NO:24) (map at FIG. 10); G3 pYMR107P (SEQ ID NO:25) (map at FIG. 11); and G4: pZE1P (SEQ ID NO:26) (map at FIG. 12). These were constructed by digesting pPRB1P (SEQ ID NO:27) with HindIII and NdeI to obtain the vector. The promoter+luc construct was digested with HindIII and NdeI to obtain the promoter fragment. The vector and promoter DNA was purified from LMP agarose using PCRpreps. The vector and promoter was ligated and used to transform E. coli. Correct recombinants were screened for.

sites, preferably unique restriction endonuclease sites, within the promoter sequences shown in SEQ ID NO: 1, SEQ ID NO:2, SEQ ID NO:3, and SEQ ID NO:4 can be identified that generate fragments of the promoter upon restriction endonuclease digestion. Such fragments are preferably, 17, 25, 50, 75, 100, 150, 200, 250, 300, 350, 400, 450, 500, 550, 600, 650 or 700 nucleotides in length.

The fragments generated by restriction endonuclease digestion of the promoters shown in SEQ ID NO:1, SEQ ID NO:2, SEQ ID NO:3, or SEQ ID NO:4 can be separated by agarose gel electrophoresis. The agarose gel band corresponding to the desired promoter fragment can be cut out of the agarose gel. The fragment can be isolated and purified from the agarose gel by, for example, electroelution or kits such as QIAquick™ gel extraction kit or OIAEX® II Gel Extraction System (Qiagen Cat. No. 28704 and 20021).

The purified promoter fragment can be ligated into the isolated and purified HinduIII, NdeI, double-digested pPRBP1+luc backbone such that the promoter fragment is operably linked to a luciferase gene and transformed into E. coli, as described in Example 3. The new expression vector comprising a fragment of YLR110C, YMR251WA, YMR107W, or ZEO1 promoter region can be isolated and purified from E. coli, sequenced, and transformed into yeast as described in Example 3.

To analyze promoter activity, luciferase assays as described in Example 4, can be conducted using S. cerevisiae cultures that have been transformed with the expression vector comprising a fragment of the YLR110 C, YMR251WA, YMR107W, or ZEO1 promoter operably linked to a luciferase gene and S. cerevisiae cultures that have been transformed with pPRB1P+luc. The S. cerevisiae cultures are grown in medium containing a non-fermentable carbon source, such as ethanol, or a fermentable carbon source, such as glucose, or both. Cells are obtained from the cultures and analyzed for luciferase activity as described in Example 4.

A promoter fragment is operative if it expresses at least 75% of the luciferase activity as the PRB 1 promoter. Preferably, an operative promoter fragment expresses at least 100%, 200%, 300%, 400%, or more of the luciferase activity as the PRB1 promoter.

Brief Description of the Sequences

SEQ ID NO: 1 Polynucleotide sequence of promoter YLR110C
SEQ ID NO:2 Polynucleotide sequence of promoter YMR251WA
SEQ ID NO:3 Polynucleotide sequence of promoter YMR 107W
SEQ ID NO:4 Polynucleotide sequence of promoter ZEO1
SEQ ID NO:5 Forward PCR primer for YLR110C
SEQ ID NO:6 Reverse PCR primer for YLR110C
SEQ ID NO:7 Forward PCR primer for YMR251WA
SEQ ID NO:8 Reverse PCR primer for YMR251WA
SEQ ID NO:9 Forward PCR primer for YMR107W
SEQ ID NO:10 Reverse PCR primer for YMR107W
SEQ ID NO:11 Forward PCR primer for ZEO1
SEQ ID NO:12 Reverse PCR primer for ZEO1
SEQ ID NO:13: Yep13 Forward PCR primer
SEQ ID NO:14: Luc R1 Forward PCR primer
SEQ ID NO:15 Primer used in cDNA sequencing
SEQ ID NO:16 Control oligonucleotide used in Gene-Chip Microarray assay
SEQ ID NO:17 Original pYMR107P+luc sequence
SEQ ID NO:18 Modified pYMR107P+luc sequence
SEQ ID NO:19 Nucleotide sequence of pYLR110P+luc
SEQ ID NO:20 Nucleotide sequence of pYMR251AP+luc
SEQ ID NO:21 Nucleotide sequence of pYMR107P+luc
SEQ ID NO:22 Nucleotide sequence of pZEO1P+luc
SEQ ID NO.23 Nucleotide sequence of pYLR110P
SEQ ID NO:24 Nucleotide sequence of pYMR251AP
SEQ ID NO:25 Nucleotide sequence of pYMR107P
SEQ ID NO:26 Nucleotide sequence of pZEO1P
SEQ ID NO:27 Nucleotide sequence of pPRB1P
SEQ ID NO:28 Nucleotide sequence of pPRB1P+luc
SEQ ID NO:29 YLR110C promoter region
SEQ ID NO :30YMR251WA promoter region
SEQ ID NO:31 YMR107W promoter region
SEQ ID NO:32 ZEO1promoter region

What is claimed is:

1. An isolated and purified polynucleotide consisting of SEQ ID NO: 4, wherein the polynucleotide is operative as a promoter to express a nucleic acid molecule encoding a polypeptide when operably linked to said nucleic acid molecule.

2. A yeast expression vector comprising the polynucleotide of claim 1.

3. A yeast cell transformed with the yeast expression vector of claim 1.

4. A method for producing a polypeptide comprising the steps of:
   (a) constructing a yeast expression vector wherein a nucleic acid encoding the polypeptide is controlled by the polynucleotide of claim 1;
   (b) transforming a culture of yeast cells with the yeast expression vector;
   (c) maintaining the yeast cells in culture so that the polypeptide is expressed; and
   (d) recovering the polypeptide.

5. A method for producing a polypeptide comprising the steps of:
   (a) cloning a nucleic acid molecule encoding the polypeptide into an expression vector selected from the group consisting of pZEO1P+luc and pZEO1P, wherein the nucleic acid molecule is operably linked to a promoter of the expression vector;
   (b) transforming a culture of yeast cells with the yeast expression vector;
   (c) maintaining the yeast cells in culture so that the polypeptide is expressed; and
   (d) recovering the polypeptide.

6. A method for producing a polypeptide comprising the steps of:
   (a) constructing a yeast expression vector wherein a nucleic acid molecule encoding the polypeptide is controlled by the polynucleotide of claim 1;
   (b) transforming a culture of yeast calls with the yeast expression vector;
   (c) maintaining the yeast cells in culture medium and controlling the expression of the nucleic acid molecule encoding the polypeptide by varying the level of a torment able carbon source in the culture medium; and
   (d) recovering the polypeptide.

7. The method of claim 6 wherein the fermentable carbon source is glucose.

8. A method for producing a polypeptide comprising the steps of:
   (a) constructing a yeast expression vector wherein a nucleic acid molecule encoding the polypeptide is controlled by the polynucleotide of claim 1;
   (b) transforming a culture of yeast cells with the yeast expression vector;
   (c) maintaining tho yeast cells in culture medium and controlling the expression of the nucleic acid molecule encoding the polypeptide by varying the level of a non-fermentable carbon source in the culture medium; and
   (d) recovering the polypeptide.

9. The method of claim 8 wherein the non-fermentable carbon source is ethanol.

10. A method for producing a polypeptide comprising the steps of:
    (a) constructing a yeast expression vector wherein a nucleic acid molecule encoding the polypeptide is controlled by the polynucleotide of claim 1;
    (b) transforming a culture of yeast cells with the yeast expression vector;
    (c) maintaining the yeast cells in culture medium and controlling the expression of the nucleic acid molecule encoding the polypeptide by varying the level of a fermentable carbon source and a non-fermentable carbon source in the culture medium, and
    (d) recovering the polypeptide.

11. The method of claim 10 wherein the fermentable carbon source is glucose.

12. The method of claim 10 wherein the non-fermentable carbon source is ethanol.

* * * * *

UNITED STATES PATENT AND TRADEMARK OFFICE
CERTIFICATE OF CORRECTION

PATENT NO. : 6,716,601 B1
DATED : April 6, 2004
INVENTOR(S) : Belfield et al.

It is certified that error appears in the above-identified patent and that said Letters Patent is hereby corrected as shown below:

Column 135,
Line 22, please change "claim 1" to -- claim 2 --.

Signed and Sealed this

Twelfth Day of July, 2005

JON W. DUDAS
*Director of the United States Patent and Trademark Office*

SEQUENCE LISTING

```
<160> NUMBER OF SEQ ID NOS: 32

<210> SEQ ID NO 1
<211> LENGTH: 494
<212> TYPE: DNA
<213> ORGANISM: Saccharomyces cerevisiae

<400> SEQUENCE: 1
cgtctgattt  ccgttttggg  aatcctttgc  cgcgcgcccc  tctcaaaact  ccgcacaagt      60
cccagaaagc  gggaaagaaa  taaaacgcca  ccaaaaaaaa  aaaaataaaa  gccaatcctc     120
gaagcgtggg  tggtaggccc  tggattatcc  cgtacaagta  tttctcagga  gtaaaaaaac     180
cgtttgtttt  ggaattcccc  atttcgcggc  cacctacgcc  gctatctttg  caacaactat     240
ctgcgataac  tcagcaaatt  ttgcatattc  gtgttgcagt  attgcgataa  tgggagtctt     300
actcccaaca  taacggcaga  aagaaatgtg  agaaaatttt  gcatcctttg  cctccgttca     360
agtatataaa  gtcggcatgc  ttgataatct  ttctttccat  cctacattgt  tctaattatt     420
cttattctcc  tttattcttt  cctaacatac  caagaaatta  atcttctgtc  attcgcttaa     480
acactatatc  acat                                                          494

<210> SEQ ID NO 2
<211> LENGTH: 723
<212> TYPE: DNA
<213> ORGANISM: Saccharomyces cerevisiae

<400> SEQUENCE: 2
ctttcgatta  gcacgcacac  acatcacata  gactgcgtca  taaaaataca  ctacggaaaa      60
accataaaga  gcaaagcgat  acctacttgg  aaggaaaagg  agcacgcttg  taaggggat     120 gggggctaag  aagtcattca  ctttcttttc  ccttcgcggt  ccggacccgg  gacccctcct     180
ctccccgcac  gatttcttcc  tttcatatct  tccttttatt  cctatcccgt  tgaagcaacc     240
```

```
gcactatgac taaatggtgc tggacatctc catggctgtg acttgtgtgt atctcacagt    300
ggtaacggca ccgtggctcg gaaacggttc cttcgtgaca attctagaac agggctaca    360 gtctcgataa tagaataata agcgcatttt tgctagcgcc gccgcggcgc ccgtttccca    420 ataggaggc gcagtttatc ggcggagctc tacttcttcc tatttgggta agcccctttc    480
tgttttcggc cagtggttgc tgcaggctgc gccggagaac atagtgataa gggatgtaac    540
tttcgatgag agaattagca agcggaaaaa aactatggct agctgggagt tgttttcaa    600 tcatataaaa gggagaaatt gttgctcact atgtgacagt ttctgggacg tcttaacttt    660
tattgcagag gactatcaaa tcatacagat attgtcaaaa aaaaaaaga ctaataataa    720 cat                                                                 723

<210> SEQ ID NO 3
<211> LENGTH: 497
<212> TYPE: DNA
<213> ORGANISM: Saccharomyces cerevisiae

<400> SEQUENCE: 3
gcagaaatga tgaagggtgt tagcgccgtc cactgatgtg cctggtagtc atgatttacg     60
tataactaac acatcatgag gacggcggcg tcaccccaac gcaaaagagt gacttccctg    120
cgctttgcca aaacccatca tcgccatc tggctcctgg cagggcggtt gatggacatc    180
agccgcctcc cttaattgct aaagcctcca caaggcacaa ttaagcaata tttcgggaaa    240
gtacaccagt cagtttgcgc ttttatgact gggttctaag gtactagatg tgaagtagtg    300
gtgacagaat cagggagata agagggagca gggtggggta atgatgtgcg ataacaatct    360
tgcttggcta atcaccccca tatcttgtag tgagtatata aataggagcc tcccttccta    420
ttgcaactcc ataaaatttt tttttgtagc cacttctgta acaagataaa taaaaccaac    480
taatcgagat atcacat                                                  497

<210> SEQ ID NO 4
<211> LENGTH: 500
<212> TYPE: DNA
<213> ORGANISM: Saccharomyces cerevisiae

<400> SEQUENCE: 4
ggaggtctgc ttcacgagcg cggtgtgcgc ctagtattgc cccgacggtc cgggtgccta     60
tccctagatt tcgtcgtgcc ccgacccaaa tagttaaacg tgtggtttat gggtgcacca    120
gggctttatc gtgttttata tcgatggcga tttgtgcctc cagtgtattt ttgtatatcc    180
aattaaggtt tcttacctaa ttttatttttt atcatcttta gttaatgctg gtttgctctg    240
tttctgctgc tttctgtgcg gttctcctct tctcttgttt cttcgtgttg tccccatcg    300 ccgatgggct tatatggcgt atatatatag agcgagtttt tacgtcgaag atcatctcag    360
tttgcttgat agcctttcta ctttattact ttcgttttta acctcattat actttagttt    420
tctttgatcg gttttttttct ctgtatactt aaaagttcaa atcaaagaaa catacaaaac    480
tacgtttata tcaattacat                                               500

<210> SEQ ID NO 5
<211> LENGTH: 35
<212> TYPE: DNA
<213> ORGANISM: Saccharomyces cerevisiae

<400> SEQUENCE: 5
atgcaagctt cgcggccgcc gtctgatttc cgttt                               35
```

```
<210> SEQ ID NO 6
<211> LENGTH: 30
<212> TYPE: DNA
<213> ORGANISM: Saccharomyces cerevisiae

<400> SEQUENCE: 6
ccaggccgca tatgtcatat agtgtttaag                                    30

<210> SEQ ID NO 7
<211> LENGTH: 37
<212> TYPE: DNA
<213> ORGANISM: Saccharomyces cerevisiae

<400> SEQUENCE: 7
agctaagctt cgcggccgcc tttcgattag cacgcac                            37

<210> SEQ ID NO 8
<211> LENGTH: 27
<212> TYPE: DNA
<213> ORGANISM: Saccharomyces cerevisiae

<400> SEQUENCE: 8
agataccttc atatgttatt attagtc                                       27

<210> SEQ ID NO 9
<211> LENGTH: 35
<212> TYPE: DNA
<213> ORGANISM: Saccharomyces cerevisiae

<400> SEQUENCE: 9
agctaagctt cgcggccgcg cagaaatgat gaagg                              35

<210> SEQ ID NO 10
<211> LENGTH: 29
<212> TYPE: DNA
<213> ORGANISM: Saccharomyces cerevisiae

<400> SEQUENCE: 10
atccatccca tatgtgatat ctcgattag                                     29

<210> SEQ ID NO 11
<211> LENGTH: 35
<212> TYPE: DNA
<213> ORGANISM: Saccharomyces cerevisiae

<400> SEQUENCE: 11
agctaagctt cgcggccgcg gaggtctgct tcacg                              35

<210> SEQ ID NO 12
<211> LENGTH: 29
<212> TYPE: DNA
<213> ORGANISM: Saccharomyces cerevisiae

<400> SEQUENCE: 12
tacgatcgca tatgtaattg atataaacg                                     29

<210> SEQ ID NO 13
<211> LENGTH: 20
<212> TYPE: DNA
<213> ORGANISM: Saccharomyces cerevisiae

<400> SEQUENCE: 13
```

-continued

```
cctcaattgg attagtctca                                          20

<210> SEQ ID NO 14
<211> LENGTH: 20
<212> TYPE: DNA
<213> ORGANISM: Saccharomyces cerevisiae

<400> SEQUENCE: 14
cacctcgata tgtgcatctg                                          20

<210> SEQ ID NO 15
<211> LENGTH: 63
<212> TYPE: DNA
<213> ORGANISM: Saccharomyces cerevisiae

<400> SEQUENCE: 15
ggccagtgaa ttgtaatacg actcactata gggaggcggt tttttttttt ttttttttt  60 ttt                                                            63

<210> SEQ ID NO 16
<211> LENGTH: 20
<212> TYPE: DNA
<213> ORGANISM: Saccharomyces cerevisiae

<400> SEQUENCE: 16
gtcaagatgc taccgttcag                                          20

<210> SEQ ID NO 17
<211> LENGTH: 23
<212> TYPE: DNA
<213> ORGANISM: Saccharomyces cerevisiae
<220> FEATURE:
<221> NAME/KEY: unsure
<222> LOCATION: (17)..(23)
<223> OTHER INFORMATION: The symbol "n" at positions 17 to 23 represents
      any nucleotide.

<400> SEQUENCE: 17
aagcttcgcg gccgcgnnnn nnn                                      23

<210> SEQ ID NO 18
<211> LENGTH: 33
<212> TYPE: DNA
<213> ORGANISM: Saccharomyces cerevisiae
<220> FEATURE:
<221> NAME/KEY: unsure
<222> LOCATION: (27)..(33)
<223> OTHER INFORMATION: The symbol "n" at positions 27 to 33 represents
      any nucleotide.

<400> SEQUENCE: 18
aagcttagct aagcttcgcg gccgcgnnnn nnn                           33

<210> SEQ ID NO 19
<211> LENGTH: 12844
<212> TYPE: DNA
<213> ORGANISM: Saccharomyces cerevisiae

<400> SEQUENCE: 19
aagcttcgcg gccgccgtct gatttccgtt tgggaatcc tttgccgcgc gccctctca   60 aaactccgca caagtcccag aaagcgggaa agaaataaaa cgccaccaaa aaaaaaaaa  120 taaaagccaa tcctcgaagc gtgggtggta ggccctggat tatcccgtac aagtatttct  180
caggagtaaa aaaaccgttt gttttggaat tccccatttc gcggccacct acgccgctat  240
```

```
ctttgcaaca actatctgcg ataactcagc aaattttgca tattcgtgtt gcagtattgc    300
gataatggga gtcttacttc aacataacg gcagaaagaa atgtgagaaa attttgcatc     360
ctttgcctcc gttcaagtat ataaagtcgg catgcttgat aatctttctt tccatcctac    420
attgttctaa ttattcttat tctcctttat tctttcctaa cataccaaga aattaatctt    480
ctgtcattcg cttaaacact atatcacata tggaagacgc caaaaacata agaaaggcc     540 cggcgccatt ctatccgctg aagatggaa ccgctggaga gcaactgcat aaggctatga    600
agagatacgc cctggttcct ggaacaattg cttttacaga tgcacatatc gaggtggaca    660
tcacttacgc tgagtacttc gaaatgtccg ttcggttggc agaagctatg aaacgatatg    720
ggctgaatac aaatcacaga atcgtcgtat gcagtgaaaa ctctcttcaa ttctttatgc    780
cggtgttggg cgcgttattt atcggagttg cagttgcgcc cgcgaacgac atttataatg    840
aacgtgaatt gctcaacagt atgggcattt cgcagcctac cgtggtgttc gtttccaaaa    900 agggggttgca aaaattttg aacgtgcaaa aaagctccc aatcatccaa aaaattatta    960
tcatggattc taaaacggat taccagggat ttcagtcgat gtacacgttc gtcacatctc   1020
atctacctcc cggttttaat gaatacgatt ttgtgccaga gtccttcgat agggacaaga   1080
caattgcact gatcatgaac tcctctggat ctactggtct gcctaaaggt gtcgctctgc   1140
ctcatagaac tgcctgcgtg agattctcgc atgccagaga tcctatttt ggcaatcaaa    1200 tcattccgga tactgcgatt ttaagtgttg ttccattcca tcacggtttt ggaatgttta   1260
ctacactcgg atatttgata tgtggatttc gagtcgtctt aatgtataga tttgaagaag   1320
agctgtttct gaggagcctt caggattaca agattcaaag tgcgctgctg gtgccaaccc   1380
tattctcctt cttcgccaaa agcactctga ttgacaaata cgatttatct aatttacacg   1440
aaattgcttc tggtggcgct cccctctcta aggaagtcgg ggaagcggtt gccaagaggt   1500
tccatctgcc aggtatcagg caaggatatg gctcactga gactacatca gctattctga   1560
ttacacccga gggggatgat aaaccgggcg cggtcggtaa agttgttcca ttttttgaag   1620
cgaaggttgt ggatctggat accgggaaaa cgctgggcgt taatcaaaga ggcgaactgt   1680
gtgtgagagg tcctatgatt atgtccggtt atgtaaacaa tccggaagcg accaacgcct   1740
tgattgacaa ggatggatgg ctacattctg gagacatagc ttactgggac gaagacgaac   1800
acttcttcat cgttgaccgc ctgaagtctc tgattaagta caaaggctat caggtggctc   1860
ccgctgaatt ggaatccatc ttgctccaac accccaacat cttcgacgca ggtgtcgcag   1920
gtcttcccga cgatgacgcc ggtgaacttc ccgccgccgt tgttgttttg gagcacggaa   1980
agacgatgac ggaaaaagag atcgtggatt acgtcgccat tcaagtaaca accgcgaaaa   2040
agttgcgcgg aggagttgtg tttgtggacg aagtaccgaa aggtcttacc ggaaaactcg   2100
acgcaagaaa aatcagagag atcctcataa aggccaagaa gggcggaaag atcgccgtgt   2160
aattggatcc agtttaaaca gtagctttgg acttcttcgc cagaggtttg gtcaagtctc   2220
caatcaaggt tgtcggcttg tctaccttgc agaaattta cgaaagatg gaaagggtc    2280 aaatcgttgg tagatacgtt gttgacactt ctaataagc gaatttctta tgatttatga   2340 ttttattat taaataagtt ataaaaaaa taagtgtata caaattttaa agtgactctt   2400
aggttttaaa acgaaaattc ttgttcttga gtaactcttt cctgtaggtc aggttgcttt   2460
ctcaggtata gcatgaggtc gctcttattg accacacctc taccggcatg ccagcaaat   2520 gcctgcaaat cgctccccat ttcacccaat tgtagatatg ctaactccag caatgagttg   2580
```

| | |
|---|---|
| atgaatctcg gtgtgtattt tatgtcctca gaagacaaca cctgttgtaa tcgttcttcc | 2640 |
| acacggatcg cggccgcttg atcctctacg ccggacgcat cgtggccggc atcaccggcg | 2700 |
| ccacaggtgc ggttgctggc gcctatatcg ccgacatcac cgatggggaa gatcgggctc | 2760 |
| gccacttcgg gctcatgagc gcttgtttcg gcgtgggtat ggtggcaggc cccgtggccg | 2820 |
| ggggactgtt gggcgccatc tccttgcatg caccattcct tgcggcggcg gtgctcaacg | 2880 |
| gcctcaacct actactgggc tgcttcctaa tgcaggagtc gcataaggga gagcgtcgac | 2940 |
| cgatgccctt gagagccttc aacccagtca gctccttccg gtgggcgcgg ggcatgacta | 3000 |
| tcgtcgccgc acttatgact gtcttcttta tcatgcaact cgtaggacag gtgccggcag | 3060 |
| cgctctgggt cattttcggc gaggaccgct ttcgctggag cgcgacgatg atcggcctgt | 3120 |
| cgcttgcggt attcggaatc ttgcacgccc tcgctcaagc cttcgtcact ggtcccgcca | 3180 |
| ccaaacgttt cggcgagaag caggccatta tcgccggcat ggcggccgac gcgctgggct | 3240 |
| acgtcttgct ggcgttcgcg acgcgaggct ggatggcctt ccccattatg attcttctcg | 3300 |
| cttccggcgg catcgggatg cccgcgttgc aggccatgct gtccaggcag gtagatgacg | 3360 |
| accatcaggg acagcttcaa ggatcgctcg cggctcttac cagcctaact tcgatcactg | 3420 |
| gaccgctgat cgtcacggcg atttatgccc cctcggcgag cacatggaac gggttggcat | 3480 |
| ggattgtagg cgccgcccta taccttgtct gcctccccgc gttgcgtcgc ggtgcatgga | 3540 |
| gccgggccac ctcgacctga atggaagccg gcggcaccts gctaacggat tcaccactcc | 3600 |
| aagaattgga gccaatcaat tcttgcggag aactgtgaat gcgcaaacca accottggca | 3660 |
| gaacatatcc atcgcgtccg ccatctccag cagccgcacg cggcgcatct cgggcagcgt | 3720 |
| tgggtcctgg ccacgggtgc gcatgatcgt gctcctgtcg ttgaggaccc ggctaggctg | 3780 |
| gcggggttgc cttactggtt agcagaatga atcaccgata cgcgagcgaa cgtgaagcga | 3840 |
| ctgctgctgc aaaacgtctg cgacctgagc aacaacatga atggtcttcg gtttccgtgt | 3900 |
| ttcgtaaagt ctggaaacgc ggaagtcagc gccctgcacc attatgttcc ggatctgcat | 3960 |
| cgcaggatgc tgctggctac cctgtggaac acctacatct gtattaacga agcgctggca | 4020 |
| ttgaccctga gtgatttttc tctggtcccg ccgcatccat accgccagtt gtttaccctc | 4080 |
| acaacgttcc agtaaccggg catgttcatc atcagtaacc cgtatcgtga gcatcctctc | 4140 |
| tcgtttcatc ggtatcatta cccccatgaa cagaaattcc cccttacacg gaggcatcaa | 4200 |
| gtgaccaaac aggaaaaaac cgcccttaac atggcccgct ttatcagaag ccagacatta | 4260 |
| acgcttctgg agaaactcaa cgagctggac gcggatgaac aggcagacat ctgtgaatcg | 4320 |
| cttcacgacc acgctgatga gctttaccgc agctgcctcg cgcgtttcgg tgatgacggt | 4380 |
| gaaaacctct gacacatgca gctcccggag acggtcacag cttgtctgta agcggatgcc | 4440 |
| gggagcagac aagcccgtca gggcgcgtca gcggtgttg gcgggtgtcg gggcgcagcc | 4500 |
| atgacccagt cacgtagcga tagcggagtg tatactggct taactatgcg gcatcagagc | 4560 |
| agattgtact gagagtgcac gatatccggt gtgaaatacc gcacagatgc gtaaggagaa | 4620 |
| aataccgcat caggcgctct tccgcttcct cgctcactga ctcgctgcgc tcggtcgttc | 4680 |
| ggctgcggcg agcggtatca gctcactcaa aggcggtaat acggttatcc acagaatcag | 4740 |
| gggataacgc aggaaagaac atgtgagcaa aaggccagca aaaggccagg aaccgtaaaa | 4800 |
| aggccgcgtt gctggcgttt ttccataggc tccgcccccc tgacgagcat cacaaaaatc | 4860 |
| gacgctcaag tcagaggtgg cgaaacccga caggactata aagataccag gcgtttcccc | 4920 |
| ctggaagctc cctcgtgcgc tctcctgttc cgaccctgcc gcttaccgga tacctgtccg | 4980 |

```
cctttctccc ttcgggaagc gtggcgcttt ctcaatgctc acgctgtagg tatctcagtt    5040
cggtgtaggt cgttcgctcc aagctgggct gtgtgcacga accccccgtt cagcccgacc    5100
gctgcgcctt atccggtaac tatcgtcttg agtccaaccc ggtaagacac gacttatcgc    5160
cactggcagc agccactggt aacaggatta gcagagcgag gtatgtaggc ggtgctacag    5220
agttcttgaa gtggtggcct aactacggct acactagaag gacagtattt ggtatctgcg    5280
ctctgctgaa gccagttacc ttcggaaaaa gagttggtag ctcttgatcc ggcaaacaaa    5340
ccaccgctgg tagcggtggt ttttttgttt gcaagcagca gattacgcgc agaaaaaaag    5400
gatctcaaga agatcctttg atcttttcta cggggtctga cgctcagtgg aacgaaaact    5460
cacgttaagg gattttggtc atgagattat caaaaaggat cttcacctag atccttttaa    5520
attaaaaatg aagttttaaa tcaatctaaa gtatatatga gtaaacttgg tctgacagtt    5580
accaatgctt aatcagtgag gcacctatct cagcgatctg tctatttcgt tcatccatag    5640
ttgcctgact ccccgtcgtg tagataacta cgatacggga gggcttacca tctggcccca    5700
gtgctgcaat gataccgcga gacccacgct caccggctcc agatttatca gcaataaacc    5760
agccagccgg aagggccgag cgcagaagtg gtcctgcaac tttatccgcc tccatccagt    5820
ctattaattg ttgccgggaa gctagagtaa gtagttcgcc agttaatagt ttgcgcaacg    5880
ttgttgccat tgctgcaggc atcgtggtgt cacgctcgtc gtttggtatg gcttcattca    5940
gctccggttc ccaacgatca aggcgagtta catgatcccc catgttgtgc aaaaaagcgg    6000
ttagctcctt cggtcctccg atcgttgtca gaagtaagtt ggccgcagtg ttatcactca    6060
tggttatggc agcactgcat aattctctta ctgtcatgcc atccgtaaga tgcttttctg    6120
tgactggtga gtactcaacc aagtcattct gagaatagtg tatgcggcga ccgagttgct    6180
cttgcccggc gtcaacacgg gataataccg cgccacatag cagaacttta aaagtgctca    6240
tcattggaaa acgttcttcg ggcgaaaac tctcaaggat cttaccgctg ttgagatcca    6300
gttcgatgta acccactcgt gcacccaact gatcttcagc atcttttact ttcaccagcg    6360
tttctgggtg agcaaaaaca ggaaggcaaa atgccgcaaa aaagggaata agggcgacac    6420
ggaaatgttg aatactcata ctcttccttt tcaatatta ttgaagcatt tatcagggtt    6480
attgtctcat gagcggatac atatttgaat gtatttagaa aaataaacaa ataggggttc    6540
cgcgcacatt tccccgaaaa gtgccacctg acgtctaaga aaccattatt atcatgacat    6600
taacctataa aaataggcgt atcacgaggc cctttcgtct tcaagaattc cacggactat    6660
agactatact agtatactcc gtctactgta cgatacactt ccgctcaggt ccttgtcctt    6720
taacgaggcc ttaccactct tttgttactc tattgatcca gctcagcaaa ggcagtgtga    6780
tctaagattc tatcttcgcg atgtagtaaa actagctaga ccgagaaaga gactagaaat    6840
gcaaaaggca cttctacaat ggctgccatc attattatcc gatgtgacgc tgcagaagca    6900
gaaatacacg cggtcagtga agctattccg ctattgaata acctcagtca ccttgtgcaa    6960
gaacttaaca agaaaccaat tattaaaggc ttacttactg atagtagatc aacgatcagt    7020
ataattaagt ctacaaatga agagaaattt agaaacagat tttttggcac aaaggcaatg    7080
agacttagag atgaagtatc aggtaataat ttatacgtat actacatcga gaccaagaag    7140
aacattgctg atgtgatgac aaaacctctt ccgataaaaa catttaaact attaactaac    7200
aaatggattc attagatcta ttacattatg ggtggtatgt tggaataaaa atcaactatc    7260
atctactaac tagtatttac gttactagta tattatcata tacggtgtta agagatgacg    7320
```

-continued

```
caaatgatga gaaatagtca tctaaattag tggaagctga aacgcaagga ttgataatgt    7380
aataggatca atgaatatta acatataaaa tgatgataat aatatttata gaattgtgta    7440
gaattgcaga ttccctttta tggattccta atcctcgag gagaacttct agtatatcta    7500
catacctaat attattgcct tattaaaaat ggaatcccaa caattacatc aaaatccaca    7560
ttctcttcaa atcaattgt cctgtacttc cttgttcatg tgtgttcaaa acgttatat    7620
ttataggata attatactct atttctcaac aagtaattgg ttgtttggcc gagcggtcta    7680
aggcgcctga ttcaagaaat atcttgaccg cagttaactg tgggaatact caggtatcgt    7740
aagatgcaag agttcgaatc tcttagcaac cattattttt ttcctcaaca taacgagaac    7800
acacaggggc gctatcgcac agaatcaaat tcgatgactg gaattttttt gttaatttca    7860
gaggtcgcct gacgcatata ccttttttcaa ctgaaaaatt gggagaaaaa ggaaaggtga    7920
gagccgcgga accggctttt catatagaat agagaagcgt tcatgactaa atgcttgcat    7980
cacaatactt gaagttgaca atattattta aggacctatt gttttttcca ataggtggtt    8040
agcaatcgtc ttacttttcta acttttctta cctttacat ttcagcaata tatatata    8100
tatttcaagg ataaccatt ctaatgtctg ccctaagaa gatcgtcgtt ttgccaggtg    8160
accacgttgg tcaagaaatc acagccgaag ccattaaggt tcttaaagct atttctgatg    8220
ttcgttccaa tgtcaagttc gatttcgaaa atcatttaat tggtggtgct gctatcgatg    8280
ctacaggtgt cccacttcca gatgaggcgc tggaagcctc caagaaggtt gatgccgttt    8340
tgttaggtgc tgtgggtggt cctaaatggg gtaccggtag tgttagacct gaacaaggtt    8400
tactaaaaat ccgtaaagaa cttcaattgt acgccaactt aagaccatgt aactttgcat    8460
ccgactctct tttagactta tctccaatca agccacaatt tgctaaaggt actgacttcg    8520
ttgttgtcag agaattagtg ggaggtatt actttggtaa gagaaaggaa gacgatggtg    8580
atggtgtcgc ttgggatagt gaacaataca ccgttccaga agtgcaaaga atcacaagaa    8640
tggccgcttt catggcccta caacatgagc caccattgcc tatttggtcc ttggataaag    8700
ctaatgtttt ggcctcttca agattatgga gaaaactgt ggaggaaacc atcaagaacg    8760
aattccctac attgaaggtt caacatcaat tgattgattc tgccgccatg atcctagtta    8820
agaacccaac ccacctaaat ggtattataa tcaccagcaa catgttttgg t gatatcatct    8880
ccgatgaagc ctccgttatc ccaggttcct tgggtttgtt gccatctgcg tccttggcct    8940
ctttgccaga caagaacacc gcatttggtt tgtacgaacc atgccacggt tctgctccag    9000
atttgccaaa gaataaggtc aaccctatcg ccactatctt gtctgctgca atgatgttga    9060
aattgtcatt gaacttgcct gaagaaggta aggccattga agatgcagtt aaaaaggttt    9120
tggatgcagg tatcagaact ggtgatttag gtggttccaa cagtaccacg gaagtcggtg    9180
atgctgtcgc cgaagaagtt aagaaaatcc ttgcttaaaa agattctctt tttttatgat    9240
atttgtacat aaactttata atgaaattc ataatagaaa cgacacgaaa ttacaaaatg    9300
gaatatgttc ataggtaga cgaaactata tacgcaatct acatacattt atcaagaagg    9360
agaaaaagga ggatgtaaag gaatacaggt aagcaaattg atactaatgg ctcaacgtga    9420
taaggaaaaa gaattgcact ttaacattaa tattgacaag gaggagggca ccacacaaaa    9480
agttaggtgt aacagaaaat catgaaacta tgattcctaa tttatatatt ggaggatttt    9540
ctctaaaaaa aaaaaaatac aacaaataaa aaacactcaa tgacctgacc atttgatgga    9600
gtttaagtca ataccttctt gaaccatttc ccataatggt gaaagttccc tcaagaattt    9660
tactctgtca gaaacggcct taacgacgta gtcgacctcc tcttcagtac taaatctacc    9720
```

-continued

```
aataccaaat ctgatggaag aatgggctaa tgcatcatcc ttacccagcg catgtaaaac   9780
ataagaaggt tctagggaag cagatgtaca ggctgaaccc gaggataatg cgatatccct   9840
tagtgccatc aataaagatt ctccttccac gtaggcgaaa gaaacgttaa cacaccctgg   9900
ataacgatga tctggagatc cgttcaacgt ggtatgttca gcggataata gacctttgac   9960
taatttatcg gatagtcttt tgatgtgagc ttggtcgttg tcaaattctt tcttcatcaa  10020
tctcgcagct tcaccaaatc ccgctaccaa tggggggggcc aaagtaccag atctcaatcc  10080
tctctcttgg ccaccaccgg atagtaaagg ttctaatcta actcttggtc tccttcttac  10140
atagatggca cctattccct ttggaccgta atcttgtga gaagaaattg atagtaaatc  10200
aatgttcatt tcattgacat caatgtgaat cttaccatag gcttgtgcgg cgtcagtatg  10260
aaagtagatc ttattctttc tacaaattgc accaatttct ttaataggtt gaatgacacc  10320
gatttcatta ttgacagcca tcacagagac gagacaggta tctggtctaa tggcatcttc  10380
caattccttc aaatcgataa gaccttgatc gtccacattt aggaaagtga cttcaaatcc  10440
ctccttcatc atggcccgtg cggcttccaa gacacacttg tgttccgttc tagtggtgat  10500
gatgtgtttc ttagtcttct tataaaatct tgggacaccc ttaagaacca tattattaga  10560
ttcggtcgct cccgaagtga atattattc cttggggtcg gcattgatca tctttgctac  10620
gtaagctcta gcattttcca cagcagtatt tgtttcccaa ccgtaagagt gagtgttgga  10680
atgaggatta ccataaagtc ccgtataaaa cttcaacatc gtatccaaaa ccctagggtc  10740
tgttggtgta gtggcttgca tgtcaagata tatgggacga gtaccaaaac ctgtgttttc  10800
ttgataagca tggctcattg cagtgctacc agaagctact acagcatctg gggtggtacc  10860
ggatgcactc gcacgggcac tagcctgtgc ctttgcagca gcctgaatat cggtatgcgt  10920
ttccagagag aagttgtcgt ctaacttcac gcctgctgca gtctcaatga tattcgaata  10980
cgctttgagg agatacagcc taatatccga caaactgttt tacagattta cgatcgtact  11040
tgttacccat cattgaattt tgaacatccg aacctgggag ttttccctga aacagatagt  11100
atatttgaac ctgtataata atatatagtc tagcgcttta cggaagacaa tgtatgtatt  11160
tcggttcctg gagaaactat tgcatctatt gcataggtaa tcttgcacgt cgcatccccg  11220
gttcattttc tgcgtttcca tcttgcactt caatagcata tctttgttaa cgaagcatct  11280
gtgcttcatt ttgtagaaca aaaatgcaac gcgagagcgc taattttca aacaaagaat  11340
ctgagctgca tttttacaga acagaaatgc aacgcgaaag cgctattta ccaacgaaga  11400
atctgtgctt cattttgta aaacaaaaat gcaacgcgag agcgctaatt tttcaaacaa  11460
agaatctgag ctgcatttt acagaacaga atgcaacgc gagagcgcta ttttaccaac  11520
aaagaatcta tacttctttt ttgttctaca aaaatgcatc ccgagagcgc tattttctta  11580
acaaagcatc ttagattact tttttctcc tttgtgcgct ctataatgca gtctcttgat  11640
aactttttgc actgtaggtc cgttaaggtt agaagaaggc tactttggtg tctattttct  11700
cttccataaa aaaagcctga ctccacttcc cgcgttact gattactagc gaagctgcgg  11760
gtgcattttt tcaagataaa ggcatccccg attatattct ataccgatgt ggattgcgca  11820
tactttgtga acagaaagtg atagcgttga tgattcttca ttggtcagaa aattatgaac  11880
ggtttcttct attttgtctc tatatactac gtataggaaa tgtttacatt tcgtattgt  11940
tttcgattca ctctatgaat agttcttact acaattttt tgtctaaaga gtaatactag  12000
agataaacat aaaaaatgta gaggtcgagt ttagatgcaa gttcaaggag cgaaaggtgg  12060
```

-continued

| | |
|---|---|
| atgggtaggt tatataggga tatagcacag agatatatag caaagagata cttttgagca | 12120 |
| atgtttgtgg aagcggtatt cgcaatattt tagtagctcg ttacagtccg gtgcgttttt | 12180 |
| ggttttttga aagtgcgtct tcagagcgct tttggttttc aaaagcgctc tgaagttcct | 12240 |
| atactttcta gagaatagga acttcggaat aggaacttca aagcgtttcc gaaaacgagc | 12300 |
| gcttccgaaa atgcaacgcg agctgcgcac atacagctca ctgttcacgt cgcacctata | 12360 |
| tctgcgtgtt gcctgtatat atatatacat gagaagaacg gcatagtgcg tgtttatgct | 12420 |
| taaatgcgta cttatatgcg tctatttatg taggatgaaa ggtagtctag tacctcctgt | 12480 |
| gatattatcc cattccatgc ggggtatcgt atgcttcctt cagcactacc ctttagctgt | 12540 |
| tctatatgct gccactcctc aattggatta gtctcatcct tcaatgctat catttccttt | 12600 |
| gatattcgat cctaggcata gtaccgagaa actagtgcga agtagtgatc aggtattgct | 12660 |
| gttatctgat gagtatacgt tgtcctggcc acggcagaag cacgcttatc gctccaattt | 12720 |
| cccacaacat tagtcaactc cgttaggccc ttcattgaaa gaaatgaggt catcaaatgt | 12780 |
| cttccaatgt gagattttgg gccattttt atagcaaaga ttgaataagg cgcattttc | 12840 |
| ttca | 12844 |

<210> SEQ ID NO 20
<211> LENGTH: 13073
<212> TYPE: DNA
<213> ORGANISM: Saccharomyces cerevisiae

<400> SEQUENCE: 20

| | |
|---|---|
| aagcttcgcg gccgcctttc gattagcacg cacacacatc acatagactg cgtcataaaa | 60 |
| atacactacg gaaaaaccat aaagagcaaa gcgatacctc cttggaagga aaggagcac | 120 |
| gcttgtaagg gggatggggg ctaagaagtc attcactttc ttttcccttc gcggtccgga | 180 |
| cccgggaccc ctcctctccc cgcacgattt cttccttca tatcttcctt ttattcctat | 240 |
| cccgttgaag caaccgcact atgactaaat ggtgctggac atctccatgg ctgtgacttg | 300 |
| tgtgtatctc acagtggtaa cggcaccgtg gctcggaaac ggttccttcg tgacaattct | 360 |
| agaacagggg ctacagtctc gataatagaa taataagcgc attttgcta cgccgccgc | 420 |
| ggcgcccgtt tcccaatagg gaggcgcagt ttatcggcgg agctctactt cttcctattt | 480 |
| gggtaagccc ctttctgttt tcggccagtg gttgctgcag gctgcgccgg agaacatagt | 540 |
| gataagggat gtaactttcg atgagagaat tagcaagcga aaaaaaacta tggctagctg | 600 |
| ggagttgttt ttcaatcata taaaagggag aaattgttgc tcactatgtg acagtttctg | 660 |
| ggacgtctta acttttattg cagaggacta tcaaatcata cagatattgt caaaaaaaaa | 720 |
| aaagactaat aataacatat ggaagacgcc aaaaacataa agaaaggccc ggcgccattc | 780 |
| tatccgctgg aagatggaac cgctggagag caactgcata aggctatgaa gagatacgcc | 840 |
| ctggttcctg gaacaattgc ttttacagat gcacatatcg aggtggacat cacttacgct | 900 |
| gagtacttcg aaatgtccgt tcggttggca gaagctatga acgatatgg gctgaataca | 960 |
| aatcacagaa tcgtcgtatg cagtgaaaac tctcttcaat tctttatgcc ggtgttgggc | 1020 |
| gcgttattta tcggagttgc agttgcgccc gcgaacgaca tttataatga acgtgaattg | 1080 |
| ctcaacagta tgggcatttc gcagcctacc gtggtgttcg tttccaaaaa ggggttgcaa | 1140 |
| aaaattttga acgtgcaaaa aaagctccca atcatccaaa aaattattat catggattct | 1200 |
| aaaacggatt accagggatt tcagtcgatg tacacgttcg tcacatctca tctacctccc | 1260 |
| ggttttaatg aatacgattt tgtgccagag tccttcgata gggacaagac aattgcactg | 1320 |

-continued

```
atcatgaact cctctggatc tactggtctg cctaaaggtg tcgctctgcc tcatagaact    1380
gcctgcgtga gattctcgca tgccagagat cctattttg gcaatcaaat cattccggat    1440
actgcgattt taagtgttgt tccattccat cacggttttg gaatgtttac tacactcgga    1500
tatttgatat gtggatttcg agtcgtctta atgtatagat ttgaagaaga gctgtttctg    1560
aggagccttc aggattacaa gattcaaagt gcgctgctgg tgccaaccct attctccttc    1620
ttcgccaaaa gcactctgat tgacaaatac gatttatcta atttacacga aattgcttct    1680
ggtggcgctc cctctctaa ggaagtcggg gaagcggttg ccaagaggtt ccatctgcca    1740
ggtatcaggc aaggatatgg gctcactgag actacatcag ctattctgat tacacccgag    1800
ggggatgata aaccgggcgc ggtcgtaaa gttgttccat tttttgaagc gaaggttgtg    1860
gatctggata ccgggaaaac gctgggcgtt aatcaaagag gcgaactgtg tgtgagaggt    1920
cctatgatta tgtccggtta tgtaaacaat ccggaagcga ccaacgcctt gattgacaag    1980
gatggatggc tacattctgg agacatagct tactgggacg aagacgaaca cttcttcatc    2040
gttgaccgcc tgaagtctct gattaagtac aaaggctatc aggtggctcc cgctgaattg    2100
gaatccatct tgctccaaca ccccaacatc ttcgacgcag gtgtcgcagg tcttcccgac    2160
gatgacgccg tgaacttcc cgccgccgtt gttgttttgg agcacggaaa gacgatgacg    2220
gaaaaagaga tcgtggatta cgtcgccagt caagtaacaa ccgcgaaaaa gttgcgcgga    2280
ggagttgtgt tgtggacga agtaccgaaa ggtcttaccg gaaaactcga cgcaagaaaa    2340
atcagagaga tcctcataaa ggccaagaag gcggaaaga tcgccgtgta attggatcca    2400
gtttaaacag tagctttgga cttcttcgcc agaggtttgg tcaagtctcc aatcaaggtt    2460
gtcggcttgt ctaccttgcc agaaatttac gaaaagatgg aaaagggtca atcgttggt    2520 agatacgttg ttgacacttc taaataagcg aatttcttat gatttatgat ttttattatt    2580
aaataagtta taaaaaaat aagtgtatac aaattttaaa gtgactctta ggttttaaaa    2640
cgaaaattct tgttcttgag taactctttc ctgtaggtca ggttgctttc tcaggtatag    2700
catgaggtcg ctcttattga ccacacctct accggcatgc cgagcaaatg cctgcaaatc    2760 gctcccccatt tcacccaatt gtagatatgc taactccagc aatgagttga tgaatctcgg    2820
tgtgtatttt atgtcctcag aagacaacac ctgttgtaat cgttcttcca cacggatcgc    2880
ggccgcttga tcctctacgc cggacgcatc gtggccggca tcaccggcgc acaggtgcg    2940 gttgctggcg cctatatcgc cgacatcacc gatgggaag atcgggctcg ccacttcggg    3000
ctcatgagcg cttgtttcgg cgtgggtatg gtggcaggcc ccgtggccgg gggactgttg    3060
ggcgccatct ccttgcatgc accattcctt gcggcggcgg tgctcaacgg cctcaaccta    3120
ctactgggct gcttcctaat gcaggagtcg cataagggag agcgtcgacc gatgcccttg    3180
agagccttca acccagtcag ctccttccgg tgggcgcggg gcatgactat cgtcgccgca    3240
cttatgactg tcttctttat catgcaactc gtaggacagg tgccggcagc gctctgggtc    3300
attttcggcg aggaccgctt tcgctggagc gcgacgatga tcggcctgtc gcttgcgta    3360 ttcggaatct tgcacgccct cgctcaagcc ttcgtcactg gtcccgccac caaacgtttc    3420
ggcgagaagc aggccattat cgccggcatg gcggccgacg cgctgggcta cgtcttgctg    3480
gcgttcgcga cgcgaggctg gatggccttc cccattatga ttcttctcgc ttccggcggc    3540
atcgggatgc ccgcgttgca ggccatgctg tccaggcagg tagatgacga ccatcaggga    3600
cagcttcaag gatcgctcgc ggctcttacc agcctaactt cgatcactgg accgctgatc    3660
```

```
gtcacggcga tttatgccgc ctcggcgagc acatggaacg ggttggcatg gattgtaggc    3720
gccgccctat accttgtctg cctccccgcg ttgcgtcgcg gtgcatggag ccgggccacc    3780
tcgacctgaa tggaagccgg cggcacctcg ctaacggatt caccactcca agaattggag    3840
ccaatcaatt cttgcggaga actgtgaatg cgcaaaccaa ccettggcag aacatatcca    3900 tcgcgtccgc catctccagc agccgcacgc ggcgcatctc gggcagcgtt gggtcctggc    3960
cacgggtgcg catgatcgtg ctcctgtcgt tgaggacccg gctaggctgg cggggttgcc    4020
ttactggtta gcagaatgaa tcaccgatac gcgagcgaac gtgaagcgac tgctgctgca    4080
aaacgtctgc gacctgagca acaacatgaa tggtcttcgg tttccgtgtt tcgtaaagtc    4140
tggaaacgcg gaagtcagcg ccctgcacca ttatgttccg gatctgcatc gcaggatgct    4200
gctggctacc ctgtggaaca cctacatctg tattaacgaa gcgctggcat tgaccctgag    4260
tgattttcct ctggtcccgc cgcatccata ccgccagttg tttaccctca caacgttcca    4320
gtaaccgggc atgttcatca tcagtaaccc gtatcgtgag catcctctct cgtttcatcg    4380
gtatcattac ccccatgaac agaaattccc ccttacacgg aggcatcaag tgaccaaaca    4440
ggaaaaaacc gcccttaaca tggcccgctt tatcagaagc cagacattaa cgcttctgga    4500
gaaactcaac gagctggacg cggatgaaca ggcagacatc tgtgaatcgc ttcacgacca    4560
cgctgatgag ctttaccgca gctgcctcgc gcgtttcggt gatgacggtg aaaacctctg    4620
acacatgcag ctcccggaga cggtcacagc ttgtctgtaa gcggatgccg ggagcagaca    4680
agcccgtcag ggcgcgtcag cgggtgttgg cgggtgtcgg ggcgcagcca tgacccagtc    4740
acgtagcgat agcggagtgt atactggctt aactatgcgg catcagagca gattgtactg    4800
agagtgcacg atatccggtg tgaaataccg cacagatgcg taaggagaaa ataccgcatc    4860
aggcgctctt ccgcttcctc gctcactgac tcgctgcgct cggtcgttcg gctgcggcga    4920
gcggtatcag ctcactcaaa ggcggtaata cggttatcca cagaatcagg ggataacgca    4980
ggaaagaaca tgtgagcaaa aggccagcaa aaggccagga accgtaaaaa ggccgcgttg    5040
ctggcgtttt tccataggct ccgcccccct gacgagcatc acaaaaatcg acgctcaagt    5100
cagaggtggc gaaacccgac aggactataa agataccagg cgtttccccc tggaagctcc    5160
ctcgtgcgct ctcctgttcc gaccctgccg cttaccggat acctgtccgc ctttctccct    5220
tcgggaagcg tggcgctttc tcaatgctca cgctgtaggt atctcagttc ggtgtaggtc    5280
gttcgctcca agctgggctg tgtgcacgaa ccccccgttc agcccgaccg ctgcgcctta    5340
tccggtaact atcgtcttga gtccaacccg gtaagacacg acttatcgcc actggcagca    5400
gccactggta acaggattag cagagcgagg tatgtaggcg gtgctacaga gttcttgaag    5460
tggtggccta actacggcta cactagaagg acagtatttg gtatctgcgc tctgctgaag    5520
ccagttacct tcggaaaaag agttggtagc tcttgatccg gcaaacaaac caccgctggt    5580
agcggtggtt tttttgtttg caagcagcag attacgcgca gaaaaaaagg atctcaagaa    5640
gatcctttga tcttttctac ggggtctgac gctcagtgga acgaaaactc acgttaaggg    5700
attttggtca tgagattatc aaaaaggatc ttcacctaga tccttttaaa ttaaaaatga    5760
agttttaaat caatctaaag tatatatgag taaacttggt ctgacagtta ccaatgctta    5820
atcagtgagg cacctatctc agcgatctgt ctatttcgtt catccatagt tgcctgactc    5880
cccgtcgtgt agataactac gatacgggag ggcttaccat ctggccccag tgctgcaatg    5940
ataccgcgag acccacgctc accggctcca gatttatcag caataaacca gccagccgga    6000
agggccgagc gcagaagtgg tcctgcaact ttatccgcct ccatccagtc tattaattgt    6060
```

```
tgccgggaag ctagagtaag tagttcgcca gttaatagtt tgcgcaacgt tgttgccatt    6120
gctgcaggca tcgtggtgtc acgctcgtcg tttggtatgg cttcattcag ctccggttcc    6180
caacgatcaa ggcgagttac atgatccccc atgttgtgca aaaaagcggt tagctccttc    6240
ggtcctccga tcgttgtcag aagtaagttg ccgcagtgt tatcactcat ggttatggca     6300
gcactgcata attctcttac tgtcatgcca tccgtaagat gcttttctgt gactggtgag    6360
tactcaacca agtcattctg agaatagtgt atgcggcgac cgagttgctc ttgcccggcg    6420
tcaacacggg ataataccgc gccacatagc agaactttaa aagtgctcat cattggaaaa    6480
cgttcttcgg ggcgaaaact ctcaaggatc ttaccgctgt tgagatccag ttcgatgtaa    6540
cccactcgtg cacccaactg atcttcagca tcttttactt tcaccagcgt ttctgggtga    6600
gcaaaaacag gaaggcaaaa tgccgcaaaa aagggaataa gggcgacacg gaatgttga    6660 atactcatac tcttcctttt tcaatattat tgaagcattt atcagggtta ttgtctcatg    6720
agcggataca tatttgaatg tatttagaaa aataaacaaa taggggttcc gcgcacattt    6780
ccccgaaaag tgccacctga cgtctaagaa accattatta tcatgacatt aacctataaa    6840
aataggcgta tcacgaggcc ctttcgtctt caagaattcc acggactata gactatacta    6900
gtatactccg tctactgtac gatacacttc cgctcaggtc cttgtccttt aacgaggcct    6960
taccactctt ttgttactct attgatccag ctcagcaaag gcagtgtgat ctaagattct    7020
atcttcgcga tgtagtaaaa ctagctagac cgagaaagag actagaaatg caaaaggcac    7080
ttctacaatg gctgccatca ttattatccg atgtgacgct gcagaagcag aaatacacgc    7140
ggtcagtgaa gctattccgc tattgaataa cctcagtcac cttgtgcaag aacttaacaa    7200
gaaaccaatt attaaaggct tacttactga tagtagatca acgatcagta taattaagtc    7260
tacaaatgaa gagaaattta gaaacagatt ttttggcaca aaggcaatga gacttagaga    7320
tgaagtatca ggtaataatt tatacgtata ctacatcgag accaagaaga acattgctga    7380
tgtgatgaca aaacctcttc cgataaaaac atttaaacta ttaactaaca aatggattca    7440
ttagatctat tacattatgg gtggtatgtt ggaataaaaa tcaactatca tctactaact    7500
agtatttacg ttactagtat attatcatat acggtgttag aagatgacgc aaatgatgag    7560
aaatagtcat ctaaattagt ggaagctgaa acgcaaggat tgataatgta ataggatcaa    7620
tgaatattaa catataaaat gatgataata atatttatag aattgtgtag aattgcagat    7680
tcccttttat ggattcctaa atcctcgagg agaacttcta gtatatctac atacctaata    7740
ttattgcctt attaaaaatg gaatcccaac aattacatca aaatcccacat tctcttcaaa    7800 atcaattgtc ctgtacttcc ttgttcatgt gtgttcaaaa acgttatatt tataggataa    7860
ttatactcta tttctcaaca agtaattggt tgtttggccg agcggtctaa ggcgcctgat    7920
tcaagaaata tcttgaccgc agttaactgt gggaatactc aggtatcgta agatgcaaga    7980
gttcgaatct cttagcaacc attatttttt tcctcaacat aacgagaaca cacaggggcg    8040
ctatcgcaca gaatcaaatt cgatgactgg aatttttttg ttaatttcag aggtcgcctg    8100
acgcatatac cttttttcaac tgaaaattg ggagaaaaag gaaaggtgag agccgcggaa     8160
ccggcttttc atatagaata gagaagcgtt catgactaaa tgcttgcatc acaatacttg    8220
aagttgacaa tattatttaa ggacctattg ttttttccaa taggtggtta gcaatcgtct    8280
tactttctaa cttttcttac cttttacatt tcagcaaat atatatat atttcaagga     8340 tataccattc taatgtctgc ccctaagaag atcgtcgttt tgccaggtga ccacgttggt    8400
```

```
caagaaatca cagccgaagc cattaaggtt cttaaagcta tttctgatgt tcgttccaat   8460
gtcaagttcg atttcgaaaa tcatttaatt ggtggtgctg ctatcgatgc tacaggtgtc   8520
ccacttccag atgaggcgct ggaagcctcc aagaaggttg atgccgtttt gttaggtgct   8580
gtgggtggtc ctaaatgggg taccggtagt gttagacctg aacaaggttt actaaaaatc   8640
cgtaaagaac ttcaattgta cgccaactta agaccatgta actttgcatc cgactctctt   8700
ttagacttat ctccaatcaa gccacaattt gctaaaggta ctgacttcgt tgttgtcaga   8760
gaattagtgg gaggtattta ctttggtaag agaaaggaag acgatggtga tggtgtcgct   8820
tgggatagtg aacaatacac cgttccagaa gtgcaaagaa tcacaagaat ggccgctttc   8880
atggccctac aacatgagcc accattgcct atttggtcct tggataaagc taatgttttg   8940
gcctcttcaa gattatggag aaaaactgtg gaggaaacca tcaagaacga attccctaca   9000
ttgaaggttc aacatcaatt gattgattct gccgccatga tcctagttaa gaacccaacc   9060
cacctaaatg gtattataat caccagcaac atgtttggtg atatcatctc cgatgaagcc   9120
tccgttatcc caggttcctt gggtttgttg ccatctgcgt ccttggcctc tttgccagac   9180
aagaacaccg catttggttt gtacgaacca tgccacggtt ctgctccaga tttgccaaag   9240
aataaggtca accctatcgc cactatcttg tctgctgcaa tgatgttgaa attgtcattg   9300
aacttgcctg aagaaggtaa ggccattgaa gatgcagtta aaaaggtttt ggatgcaggt   9360
atcagaactg gtgatttagg tggttccaac agtaccacgg aagtcggtga tgctgtcgcc   9420
gaagaagtta agaaaatcct tgcttaaaaa gattctcttt ttttatgata tttgtacata   9480
aactttataa atgaaattca taatagaaac gacacgaaat tacaaaatgg aatatgttca   9540
tagggtagac gaaactatat acgcaatcta catacattta tcaagaagga gaaaaggag   9600
gatgtaaagg aatacaggta agcaaattga tactaatggc tcaacgtgat aaggaaaaag   9660
aattgcactt taacattaat attgacaagg aggagggcac cacacaaaaa gttaggtgta   9720
acagaaaatc atgaaactat gattcctaat ttatatattg gaggattttc tctaaaaaaa   9780
aaaaaataca acaaataaaa aacactcaat gacctgacca tttgatggag tttaagtcaa   9840
taccttcttg aaccatttcc cataatggtg aaagttccct caagaatttt actctgtcag   9900
aaacggcctt aacgacgtag tcgacctcct cttcagtact aaatctacca ataccaaatc   9960
tgatggaaga atgggctaat gcatcatcct tacccagcgc atgtaaaaca taagaaggtt  10020
ctagggaagc agatgtacag gctgaacccg aggataatgc gatatccctt agtgccatca  10080
ataaagattc tccttccacg taggcgaaag aaacgttaac acaccctgga taacgatgat  10140
ctggagatcc gttcaacgtg gtatgttcag cggataatag acctttgact aatttatcgg  10200
atagtctttt gatgtgagct tggtcgttgt caaattcttt cttcatcaat ctcgcagctt  10260
caccaaatcc cgctaccaat gggggggcca aagtaccaga tctcaatcct ctctcttggc  10320
caccaccgga tagtaaaggt tctaatctaa ctcttggtct ccttcttaca tagatggcac  10380
ctattccctt tggaccgtaa atcttgtgag aagaaattga tagtaaatca atgttcattt  10440
cattgacatc aatgtgaatc ttaccatagg cttgtgcggc gtcagtatga agtagatct   10500
tattctttct acaaattgca ccaatttctt taataggttg aatgacaccg atttcattat  10560
tgacagccat cacagagacg agacaggtat ctggtctaat ggcatcttcc aattccttca  10620
aatcgataag accttgatcg tccacattta ggaaagtgac ttcaaatccc tccttcatca  10680
tggcccgtgc ggcttccaag acacacttgt gttccgttct agtggtgatg atgtgttcct  10740
tagtcttctt ataaaatctt gggacaccct taagaaccat attattagat tcggtcgctc  10800
```

```
ccgaagtgaa tattatttcc ttggggtcgg cattgatcat ctttgctacg taagctctag   10860
cattttccac agcagtattt gtttcccaac cgtaagagtg agtgttggaa tgaggattac   10920
cataaagtcc cgtataaaac ttcaacatcg tatccaaaac cctagggtct gttggtgtag   10980
tggcttgcat gtcaagatat atgggacgag taccaaaacc tgtgttttct tgataagcat   11040
ggctcattgc agtgctacca gaagctacta cagcatctgg ggtggtaccg gatgcactcg   11100
cacgggcact agcctgtgcc tttgcagcag cctgaatatc ggtatgcgtt tccagagaga   11160
agttgtcgtc taacttcacg cctgctgcag tctcaatgat attcgaatac gctttgagga   11220
gatacagcct aatatccgac aaactgtttt acagatttac gatcgtactt gttacccatc   11280
attgaatttt gaacatccga acctgggagt ttccctgaa acagatagta tatttgaacc    11340
tgtataataa tatatagtct agcgctttac ggaagacaat gtatgtattt cggttcctgg   11400
agaaactatt gcatctattg cataggtaat cttgcacgtc gcatcccgg ttcattttct    11460 gcgtttccat cttgcacttc aatagcatat ctttgttaac gaagcatctg tgcttcattt   11520
tgtagaacaa aaatgcaacg cgagagcgct aattttcaa acaaagaatc tgagctgcat    11580
ttttacagaa cagaaatgca acgcgaaagc gctattttac caacgaagaa tctgtgcttc   11640 attttttgtaa aacaaaaatg caacgcgaga gcgctaattt ttcaaacaaa gaatctgagc   11700 tgcatttttta cagaacagaa atgcaacgcg agagcgctat tttaccaaca agaatctat    11760 acttcttttt tgttctacaa aaatgcatcc cgagagcgct attttctaa caaagcatct    11820 tagattactt tttttctcct ttgtgcgctc tataatgcag tctcttgata acttttttgca   11880 ctgtaggtcc gttaaggtta gaagaaggct actttggtgt ctatttttctc ttccataaaa   11940 aaagcctgac tccacttccc gcgtttactg attactagcg aagctgcggg tgcatttttt   12000
caagataaag gcatccccga ttatattcta taccgatgtg gattgcgcat actttgtgaa   12060
cagaaagtga tagcgttgat gattcttcat tggtcagaaa attatgaacg gtttcttcta   12120
ttttgtctct atatactacg tataggaaat gtttacattt tcgtattgtt ttcgattcac   12180
tctatgaata gttcttacta caattttttt gtctaaagag taatactaga gataaacata   12240
aaaaatgtag aggtcgagtt tagatgcaag ttcaaggagc gaaaggtgga tgggtaggtt   12300
atatagggat atagcacaga gatatatagc aaagagatac ttttgagcaa tgtttgtgga   12360
agcggtattc gcaatatttt agtagctcgt tacagtccgg tgcgtttttg gttttttgaa   12420
agtgcgtctt cagagcgctt ttggttttca aaagcgctct gaagttccta tactttctag   12480
agaataggaa cttcggaata ggaacttcaa agcgtttccg aaaacgagcg cttccgaaaa   12540
tgcaacgcga gctgcgcaca tacagctcac tgttcacgtc gcacctatat ctgcgtgttg   12600
cctgtatata tatacatg agaagaacgg catagtgcgt gtttatgctt aaatgcgtac    12660
ttatatgcgt ctatttatgt aggatgaaag gtagtctagt acctcctgtg atattatccc   12720
attccatgcg gggtatcgta tgcttccttc agcactaccc tttagctgtt ctatatgctg   12780
ccactcctca attggattag tctcatcctt caatgctatc atttcctttg atattcgatc   12840
ctaggcatag taccgagaaa ctagtgcgaa gtagtgatca ggtattgctg ttatctgatg   12900
agtatacgtt gtcctggcca cggcagaagc acgcttatcg ctccaatttc ccacaacatt   12960
agtcaactcc gttaggccct tcattgaaag aaatgaggtc atcaaatgtc ttccaatgtg   13020
agatttgggg ccattttta tagcaaagat tgaataaggc gcattttcct tca           13073
```

<210> SEQ ID NO 21

<211> LENGTH: 12851
<212> TYPE: DNA
<213> ORGANISM: Saccharomyces cerevisiae

<400> SEQUENCE: 21

```
aagcttagct aagcttcgcg gccgcgcaga aatgatgaag ggtgttagcg ccgtccactg      60
atgtgcctgg tagtcatgat ttacgtataa ctaacacatc atgaggacgg cggcgtcacc     120
ccaacgcaaa agagtgactt ccctgcgctt tgccaaaacc ccatacatcg ccatctggct     180
cctggcaggc cggttgatgg acatcagccg cctcccttaa ttgctaaagc ctccacaagg     240
cacaattaag caatatttcg ggaaagtaca ccagtcagtt tgcgctttta tgactgggtt     300
ctaaggtact agatgtgaag tagtggtgac agaatcaggg agataagagg gagcagggtg     360
gggtaatgat gtgcgataac aatcttgctt ggctaatcac ccccatatct tgtagtgagt     420
atataaatag gagcctccct tcctattgca actccataaa attttttttt gtagccactt     480
ctgtaacaag ataaataaaa ccaactaatc gagatatcac atatggaaga cgccaaaaac     540
ataaagaaag cccggcgcc attctatccg ctggaagatg gaaccgctgg agagcaactg     600
cataaggcta tgaagagata cgccctggtt cctggaacaa ttgcttttac agatgcacat     660
atcgaggtgg acatcactta cgctgagtac ttcgaaatgt ccgttcggtt ggcagaagct     720
atgaaacgat atgggctgaa tacaaatcac agaatcgtcg tatgcagtga aaactctctt     780
caattcttta tgccggtgtt gggcgcgtta tttatcggag ttgcagttgc gcccgcgaac     840
gacatttata atgaacgtga attgctcaac agtatggca tttcgcagcc taccgtggtg     900
ttcgtttcca aaaggggtt gcaaaaaatt ttgaacgtgc aaaaaagct cccaatcatc     960
caaaaaatta ttatcatgga ttctaaaacg gattaccagg gatttcagtc gatgtacacg    1020
ttcgtcacat ctcatctacc tcccggtttt aatgaatacg attttgtgcc agagtccttc    1080
gatagggaca agacaattgc actgatcatg aactcctctg gatctactgg tctgcctaaa    1140
ggtgtcgctc tgcctcatag aactgcctgc gtgagattct cgcatgccag agatcctatt    1200
tttggcaatc aaatcattcc ggatactgcg atttttaagtg ttgttccatt ccatcacggt    1260
tttggaatgt ttactacact cggatatttg atatgtggat ttcgagtcgt cttaatgtat    1320
agatttgaag aagagctgtt tctgaggagc cttcaggatt acaagattca aagtgcgctg    1380
ctggtgccaa cccctattctc cttcttcgcc aaaagcactc tgattgacaa atacgattta    1440
tctaatttac acgaaattgc ttctggtggc gctcccctct ctaaggaagt cggggaagcg    1500
gttgccaaga ggttccatct gccaggtatc aggcaaggat atgggctcac tgagactaca    1560
tcagctattc tgattacacc cgagggggat gataaaccgg gcgcggtcgg taaagttgtt    1620
ccatttttg aagcgaaggt tgtggatctg gataccggga aaacgctggg cgttaatcaa    1680
agaggcgaac tgtgtgtgag aggtcctatg attatgtccg gttatgtaaa caatccggaa    1740
gcgaccaacg ccttgattga caaggatgga tggctacatt ctggagacat agcttactgg    1800
gacgaagacg aacacttctt catcgttgac cgcctgaagt ctctgattaa gtacaaaggc    1860
tatcaggtgg ctcccgctga attggaatcc atcttgctcc aacaccccaa catcttcgac    1920
gcaggtgtcg caggtcttcc cgacgatgac gccggtgaac ttcccgccgc cgttgttgtt    1980
ttggagcacg gaaagacgat gacggaaaaa gagatcgtgg attacgtcgc cagtcaagta    2040
acaaccgcaa aagttgcgc ggaggagttg tgtttgtgga cgaagtaccg aaaggtctta    2100
ccggaaaact cgacgcaaga aaaatcagag agatcctcat aaaggccaag aagggcggaa    2160
agatcgccgt gtaattggat ccagtttaaa cagtagcttt ggacttcttc gccagaggtt    2220
```

-continued

```
tggtcaagtc tccaatcaag gttgtcggct tgtctacctt gccagaaatt tacgaaaaga    2280
tggaaaaggg tcaaatcgtt ggtagatacg ttgttgacac ttctaaataa gcgaatttct    2340
tatgatttat gattttatt attaaataag ttataaaaaa aataagtgta tacaaatttt    2400
aaagtgactc ttaggtttta aaacgaaaat tcttgttctt gagtaactct ttcctgtagg    2460
tcaggttgct ttctcaggta tagcatgagg tcgctcttat tgaccacacc tctaccggca    2520
tgccgagcaa atgcctgcaa atcgctcccc atttcaccca attgtagata tgctaactcc    2580
agcaatgagt tgatgaatct cggtgtgtat tttatgtcct cagaagacaa cacctgttgt    2640
aatcgttctt ccacacggat cgcggccgct tgatcctcta cgccggacgc atcgtggccg    2700
gcatcaccgg cgccacaggt gcggttgctg gcgcctatat cgccgacatc accgatgggg    2760
aagatcgggc tcgccacttc gggctcatga gcgcttgttt cggcgtgggt atggtggcag    2820
gccccgtggc cggggactg ttgggcgcca tctccttgca tgcaccattc cttgcggcgg    2880
cggtgctcaa cggcctcaac ctactactgg gctgcttcct aatgcaggag tcgcataagg    2940
gagagcgtcg accgatgccc ttgagagcct tcaacccagt cagctccttc cggtgggcgc    3000 gggcatgac tatcgtcgcc gcacttatga ctgtcttctt tatcatgcaa ctcgtaggac    3060
aggtgccggc agcgctctgg gtcatttccg gcgaggaccg ctttcgctgg agcgcgacga    3120
tgatcggcct gtcgcttgcg gtattcggaa tcttgcacgc cctcgctcaa gccttcgtca    3180
ctggtcccgc caccaaacgt ttcggcgaga agcaggccat tatcgccggc atggcggccg    3240
acgcgctggg ctacgtcttg ctggcgttcg cgacgcgagg ctggatggcc ttccccatta    3300
tgattcttct cgcttccggc ggcatcggga tgcccgcgtt gcaggccatg ctgtccaggc    3360
aggtagatga cgaccatcag ggacagcttc aaggatcgct cgcggctctt accagcctaa    3420
cttcgatcac tggaccgctg atcgtcacgg cgatttatgc cgcctcggcg agcacatgga    3480
acgggttggc atggattgta ggcgccgccc tataccttgt ctgcctcccc gcgttgcgtc    3540
gcggtgcatg gagccgggcc acctcgacct gaatggaagc cggcggcacc tcgctaacgg    3600
attcaccact ccaagaattg gagccaatca attcttgcgg agaactgtga atgcgcaaac    3660
caacccttgg cagaacatat ccatcgcgtc cgccatctcc agcagccgca cgcggcgcat    3720
ctcgggcagc gttgggtcct ggccacgggt gcgcatgatc gtgctcctgt cgttgaggac    3780
ccggctaggc tggcggggtt gccttactgg ttagcagaat gaatcaccga tacgcgagcg    3840
aacgtgaagc gactgctgct gcaaaacgtc tgcgacctga gcaacaacat gaatggtctt    3900
cggtttccgt gtttcgtaaa gtctggaaac gcggaagtca gcgccctgca ccattatgtt    3960
ccggatctgc atcgcaggat gctgctggct accctgtgga acacctacat ctgtattaac    4020
gaagcgctgg cattgaccct gagtgatttt tctctggtcc cgccgcatcc ataccgccag    4080
ttgtttaccc tcacaagttc cagtaaccgg gcatgttcat catcagtaac ccgtatcgtg    4140
agcatcctct ctcgtttcat cggtatcatt accccccatga acagaaattc ccccttacac    4200
ggaggcatca agtgaccaaa caggaaaaaa ccgcccttaa catggcccgc tttatcagaa    4260
gccagacatt aacgcttctg gagaaactca acgagctgga cgcggatgaa caggcagaca    4320
tctgtgaatc gcttcacgac cacgctgatg agctttaccg cagctgcctc gcgcgtttcg    4380
gtgatgacgg tgaaaacctc tgacacatgc agctcccgga gacggtcaca gcttgtctgt    4440
aagcggatgc cgggagcaga caagcccgtc agggcgcgtc agcgggtgtt ggcgggtgtc    4500
ggggcgcagc catgacccag tcacgtagcg atagcggagt gtatactggc ttaactatgc    4560
```

-continued

```
ggcatcagag cagattgtac tgagagtgca cgatatccgg tgtgaaatac cgcacagatg    4620
cgtaaggaga aataccgcca tcaggcgctc ttccgcttcc tcgctcactg actcgctgcg    4680
ctcggtcgtt cggctgcggc gagcggtatc agctcactca aaggcggtaa tacggttatc    4740
cacagaatca ggggataacg caggaaagaa catgtgagca aaaggccagc aaaaggccag    4800
gaaccgtaaa aaggccgcgt tgctggcgtt tttccatagg ctccgccccc ctgacgagca    4860
tcacaaaaat cgacgctcaa gtcagaggtg cgaaacccg acaggactat aaagatacca    4920
ggcgtttccc cctggaagct ccctcgtgcg ctctcctgtt ccgaccctgc cgcttaccgg    4980
atacctgtcc gcctttctcc cttcgggaag cgtggcgctt tctcaatgct cacgctgtag    5040
gtatctcagt tcggtgtagg tcgttcgctc caagctgggc tgtgtgcacg aaccccccgt    5100
tcagcccgac cgctgcgcct tatccggtaa ctatcgtctt gagtccaacc cggtaagaca    5160
cgacttatcg ccactggcag cagccactgg taacaggatt agcagagcga ggtatgtagg    5220
cggtgctaca gagttcttga agtggtggcc taactacggc tacactagaa ggacagtatt    5280
tggtatctgc gctctgctga agccagttac cttcggaaaa agagttggta gctcttgatc    5340
cggcaaacaa accaccgctg gtagcggtgg ttttttgtt tgcaagcagc agattacgcg    5400
cagaaaaaaa ggatctcaag aagatccttt gatcttttct acggggtctg acgctcagtg    5460
gaacgaaaac tcacgttaag ggattttggt catgagatta tcaaaaagga tcttcaccta    5520
gatcctttta aattaaaaat gaagttttaa atcaatctaa agtatatatg agtaaacttg    5580
gtctgacagt taccaatgct taatcagtga ggcacctatc tcagcgatct gtctatttcg    5640
ttcatccata gttgcctgac tccccgtcgt gtagataact acgatacggg agggcttacc    5700
atctggcccc agtgctgcaa tgataccgcg agacccacgc tcaccggctc cagatttatc    5760
agcaataaac cagccagccg gaagggccga gcgcagaagt ggtcctgcaa ctttatccgc    5820
ctccatccag tctattaatt gttgccggga agctagagta agtagttcgc cagttaatag    5880
tttgcgcaac gttgttgcca ttgctgcagg catcgtggtg tcacgctcgt cgtttggtat    5940
ggcttcattc agctccggtt cccaacgatc aaggcgagtt acatgatccc ccatgttgtg    6000
caaaaaagcg gttagctcct tcggtcctcc gatcgttgtc agaagtaagt tggccgcagt    6060
gttatcactc atggttatgg cagcactgca taattctctt actgtcatgc catccgtaag    6120
atgcttttct gtgactggtg agtatcaacc aagtcattct gagaatagtg tatgcggcga    6180
ccgagttgct cttgcccggc gtcaacacgg gataataccg cgccacatag cagaacttta    6240
aaagtgctca tcattggaaa acgttcttcg gggcgaaaac tctcaaggat cttaccgctg    6300
ttgagatcca gttcgatgta acccactcgt gcacccaact gatcttcagc atcttttact    6360
ttcaccagcg tttctgggtg agcaaaaaca ggaaggcaaa atgccgcaaa aaagggaata    6420
agggcgacac ggaaatgttg aatactcata ctcttccttt ttcaatatta ttgaagcatt    6480
tatcagggtt attgtctcat gagcggatac atatttgaat gtatttagaa aaataaacaa    6540
ataggggttc cgcgcacatt tccccgaaaa gtgccacctg acgtctaaga accattatt    6600
atcatgacat aacctataa aaataggcgt atcacgaggc cctttcgtct tcaagaattc    6660
cacggactat agactatact agtatactcc gtctactgta cgatacactt ccgctcaggt    6720
ccttgtcctt taacgaggcc ttaccactct tttgttactc tattgatcca gctcagcaaa    6780
ggcagtgtga tctaagattc tatcttcgcg atgtagtaaa actagctaga ccagaaaga    6840
gactagaaat gcaaaaggca cttctacaat ggctgccatc attattatcc gatgtgacgc    6900
tgcagaagca gaaatacacg cggtcagtga agctattccg ctattgaata acctcagtca    6960
```

```
ccttgtgcaa gaacttaaca agaaaccaat tattaaaggc ttacttactg atagtagatc   7020
aacgatcagt ataattaagt ctacaaatga agagaaattt agaaacagat tttttggcac   7080
aaaggcaatg agacttagag atgaagtatc aggtaataat ttatacgtat actacatcga   7140
gaccaagaag aacattgctg atgtgatgac aaaacctctt ccgataaaaa catttaaact   7200
attaactaac aaatggattc attagatcta ttacattatg ggtggtatgt tggaataaaa   7260
atcaactatc atctactaac tagtatttac gttactagta tattatcata tacggtgtta   7320
gaagatgacg caaatgatga gaaatagtca tctaaattag tggaagctga aacgcaagga   7380
ttgataatgt aataggatca atgaatatta acatataaaa tgatgataat aatatttata   7440
gaattgtgta gaattgcaga ttcccttttg tggattccta aatcctcgag gagaacttct   7500
agtatatcta catacctaat attattgcct tattaaaaat ggaatcccaa caattacatc   7560
aaaatccaca ttctcttcaa aatcaattgt cctgtacttc cttgttcatg tgtgttcaaa   7620
aacgttatat ttataggata attatactct atttctcaac aagtaattgg ttgtttggcc   7680
gagcggtcta aggcgcctga ttcaagaaat atcttgaccg cagttaactg tgggaatact   7740
caggtatcgt aagatgcaag agttcgaatc tcttagcaac cattattttt ttcctcaaca   7800
taacgagaac acacagggc gctatcgcac agaatcaaat tcgatgactg gaaatttttt   7860
gttaatttca gaggtcgcct gacgcatata ccttttttcaa ctgaaaaatt gggagaaaaa   7920
ggaaaggtga gagccgcgga accggctttt catatagaat agagaagcgt tcatgactaa   7980
atgcttgcat cacaatactt gaagttgaca atattattta aggacctatt gttttttcca   8040 ataggtggt agcaatcgtc ttactttcta acttttctta ccttttacat ttcagcaata   8100
tatatatata tatttcaagg atataccatt ctaatgtctg cccctaagaa gatcgtcgtt   8160
ttgccaggtg accacgttgg tcaagaaatc acgccgaagc cattaaggtt cttaaagcta   8220
tttctgatgt tcgttccaat gtcaagttcg atttcgaaaa tcatttaatt ggtggtgctg   8280
ctatcgatgc tacaggtgtc ccacttccag atgaggcgct ggaagcctcc aagaaggttg   8340
atgccgtttt gttaggtgct gtgggtggtc ctaaatgggg taccggtagt gttagacctg   8400
aacaaggttt actaaaaatc cgtaaagaac ttcaattgta cgccaactta agaccatgta   8460
actttgcatc cgactctctt ttagacttat ctccaatcaa gccacaattt gctaaaggta   8520
ctgacttcgt tgttgtcaga gaattagtgg gaggtatta ctttggtaag agaaaggaag   8580
acgatggtga tggtgtcgct tgggatagtg aacaatacac cgttccagaa gtgcaaagaa   8640
tcacaagaat ggccgctttc atggccctac aacatgagcc accattgcct atttggtcct   8700
tggataaagc taatgttttg gcctcttcaa gattatggag aaaaactgtg gaggaaacca   8760
tcaagaacga attccctaca ttgaaggttc aacatcaatt gattgattct gccgccatga   8820
tcctagttaa gaacccaacc cacctaaatg gtattataat caccagcaac atgtttggtg   8880
atatcatctc cgatgaagcc tccgttatcc caggttcctt gggtttgttg ccatctgcgt   8940
ccttggcctc tttgccagac aagaacaccg catttggttt gtacgaacca tgccacggtt   9000
ctgctccaga tttgccaaag aataaggtca accctatcgc cactatcttg tctgctgcaa   9060
tgatgttgaa attgtcattg aacttgcctg aagaaggtaa ggccattgaa gatgcagtta   9120
aaaaggtttt ggatgcaggt atcagaactg gtgatttagg tggttccaac agtaccacgg   9180
aagtcggtga tgctgtcgcc gaagaagtta agaaaatcct tgcttaaaaa gattctcttt   9240
ttttatgata tttgtacata aactttataa atgaaattca taatagaaac gacacgaaat   9300
```

-continued

| | |
|---|---|
| tacaaaatgg aatatgttca tagggtagac gaaactatat acgcaatcta catacattta | 9360 |
| tcaagaagga gaaaaggag gatgtaaagg aatacaggta agcaaattga tactaatggc | 9420 |
| tcaacgtgat aaggaaaaag aattgcactt taacattaat attgacaagg aggagggcac | 9480 |
| cacacaaaaa gttaggtgta acagaaaatc atgaaactat gattcctaat ttatatattg | 9540 |
| gaggattttc tctaaaaaaa aaaaaataca acaaataaaa aacactcaat gacctgacca | 9600 |
| tttgatggag tttaagtcaa taccttcttg aaccatttcc cataatggtg aaagttccct | 9660 |
| caagaatttt actctgtcag aaacggcctt aacgacgtag tcgacctcct cttcagtact | 9720 |
| aaatctacca ataccaaatc tgatggaaga atgggctaat gcatcatcct tacccagcgc | 9780 |
| atgtaaaaca taagaaggtt ctagggaagc agatgtacag gctgaacccg aggataatgc | 9840 |
| gatatccctt agtgccatca ataaagattc tccttccacg taggcgaaag aaacgttaac | 9900 |
| acacctgga taacgatgat ctggagatcc gttcaacgtg gtatgttcag cggataatag | 9960 |
| acctttgact aatttatcgg atagtctttt gatgtgagct tggtcgttgt caaattcttt | 10020 |
| cttcatcaat ctcgcagctt caccaaatcc cgctaccaat ggggggggcca aagtaccaga | 10080 |
| tctcaatcct ctctcttggc caccaccgga tagtaaaggt tctaatctaa ctcttggtct | 10140 |
| ccttcttaca tagatggcac ctattcccct tggaccgtaa atcttgtgag aagaaattga | 10200 |
| tagtaaatca atgttcattt cattgacatc aatgtgaatc taccataggc ttgtgcggcg | 10260 |
| tcagtatgaa agtagatctt attctttcta caaattgcac caatttcttt aataggttga | 10320 |
| atgacaccga tttcattatt gacagccatc acagagacga gacaggtatc tggtctaatg | 10380 |
| gcatcttcca attccttcaa atcgataaga ccttgatcgt ccacatttag gaaagtgact | 10440 |
| tcaaatccct ccttcatcat ggcccgtgcg gcttccaaga cacacttgtg ttccgttcta | 10500 |
| gtggtgatga tgtgtttctt agtcttctta taaaatcttg ggacacccctt aagaaccata | 10560 |
| ttattagatt cggtcgctcc cgaagtgaat attatttcct tggggtcggc attgatcatc | 10620 |
| tttgctacgt aagctctagc attttccaca gcagtatttg tttcccaacc gtaagagtga | 10680 |
| gtgttggaat gaggattacc ataaagtccc gtataaaact tcaacatcgt atccaaaacc | 10740 |
| ctagggtctg ttggtgtagt ggcttgcatg tcaagatata tgggacgagt accaaaacct | 10800 |
| gtgttttctt gataagcatg gctcattgca gtgctaccag aagctactac agcatctggg | 10860 |
| gtggtaccgg atgcactcgc acgggcacta gcctgtgcct ttgcagcagc ctgaatatcg | 10920 |
| gtatgcgttt ccagagagaa gttgtcgtct aacttcacgc ctgctgcagt ctcaatgata | 10980 |
| ttcgaatacg ctttgaggag atacagccta atatccgaca aactgtttta cagatttacg | 11040 |
| atcgtacttg ttacccatca ttgaattttg aacatccgaa cctgggagtt ttccctgaaa | 11100 |
| cagatagtat atttgaacct gtataataat atatagtcta gcgctttacg gaagacaatg | 11160 |
| tatgtatttc ggttcctgga gaaactattg catctattgc ataggtaatc ttgcacgtcg | 11220 |
| catcccccggt tcatttttctg cgtttccatc ttgcacttca atagcatatc tttgttaacg | 11280 |
| aagcatctgt gcttcatttt gtagaacaaa atgcaacgc gagagcgcta atttttcaaa | 11340 |
| caaagaatct gagctgcatt tttacagaac agaaatgcaa cgcgaaagcg ctattttacc | 11400 |
| aacgaagaat ctgtgcttca ttttttgtaaa acaaaaatgc aacgcgagag cgctaatttt | 11460 |
| tcaaacaaag aatctgagct gcattttttac agaacagaaa tgcaacgcga gagcgctatt | 11520 |
| ttaccaacaa agaatctata cttcttttttt gttctacaaa aatgcatccc gagagcgcta | 11580 |
| tttttctaac aaagcatctt agattacttt ttttctcctt tgtgcgctct ataatgcagt | 11640 |
| ctcttgataa cttttttgcac tgtaggtccg ttaaggttag aagaaggcta ctttggtgtc | 11700 |

-continued

```
tattttctct tccataaaaa aagcctgact ccacttcccg cgtttactga ttactagcga    11760
agctgcgggt gcattttttc aagataaagg catccccgat tatattctat accgatgtgg    11820
attgcgcata ctttgtgaac agaaagtgat agcgttgatg attcttcatt ggtcagaaaa    11880
ttatgaacgg tttcttctat tttgtctcta tatactacgt ataggaaatg tttacatttt    11940
cgtattgttt tcgattcact ctatgaatag ttcttactac aatttttttg tctaaagagt    12000
aatactagag ataaacataa aaatgtaga ggtcgagttt agatgcaagt tcaaggagcg    12060
aaaggtggat gggtaggtta tatagggata tagcacagag atatatagca aagagatact    12120
tttgagcaat gtttgtggaa gcggtattcg caatatttta gtagctcgtt acagtccggt    12180 gcgttttttgg ttttttgaaa gtgcgtcttc agagcgcttt tggttttcaa aagcgctctg    12240
aagttcctat actttctaga gaataggaac ttcggaatag gaacttcaag cgtttccgaa    12300
aacgagcgct tccgaaaatg caacgcgagc tgcgcacata cagctcactg ttcacgtcgc    12360
acctatatct gcgtgttgcc tgtatatata tatacatgag aagaacggca tagtgcgtgt    12420
ttatgcttaa atgcgtactt tatgcgtct atttatgtag gatgaaaggt agtctagtac    12480
ctcctgtgat attatcccat tccatgcggg gtatcgtatg cttccttcag cactacccttt    12540 tagctgttct atatgctgcc actcctcaat tggattagtc tcatccttca atgctatcat    12600
ttcctttgat attcgatcct aggcatagta ccgagaaact agtgcgaagt agtgatcagg    12660
tattgctgtt atctgatgag tatacgttgt cctggccacg gcagaagcac gcttatcgct    12720
ccaatttccc acaacattag tcaactccgt taggcccttc attgaaagaa atgaggtcat    12780
caaatgtctt ccaatgtgag attttgggcc attttttata gcaaagattg ataaggcgc    12840 attttttcttc a    12851
```

<210> SEQ ID NO 22
<211> LENGTH: 12850
<212> TYPE: DNA
<213> ORGANISM: Saccharomyces cerevisiae

<400> SEQUENCE: 22

```
aagcttcgcg gccgcggagg tctgcttcac gagcgcggtg tgcgcctagt attgccccga     60
cggtccgggt gcctatccct agatttcgtc gtgccccgac ccaaatagtt aaacgtgtgg    120
tttatgggtg caccagggct ttatcgtgtt ttatatcgat ggcgatttgt gcctccagtg    180
tatttttgta tatccaatta aggtttctta cctaatttta tttttatcat ctttagttaa    240
tgctggtttg ctctgttttct gctgctttct gtgcggttct cctcttctct tgtttcttcg    300
tgttgtcccc catcgccgat gggcttatat ggcgtatata tatagagcga gttttacgt    360 cgaagatcat ctcagtttgc ttgatagcct ttctacttta ttactttcgt ttttaacctc    420
attatacttt agttttcttt gatcggtttt tttctctgta tacttaaaag ttcaaatcaa    480
agaaacatac aaaactacgt ttatatcaat tacatatgga agacgccaaa aacataaaga    540
aaggcccggc gccattctat ccgctggaag atggaaccgc tggagagcaa ctgcataagg    600
ctatgaagag atacgccctg gttcctggaa caattgcttt tacagatgca catatcgagg    660
tggacatcac ttacgctgag tacttcgaaa tgtccgttcg gttggcagaa gctatgaaac    720
gatatgggct gaatacaaat cacagaatcg tcgtatgcag tgaaaactct cttcaattct    780
ttatgccggt gttgggcgcg ttatttatcg gagttgcagt tgcgcccgcg aacgacattt    840
ataatgaacg tgaattgctc aacagtatgg gcatttcgca gcctaccgtg gtgttcgttt    900
```

-continued

| | | | | |
|---|---|---|---|---|
| ccaaaaaggg | gttgcaaaaa | attttgaacg | tgcaaaaaaa | gctcccaatc | atccaaaaaa | 960 |
| ttattatcat | ggattctaaa | acggattacc | agggatttca | gtcgatgtac | acgttcgtca | 1020 |
| catctcatct | acctcccggt | tttaatgaat | acgattttgt | gccagagtcc | ttcgataggg | 1080 |
| acaagacaat | tgcactgatc | atgaactcct | ctggatctac | tggtctgcct | aaaggtgtcg | 1140 |
| ctctgcctca | tagaactgcc | tgcgtgagat | tctcgcatgc | cagagatcct | attttttggca | 1200 |
| atcaaatcat | tccggatact | gcgattttaa | gtgttgttcc | attccatcac | ggttttggaa | 1260 |
| tgtttactac | actcggatat | ttgatatgtg | gatttcgagt | cgtcttaatg | tatagatttg | 1320 |
| aagaagagct | gtttctgagg | agccttcagg | attacaagat | tcaaagtgcg | ctgctggtgc | 1380 |
| caaccctatt | ctccttcttc | gccaaaagca | ctctgattga | caaatacgat | ttatctaatt | 1440 |
| tacacgaaat | tgcttctggt | ggcgctcccc | tctctaagga | agtcggggaa | gcggttgcca | 1500 |
| agaggttcca | tctgccaggt | atcaggcaag | gatatgggct | cactgagact | acatcagcta | 1560 |
| ttctgattac | acccgagggg | gatgataaac | cgggcgcggt | cggtaaagtt | gttccatttt | 1620 |
| ttgaagcgaa | ggttgtggat | ctggataccg | ggaaaacgct | gggcgttaat | caaagaggcg | 1680 |
| aactgtgtgt | gagaggtcct | atgattatgt | ccggttatgt | aaacaatccg | gaagcgacca | 1740 |
| acgccttgat | tgacaaggat | ggatggctac | attctggaga | catagcttac | tgggacgaag | 1800 |
| acgaacactt | cttcatcgtt | gaccgcctga | agtctctgat | taagtacaaa | ggctatcagg | 1860 |
| tggctcccgc | tgaattggaa | tccatcttgc | tccaacaccc | caacatcttc | gacgcaggtg | 1920 |
| tcgcaggtct | tcccgacgat | gacgccggtg | aacttcccgc | cgccgttgtt | gttttggagc | 1980 |
| acggaaagac | gatgacggaa | aaagagatcg | tggattacgt | cgccagtcaa | gtaacaaccg | 2040 |
| cgaaaaagtt | gcgcggagga | gttgtgtttg | tggacgaagt | accgaaaggt | cttaccggaa | 2100 |
| aactcgacgc | aagaaaaatc | agagagatcc | tcataaaggc | caagaagggc | ggaaagatcg | 2160 |
| ccgtgtaatt | ggatccagtt | taaacagtag | ctttggactt | cttcgccaga | ggtttggtca | 2220 |
| agtctccaat | caaggttgtc | ggcttgtcta | ccttgccaga | aatttacgaa | aagatggaaa | 2280 |
| agggtcaaat | cgttggtaga | tacgttgttg | acacttctaa | ataagcgaat | tcttatgat | 2340 |
| ttatgatttt | tattattaaa | taagttataa | aaaaaataag | tgtatacaaa | ttttaaagtg | 2400 |
| actcttaggt | tttaaaacga | aaattcttgt | tcttgagtaa | ctctttcctg | taggtcaggt | 2460 |
| tgctttctca | ggtatagcat | gaggtcgctc | ttattgacca | cacctctacc | ggcatgccga | 2520 |
| gcaaatgcct | gcaaatcgct | ccccatttca | cccaattgta | gatatgctaa | ctccagcaat | 2580 |
| gagttgatga | atctcggtgt | gtattttatg | tcctcagaag | acaacacctg | ttgtaatcgt | 2640 |
| tcttccacac | ggatcgcggc | cgcttgatcc | tctacgccgg | acgcatcgtg | gccggcatca | 2700 |
| ccggcgccac | aggtgcggtt | gctggcgcct | atatcgccga | catcaccgat | ggggaagatc | 2760 |
| gggctcgcca | cttcgggctc | atgagcgctt | gtttcggcgt | gggtatggtg | gcaggccccg | 2820 |
| tggccggggg | actgttgggc | gccatctcct | tgcatgcacc | attccttgcg | gcggcggtgc | 2880 |
| tcaacggcct | caacctacta | ctgggctgct | tcctaatgca | ggagtcgcat | aagggagagc | 2940 |
| gtcgaccgat | gcccttgaga | gccttcaacc | cagtcagctc | cttccggtgg | gcgcggggca | 3000 |
| tgactatcgt | cgccgcactt | atgactgtct | tctttatcat | gcaactcgta | ggacaggtgc | 3060 |
| cggcagcgct | ctgggtcatt | ttcggcgagg | accgctttcg | ctggagcgcg | acgatgatcg | 3120 |
| gcctgtcgct | tgcggtattc | ggaatcttgc | acgccctcgc | tcaagccttc | gtcactggtc | 3180 |
| ccgccaccaa | acgtttcggc | gagaagcagg | ccattatcgc | cggcatggcg | gccgacgcgc | 3240 |
| tgggctacgt | cttgctggcg | ttcgcgacgc | gaggctggat | ggccttcccc | attatgattc | 3300 |

-continued

```
ttctcgcttc cggcggcatc gggatgcccg cgttgcaggc catgctgtcc aggcaggtag    3360
atgacgacca tcagggacag cttcaaggat cgctcgcggc tcttaccagc ctaacttcga    3420
tcactggacc gctgatcgtc acggcgattt atgccgcctc ggcgagcaca tggaacgggt    3480
tggcatggat tgtaggcgcc gccctatacc ttgtctgcct ccccgcgttg cgtcgcggtg    3540
catggagccg ggccacctcg acctgaatgg aagccggcgc cacctcgcta acggattcac    3600
cactccaaga attggagcca atcaattctt gcggagaact gtgaatgcgc aaaccaaccc    3660
ttggcagaac atatccatcg cgtccgccat ctccagcagc cgcacgcggc gcatctcggg    3720
cagcgttggg tcctggccac gggtgcgcat gatcgtgctc ctgtcgttga ggacccggct    3780
aggctggcgg ggttgcctta ctggttagca gaatgaatca ccgatacgcg agcgaacgtg    3840
aagcgactgc tgctgcaaaa cgtctgcgac ctgagcaaca acatgaatgg tcttcggttt    3900
ccgtgtttcg taaagtctgg aaacgcggaa gtcagcgccc tgcaccatta tgttccggat    3960
ctgcatcgca ggatgctgct ggctaccctg tggaacacct acatctgtat taacgaagcg    4020
ctggcattga ccctgagtga tttttctctg gtcccgccgc atccataccg ccagttgttt    4080
accctcacaa cgttccagta accgggcatg ttcatcatca gtaacccgta tcgtgagcat    4140
cctctctcgt ttcatcggta tcattacccc catgaacaga aattcccccct acacggagg    4200 catcaagtga ccaaacagga aaaaccgcc cttaacatgg cccgctttat cagaagccag    4260
acattaacgc ttctggagaa actcaacgag ctggacgcgg atgaacaggc agacatctgt    4320
gaatcgcttc acgaccacgc tgatgagctt taccgcagct gcctcgcgcg tttcggtgat    4380
gacggtgaaa acctctgaca catgcagctc ccggagacgg tcacagcttg tctgtaagcg    4440
gatgccggga gcagacaagc ccgtcagggc gcgtcagcgg gtgttggcgg gtgtcggggc    4500
gcagccatga cccagtcacg tagcgatagc ggagtgtata ctggcttaac tatgcggcat    4560
cagagcagat tgtactgaga gtgcacgata tccggtgtga ataccgcac agatgcgtaa    4620 ggagaaaata ccgcatcagg cgctcttccg cttcctcgct cactgactcg ctgcgctcgg    4680
tcgttcggct gcggcgagcg gtatcagctc actcaaaggc ggtaatacgg ttatccacag    4740
aatcagggga taacgcagga aagaacatgt gagcaaaagg ccagcaaaag gccaggaacc    4800
gtaaaaaggc cgcgttgctg gcgttttcc ataggctccg cccccctgac gagcatcaca    4860
aaaatcgacg ctcaagtcag aggtggcgaa acccgacagg actataaaga taccaggcgt    4920
ttccccctgg aagctccctc gtgcgctctc ctgttccgac cctgccgctt accggatacc    4980
tgtccgcctt tctcccttcg ggaagcgtgg cgctttctca atgctcacgc tgtaggtatc    5040
tcagttcggt gtaggtcgtt cgctccaagc tgggctgtgt gcacgaaccc ccgttcagc    5100 ccgaccgctg cgccttatcc ggtaactatc gtcttgagtc aacccggta agacacgact    5160 tatcgccact ggcagcagcc actggtaaca ggattagcag agcgaggtat gtaggcggtg    5220
ctacagagtt cttgaagtgg tggcctaact acggctacac tagaaggaca gtatttggta    5280
tctgcgctct gctgaagcca gttaccttcg gaaaaagagt tggtagctct tgatccggca    5340
aacaaaccac cgctggtagc ggtggttttt tgtttgcaa gcagcagatt acgcgcagaa    5400
aaaaaggatc tcaagaagat cctttgatct tttctacggg gtctgacgct cagtggaacg    5460
aaaactcacg ttaagggatt ttggtcatga gattatcaaa aaggatcttc acctagatcc    5520
ttttaaatta aaaatgaagt tttaaatcaa tctaaagtat atatgagtaa acttggtctg    5580
acagttacca atgcttaatc agtgaggcac ctatctcagc gatctgtcta tttcgttcat    5640
```

-continued

| | | | | |
|---|---|---|---|---|
| ccatagttgc | ctgactcccc | gtcgtgtaga | taactacgat | acgggagggc ttaccatctg | 5700 |
| gccccagtgc | tgcaatgata | ccgcgagacc | cacgctcacc | ggctccagat ttatcagcaa | 5760 |
| taaaccagcc | agccggaagg | gccgagcgca | gaagtggtcc | tgcaacttta tccgcctcca | 5820 |
| tccagtctat | taattgttgc | cgggaagcta | gagtaagtag | ttcgccagtt aatagtttgc | 5880 |
| gcaacgttgt | tgccattgct | gcaggcatcg | tggtgtcacg | ctcgtcgttt ggtatggctt | 5940 |
| cattcagctc | cggttcccaa | cgatcaaggc | gagttacatg | atcccccatg ttgtgcaaaa | 6000 |
| aagcggttag | ctccttcggt | cctccgatcg | ttgtcagaag | taagttggcc gcagtgttat | 6060 |
| cactcatggt | tatggcagca | ctgcataatt | ctcttactgt | catgccatcc gtaagatgct | 6120 |
| tttctgtgac | tggtgagtac | tcaaccaagt | cattctgaga | atagtgtatg cggcgaccga | 6180 |
| gttgctcttg | cccggcgtca | acacgggata | ataccgcgcc | acatagcaga actttaaaag | 6240 |
| tgctcatcat | tggaaaacgt | tcttcggggc | gaaaactctc | aaggatctta ccgctgttga | 6300 |
| gatccagttc | gatgtaaccc | actcgtgcac | ccaactgatc | ttcagcatct tttactttca | 6360 |
| ccagcgtttc | tgggtgagca | aaaacaggaa | ggcaaaatgc | cgcaaaaaag gaataagggg | 6420 |
| cgacacggaa | atgttgaata | ctcatactct | tcctttttca | atattattga agcatttatc | 6480 |
| agggttattg | tctcatgagc | ggatacatat | ttgaatgtat | ttagaaaaat aaacaaatag | 6540 |
| gggttccgcg | cacatttccc | cgaaaagtgc | cacctgacgt | ctaagaaacc attattatca | 6600 |
| tgacattaac | ctataaaaat | aggcgtatca | cgaggccctt | tcgtcttcaa gaattccacg | 6660 |
| gactatagac | tatactagta | tactccgtct | actgtacgat | acacttccgc tcaggtcctt | 6720 |
| gtcctttaac | gaggccttac | cactcttttg | ttactctatt | gatccagctc agcaaaggca | 6780 |
| gtgtgatcta | agattctatc | ttcgcgatgt | agtaaaacta | gctagaccga gaaagagact | 6840 |
| agaaatgcaa | aaggcacttc | tacaatggct | gccatcatta | ttatccgatg tgacgctgca | 6900 |
| gaagcagaaa | tacacgcgt | cagtgaagct | attccgctat | tgaataaccct cagtcacctt | 6960 |
| gtgcaagaac | ttaacaagaa | accaattatt | aaaggcttac | ttactgatag tagatcaacg | 7020 |
| atcagtataa | ttaagtctac | aaatgaagag | aaatttagaa | acagattttt tggcacaaag | 7080 |
| gcaatgagac | ttagagatga | agtatcaggt | aataatttat | acgtatacta catcgagacc | 7140 |
| aagaagaaca | ttgctgatgt | gatgacaaaa | cctcttccga | taaaaacatt taaactatta | 7200 |
| actaacaaat | ggattcatta | gatctattac | attatgggtg | gtatgttgga ataaaaatca | 7260 |
| actatcatct | actaactagt | atttacgtta | ctagtatatt | atcatatacg gtgttagaag | 7320 |
| atgacgcaaa | tgatgagaaa | tagtcatcta | aattagtgga | agctgaaacg caaggattga | 7380 |
| taatgtaata | ggatcaatga | atattaacat | ataaaatgat | gataataata tttatagaat | 7440 |
| tgtgtagaat | tgcagattcc | ctttttatgga | ttcctaaatc | ctcgaggaga acttctagta | 7500 |
| tatctacata | cctaatatta | ttgccttatt | aaaaatggaa | tcccaacaat tacatcaaaa | 7560 |
| tccacattct | cttcaaaatc | aattgtcctg | tacttccttg | ttcatgtgtg ttcaaaaacg | 7620 |
| ttatatttat | aggataatta | tactctattt | ctcaacaagt | aattggttgt ttggccgagc | 7680 |
| ggtctaaggc | gcctgattca | agaaatatct | tgaccgcagt | taactgtggg aatactcagg | 7740 |
| tatcgtaaga | tgcaagagtt | cgaatctctt | agcaaccatt | attttttcc tcaacataac | 7800 |
| gagaacacac | agggggcgcta | tcgcacagaa | tcaaattcga | tgactgggaa ttttttgtta | 7860 |
| atttcagagg | tcgcctgacg | catatacctt | tttcaactga | aaaattggga gaaaaggaa | 7920 |
| aggtgagagc | cgcggaaccg | gcttttcata | tagaatagag | aagcgttcat gactaaatgc | 7980 |
| ttgcatcaca | atacttgaag | ttgacaatat | tatttaagga | cctattgttt tttccaatag | 8040 |

-continued

```
gtggttagca atcgtcttac tttctaactt ttcttacctt ttacatttca gcaatatata      8100
tatatatatt tcaaggatat accattctaa tgtctgcccc taagaagatc gtcgttttgc      8160
caggtgacca cgttggtcaa gaaatcacag ccgaagccat taaggttctt aaagctattt      8220
ctgatgttcg ttccaatgtc aagttcgatt tcgaaaatca tttaattggt ggtgctgcta      8280
tcgatgctac aggtgtccca cttccagatg aggcgctgga agcctccaag aaggttgatg      8340
ccgttttgtt aggtgctgtg ggtggtccta atgggggtac cggtagtgtt agacctgaac      8400
aaggtttact aaaaatccgt aaagaacttc aattgtacgc caacttaaga ccatgtaact      8460
ttgcatccga ctctctttta gacttatctc caatcaagcc acaatttgct aaaggtactg      8520
acttcgttgt tgtcagagaa ttagtgggag gtatttactt tggtaagaga aaggaagacg      8580
atggtgatgg tgtcgcttgg gatagtgaac aatacaccgt tccagaagtg caaagaatca      8640
caagaatggc cgctttcatg gccctacaac atgagccacc attgcctatt ggtccttgg      8700 ataaagctaa tgttttggcc tcttcaagat tatggagaaa aactgtggag gaaaccatca      8760
agaacgaatt ccctacattg aaggttcaac atcaattgat tgattctgcc gccatgatcc      8820
tagttaagaa cccaacccac ctaaatggta ttataatcac cagcaacatg tttggtgata      8880
tcatctccga tgaagcctcc gttatcccag gttccttggg tttgttgcca tctgcgtcct      8940
tggcctcttt gccagacaag aacaccgcat ttggttttgta cgaaccatgc cacggttctg      9000
ctccagattt gccaaagaat aaggtcaacc ctatcgccac tatcttgtct gctgcaatga      9060
tgttgaaatt gtcattgaac ttgcctgaag aaggtaaggc cattgaagat gcagttaaaa      9120
aggttttgga tgcaggtatc agaactggtg atttaggtgg ttccaacagt accacggaag      9180
tcggtgatgc tgtcgccgaa gaagttaaga aaatccttgc ttaaaaagat tctctttttt      9240
tatgatattt gtacataaac tttataaatg aaattcataa tagaaacgac acgaaattac      9300
aaaatggaat atgttcatag ggtagacgaa actatatacg caatctacat acatttatca      9360
agaaggagaa aaaggaggat gtaaaggaat acagtaagc aaattgatac taatggctca      9420
acgtgataag gaaaaagaat tgcactttaa cattaatatt gacaaggagg agggcaccac      9480
acaaaaagtt aggtgtaaca gaaaatcatg aaactatgat tcctaattta tatattggag      9540
gattttctct aaaaaaaaaa aaatacaaca aataaaaaac actcaatgac ctgaccattt      9600
gatggagttt aagtcaatac cttcttgaac catttcccat aatggtgaaa gttccctcaa      9660 gaatttttact ctgtcagaaa cggccttaac gacgtagtcg acctcctctt cagtactaaa      9720
tctaccaata ccaaatctga tggaagaatg ggctaatgca tcatccttac ccagcgcatg      9780
taaaacataa gaaggttcta gggaagcaga tgtacaggct gaacccgagg ataatgcgat      9840
atcccttagt gccatcaata aagattctcc ttccacgtag gcgaaagaaa cgttaacaca      9900
ccctggataa cgatgatctg gagatccgtt caacgtggta tgttcagcgg ataatagacc      9960
tttgactaat ttatcggata gtcttttgat gtgagcttgg tcgttgtcaa attctttctt      10020
catcaatctc gcagcttcac caaatcccgc taccaatggg ggggcaaag taccagatct      10080 caatcctctc tcttggccac caccggatag taaaggttct aatctaactc ttggtctcct      10140
tcttacatag atggcaccta ttccctttgg accgtaaatc ttgtgagaag aaattgatag      10200
taaatcaatg ttcatttcat tgacatcaat gtgaatctta ccataggctt gtgcggcgtc      10260
agtatgaaag tagatcttat tctttctaca aattgcacca atttctttaa taggttgaat      10320
gacaccgatt tcattattga cagccatcac agagacgaga caggtatctg gtctaatggc      10380
```

-continued

| | | | | |
|---|---|---|---|---|
| atcttccaat | tccttcaaat | cgataagacc | ttgatcgtcc | acatttagga aagtgacttc | 10440 |
| aaatccctcc | ttcatcatgg | cccgtgcggc | ttccaagaca | cacttgtgtt ccgttctagt | 10500 |
| ggtgatgatg | tgtttcttag | tcttcttata | aaatcttggg | acaccttaa gaaccatatt | 10560 |
| attagattcg | gtcgctcccg | aagtgaatat | tatttccttg | gggtcggcat tgatcatctt | 10620 |
| tgctacgtaa | gctctagcat | tttccacagc | agtatttgtt | tcccaaccgt aagagtgagt | 10680 |
| gttggaatga | ggattaccat | aaagtcccgt | ataaaacttc | aacatcgtat ccaaaccct | 10740 |
| agggtctgtt | ggtgtagtgg | cttgcatgtc | aagatatatg | ggacgagtac caaaacctgt | 10800 |
| gttttcttga | taagcatggc | tcattgcagt | gctaccagaa | gctactacag catctggggt | 10860 |
| ggtaccggat | gcactcgcac | gggcactagc | ctgtgccttt | gcagcagcct gaatatcggt | 10920 |
| atgcgtttcc | agagagaagt | tgtcgtctaa | cttcacgcct | gctgcagtct caatgatatt | 10980 |
| cgaatacgct | ttgaggagat | acagcctaat | atccgacaaa | ctgttttaca gatttacgat | 11040 |
| cgtacttgtt | acccatcatt | gaattttgaa | catccgaacc | tgggagtttt ccctgaaaca | 11100 |
| gatagtatat | ttgaacctgt | ataataatat | atagtctagc | gctttacgga agacaatgta | 11160 |
| tgtatttcgg | ttcctggaga | aactattgca | tctattgcat | aggtaatctt gcacgtcgca | 11220 |
| tccccggttc | attttctgcg | tttccatctt | gcacttcaat | agcatatctt tgttaacgaa | 11280 |
| gcatctgtgc | ttcattttgt | agaacaaaaa | tgcaacgcga | gagcgctaat ttttcaaaca | 11340 |
| aagaatctga | gctgcatttt | tacagaacag | aaatgcaacg | cgaaagcgct attttaccaa | 11400 |
| cgaagaatct | gtgcttcatt | tttgtaaaac | aaaaatgcaa | cgcgagagcg ctaatttttc | 11460 |
| aaacaaagaa | tctgagctgc | attttacag | aacagaaatg | caacgcgaga gcgctatttt | 11520 |
| accaacaaag | aatctatact | tcttttttgt | tctacaaaaa | tgcatcccga gagcgctatt | 11580 |
| tttctaacaa | agcatcttag | attactttt | ttctcctttg | tgcgctctat aatgcagtct | 11640 |
| cttgataact | ttttgcactg | taggtccgtt | aaggttagaa | gaaggctact ttggtgtcta | 11700 |
| ttttctcttc | cataaaaaaa | gcctgactcc | acttcccgcg | tttactgatt actagcgaag | 11760 |
| ctgcgggtgc | attttttcaa | gataaaggca | tccccgatta | tattctatac cgatgtggat | 11820 |
| tgcgcatact | ttgtgaacag | aaagtgatag | cgttgatgat | tcttcattgg tcagaaaatt | 11880 |
| atgaacggtt | tcttctatt | tgtctctata | tactacgtat | aggaaatgtt tacattttcg | 11940 |
| tattgttttc | gattcactct | atgaatagtt | cttactacaa | ttttttttgtc taaagagtaa | 12000 |
| tactagagat | aaacataaaa | aatgtagagg | tcgagtttag | atgcaagttc aaggagcgaa | 12060 |
| aggtggatgg | gtaggttata | tagggatata | gcacagagat | atatagcaaa gagatacttt | 12120 |
| tgagcaatgt | ttgtggaagc | ggtattcgca | atatttagt | agctcgttac agtccggtgc | 12180 |
| gtttttggtt | ttttgaaagt | gcgtcttcag | agcgcttttg | gttttcaaaa gcgctctgaa | 12240 |
| gttcctatac | tttctagaga | ataggaactt | cggaatagga | acttcaaagc gtttccgaaa | 12300 |
| acgagcgctt | ccgaaaatgc | aacgcgagct | gcgcacatac | agctcactgt tcacgtcgca | 12360 |
| cctatatctg | cgtgttgcct | gtatatatat | atacatgaga | agaacggcat agtgcgtgtt | 12420 |
| tatgcttaaa | tgcgtactta | tatgcgtcta | tttatgtagg | atgaaaggta gtctagtacc | 12480 |
| tcctgtgata | ttatcccatt | ccatgcgggg | tatcgtatgc | ttccttcagc actaccctt | 12540 |
| agctgttcta | tatgctgcca | ctcctcaatt | ggattagtct | catccttcaa tgctatcatt | 12600 |
| tcctttgata | ttcgatccta | ggcatagtac | cgagaaacta | gtgcgaagta gtgatcaggt | 12660 |
| attgctgtta | tctgatgagt | atacgttgtc | ctggccacgg | cagaagcacg cttatcgctc | 12720 |
| caatttccca | caacattagt | caactccgtt | aggcccttca | ttgaaagaaa tgaggtcatc | 12780 |

<210> SEQ ID NO 23
<211> LENGTH: 11198
<212> TYPE: DNA
<213> ORGANISM: Saccharomyces cerevisiae

<400> SEQUENCE: 23

```
aaatgtcttc caatgtgaga tttttgggcca ttttttatag caaagattga ataaggcgca    12840
tttttcttca                                                           12850 agcttcgcgg ccgccgtctg atttccgttt tgggaatcct ttgccgcgcg cccctctcaa       60
aactccgcac aagtcccaga aagcgggaaa gaaataaaac gccaccaaaa aaaaaaaat       120
aaaagccaat cctcgaagcg tgggtggtag gccctggatt atcccgtaca agtatttctc      180
aggagtaaaa aaaccgtttg ttttggaatt ccccatttcg cggccaccta cgccgctatc      240
tttgcaacaa ctatctgcga taactcagca aattttgcat attcgtgttg cagtattgcg      300
ataatgggag tcttactccc aacataacgg cagaaagaaa tgtgagaaaa ttttgcatcc      360
tttgcctccg ttcaagtata taaagtcggc atgcttgata atctttcttt ccatcctaca      420
ttgttctaat tattcttatt ctcctttatt ctttcctaac ataccaagaa attaatcttc      480
tgtcattcgc ttaaacacta tatcacatat gcggtccgga tccagtttaa acagtagctt      540
tggacttctt cgccagaggt ttggtcaagt ctccaatcaa ggttgtcggc ttgtctacct      600
tgccagaaat ttacgaaaag atggaaaagg gtcaaatcgt tggtagatac gttgttgaca      660
cttctaaata agcgaatttc ttatgattta tgattttat tattaaataa gttataaaaa      720
aaataagtgt atacaaattt taaagtgact cttaggtttt aaaacgaaaa ttcttgttct      780
tgagtaactc tttcctgtag gtcaggttgc tttctcaggt atagcatgag gtcgctctta      840
ttgaccacac tctaccggc atgccgagca aatgcctgca aatcgctccc catttcaccc       900
aattgtagat atgctaactc cagcaatgag ttgatgaatc tcggtgtgta ttttatgtcc      960
tcagaagaca acacctgttg taatcgttct tccacacgga tcgcggccgc ttgatcctct     1020
acgccggacg catcgtggcc ggcatcaccg gcgccacagg tgcggttgct ggcgcctata     1080
tcgccgacat caccgatggg gaagatcggc tcgccacttt cgggctcatg agcgcttgtt     1140
tcggcgtggg tatggtggca ggccccgtgg ccggggggact gttgggcgcc atctccttgc    1200
atgcaccatt ccttgcggcg gcggtgctca acggcctcaa cctactactg ggctgcttcc    1260
taatgcagga gtcgcataag ggagagcgtc gaccgatgcc cttgagagcc ttcaacccag    1320
tcagctcctt ccggtgggcg cggggcatga ctatcgtcgc cgcacttatg actgtcttct    1380
ttatcatgca actcgtagga caggtgccgg cagcgctctg ggtcattttc ggcgaggacc    1440
gctttcgctg gagcgcgacg atgatcggcc tgtcgcttgc ggtattcgga atcttgcacg    1500
ccctcgctca agccttcgtc actggtcccg ccaccaaacg tttcggcgag aagcaggcca    1560
ttatcgccgg catggcggcc gacgcgctgg gctacgtctt gctggcgttc gcgacgcgag    1620
gctggatggc cttccccatt atgattcttc tcgcttccgg cggcatcggg atgcccgcgt    1680
tgcaggccat gctgtccagg caggtagatg acgaccatca gggacagctt caaggatcgc    1740
tcgcggctct taccagccta acttcgatca ctggaccgct gatcgtcacg gcgatttatg    1800
ccgcctcggc gagcacatgg aacgggttgg catggattgt aggcgccgcc ctataccttg    1860
tctgcctccc cgcgttgcgt cgcggtgcat ggagccgggc cacctcgacc tgaatggaag    1920
ccggcggcac ctcgctaacg gattcaccac tccaagaatt ggagccaatc aattcttgcg    1980
```

```
gagaactgtg aatgcgcaaa ccaacccttg gcagaacata tccatcgcgt ccgccatctc   2040
cagcagccgc acgcggcgca tctcgggcag cgttgggtcc tggccacggg tgcgcatgat   2100
cgtgctcctg tcgttgagga cccggctagg ctggcggggt tgccttactg gttagcagaa   2160
tgaatcaccg atacgcgagc gaacgtgaag cgactgctgc tgcaaaacgt ctgcgacctg   2220
agcaacaaca tgaatggtct tcggtttccg tgtttcgtaa agtctggaaa cgcggaagtc   2280
agcgccctgc accattatgt tccggatctg catcgcagga tgctgctggc tacccgtgtg   2340
aacacctaca tctgtattaa cgaagcgctg gcattgaccc tgagtgattt ttctctggtc   2400
ccgccgcatc cataccgcca gttgtttacc ctcacaacgt tccagtaacc gggcatgttc   2460
atcatcagta acccgtatcg tgagcatcct ctctcgtttc atcggtatca ttaccccat    2520 gaacagaaat tccccttac acggaggcat caagtgacca acaggaaaa accgcccttt     2580 aacatggccc gctttatcag aagccagaca ttaacgcttc tggagaaact caacgagctg   2640
gacgcggatg aacaggcaga catctgtgaa tcgcttcacg accacgctga tgagctttac   2700
cgcagctgcc tcgcgcgttt cggtgatgac ggtgaaaacc tctgacacat gcagctcccg   2760
gagacggtca cagcttgtct gtaagcggat gccgggagca gacaagcccg tcagggcgcg   2820
tcagcgggtg ttggcgggtg tcggggcgca gccatgaccc agtcacgtag cgatagcgga   2880
gtgtatactg gcttaactat gcggcatcag agcagattgt actgagagtg cacgatatcc   2940
ggtgtgaaat accgcacaga tgcgtaagga gaaaataccg catcaggcgc tcttccgctt   3000
cctcgctcac tgactcgctg cgctcggtcg ttcggctgcg gcgagcggta tcagctcact   3060
caaaggcggt aatacggtta tccacagaat caggggataa cgcaggaaag aacatgtgag   3120
caaaaggcca gcaaaaggcc aggaaccgta aaaaggccgc gttgctggcg ttttccata    3180 ggctccgccc ccctgacgag catcacaaaa atcgacgctc aagtcagagg tggcgaaacc   3240
cgacaggact ataaagatac caggcgtttc ccctggaag ctcctcgtg cgctctcctg     3300 ttccgaccct gccgcttacc ggatacctgt ccgcctttct cccttcggga agcgtggcgc   3360
tttctcaatg ctcacgctgt aggtatctca gttcggtgta ggtcgttcgc tccaagctgg   3420
gctgtgtgca cgaaccccc gttcagcccg accgctgcgc cttatccggt aactatcgtc    3480
ttgagtccaa cccggtaaga cacgacttat cgccactggc agcagccact ggtaacagga   3540
ttagcagagc gaggtatgta ggcggtgcta cagagttctt gaagtggtgg cctaactacg   3600
gctacactag aaggacagta tttggtatct gcgctctgct gaagccagtt accttcggaa   3660
aaagagttgg tagctcttga tccggcaaac aaaccaccgc tggtagcggt ggtttttttg   3720
tttgcaagca gcagattacg cgcagaaaaa aaggatctca agaagatcct ttgatctttt   3780
ctacggggtc tgacgctcag tggaacgaaa actcacgtta agggatttg gtcatgagat    3840 tatcaaaaag gatcttcacc tagatccttt taaattaaaa atgaagtttt aaatcaatct   3900
aaagtatata tgagtaaact tggtctgaca gttaccaatg cttaatcagt gaggcaccta   3960
tctcagcgat ctgtctattt cgttcatcca tagttgcctg actccccgtc gtgtagataa   4020
ctacgatacg ggagggctta ccatctggcc ccagtgctgc aatgataccg cgagacccac   4080
gctcaccggc tccagattta tcagcaataa accagccagc cggaagggcc gagcgcagaa   4140
gtggtcctgc aactttatcc gcctccatcc agtctattaa ttgttgccgg gaagctagag   4200
taagtagttc gccagttaat agtttgcgca acgttgttgc cattgctgca ggcatcgtgg   4260
tgtcacgctc gtcgtttggt atggcttcat tcagctccgg ttcccaacga tcaaggcgag   4320
ttacatgatc ccccatgttg tgcaaaaaag cggttagctc cttcggtcct ccgatcgttg   4380
```

```
tcagaagtaa gttggccgca gtgttatcac tcatggttat ggcagcactg cataattctc   4440
ttactgtcat gccatccgta agatgctttt ctgtgactgg tgagtactca accaagtcat   4500
tctgagaata gtgtatgcgg cgaccgagtt gctcttgccc ggcgtcaaca cgggataata   4560
ccgcgccaca tagcagaact ttaaaagtgc tcatcattgg aaaacgttct tcggggcgaa   4620
aactctcaag gatcttaccg ctgttgagat ccagttcgat gtaacccact cgtgcaccca   4680
actgatcttc agcatctttt actttcacca gcgtttctgg gtgagcaaaa acaggaaggc   4740
aaaatgccgc aaaaaaggga ataagggcga cacggaaatg ttgaatactc atactcttcc   4800
tttttcaata ttattgaagc atttatcagg gttattgtct catgagcgga tacatatttg   4860
aatgtattta gaaaaataaa caatagggg ttccgcgcac atttcccga aaagtgccac   4920
ctgacgtcta agaaaccatt attatcatga cattaaccta taaaaatagg cgtatcacga   4980
ggccctttcg tcttcaagaa ttccacggac tatagactat actagtatac tccgtctact   5040
gtacgataca cttccgctca ggtccttgtc ctttaacgag gccttaccac tcttttgtta   5100
ctctattgat ccagctcagc aaaggcagtg tgatctaaga ttctatcttc gcatgtagt    5160
aaaactagct agaccgagaa agagactaga aatgcaaaag gcacttctac aatggctgcc   5220
atcattatta tccgatgtga cgctgcagaa gcagaaatac acgcggtcag tgaagctatt   5280
ccgctattga ataacctcag tcaccttgtg caagaactta acaagaaacc aattattaaa   5340
ggcttactta ctgatagtag atcaacgatc agtataatta agtctacaaa tgaagagaaa   5400
tttagaaaca gatttttttgg cacaaaggca atgagactta gagatgaagt atcaggtaat   5460
aatttatacg tatactacat cgagaccaag aagaacattg ctgatgtgat gacaaaaacct  5520
cttccgataa aaacatttaa actattaact aacaaatgga ttcattagat ctattacatt   5580
atgggtggta tgttggaata aaaatcaact atcatctact aactagtatt tacgttacta   5640
gtatattatc atatacggtg ttagaagatg acgcaaatga tgagaaatag tcatctaaat   5700
tagtggaagc tgaaacgcaa ggattgataa tgtaatagga tcaatgaata ttaacatata   5760
aaatgatgat aataatattt atagaattgt gtagaattgc agattccctt ttatggattc   5820
ctaaatcctc gaggagaact tctagtatat ctacatacct aatattattg ccttattaaa   5880
aatggaatcc caacaattac atcaaaatcc acattctctt caaaatcaat tgtcctgtac   5940
ttccttgttc atgtgtgttc aaaaacgtta tatttatagg ataattatac tctatttctc   6000
aacaagtaat tggttgtttg gccgagcggt ctaaggcgcc tgattcaaga aatatcttga   6060
ccgcagttaa ctgtgggaat actcaggtat cgtaagatgc aagagttcga atctcttagc   6120
aaccattatt tttttcctca acataacgag aacacacagg ggcgctatcg cacagaatca   6180
aattcgatga ctggaaattt tttgttaatt tcagaggtcg cctgacgcat atacctttt    6240
caactgaaaa attgggagaa aaaggaaagg tgagagccgc ggaaccggct tttcatatag   6300
aatagagaag cgttcatgac taaatgcttg catcacaata cttgaagttg acaatattat   6360
ttaaggacct attgttttt ccaataggtg gttagcaatc gtcttacttt ctaacttttc    6420
ttacctttta catttcagca atatatatat atatatttca aggatatacc attctaatgt   6480
ctgcccctaa gaagatcgtc gttttgccag gtgaccacgt tggtcaagaa atcacagccg   6540
aagccattaa ggttcttaaa gctatttctg atgttcgttc caatgtcaag ttcgatttcg   6600
aaaatcattt aattggtggt gctgctatcg atgctacagg tgtcccactt ccagatgagg   6660
cgctggaagc ctccaagaag gttgatgccg ttttgttagg tgctgtgggt ggtcctaaat   6720
```

```
                                   -continued ggggtaccgg tagtgttaga cctgaacaag gtttactaaa aatccgtaaa gaacttcaat    6780
tgtacgccaa cttaagacca tgtaactttg catccgactc tcttttagac ttatctccaa    6840
tcaagccaca atttgctaaa ggtactgact tcgttgttgt cagagaatta gtgggaggta    6900
tttactttgg taagagaaag gaagacgatg gtgatggtgt cgcttgggat agtgaacaat    6960
acaccgttcc agaagtgcaa agaatcacaa gaatggccgc tttcatggcc ctacaacatg    7020
agccaccatt gcctatttgg tccttggata aagctaatgt tttggcctct tcaagattat    7080
ggagaaaaac tgtggaggaa accatcaaga acgaattccc tacattgaag gttcaacatc    7140
aattgattga ttctgccgcc atgatcctag ttaagaaccc aacccaccta aatggtatta    7200
taatcaccag caacatgttt ggtgatatca tctccgatga agcctccgtt atcccaggtt    7260
ccttgggttt gttgccatct gcgtccttgg cctctttgcc agacaagaac accgcatttg    7320
gtttgtacga accatgccac ggttctgctc cagatttgcc aaagaataag gtcaaccctg    7380
tcgccactat cttgtctgct gcaatgatgt tgaaattgtc attgaacttg cctgaagaag    7440
gtaaggccat tgaagatgca gttaaaaagg ttttggatgc aggtatcaga actggtgatt    7500
taggtggttc caacagtacc acggaagtcg gtgatgctgt cgccgaagaa gttaagaaaa    7560
tccttgctta aaaagattct cttttttttat gatatttgta cataaacttt ataaatgaaa    7620
ttcataatag aaacgacacg aaattacaaa atggaatatg ttcataggt agacgaaact     7680 atatacgcaa tctacataca tttatcaaga aggagaaaaa ggaggatgta aggaataca    7740 ggtaagcaaa ttgatactaa tggctcaacg tgataaggaa aaagaattgc actttaacat    7800
taatattgac aaggaggagg gcaccacaca aaaagttagg tgtaacagaa atcatgaaa     7860 ctatgattcc taatttatat attggaggat tttctctaaa aaaaaaaaa tacaacaaat    7920 aaaaaacact caatgacctg accatttgat ggagtttaag tcaataccctt cttgaaccat    7980 ttcccataat ggtgaaagtt ccctcaagaa ttttactctg tcagaaacgg ccttaacgac    8040
gtagtcgacc tcctcttcag tactaaatct accaatacca aatctgatgg aagaatgggc    8100
taatgcatca tccttaccca gcgcatgtaa aacataagaa ggttctaggg aagcagatgt    8160
acaggctgaa cccgaggata atgcgatatc ccttagtgcc atcaataaag attctccttc    8220
cacgtaggcg aaagaaacgt taacacaccc tggataacga tgatctggag atccgttcaa    8280
cgtggtatgt tcagcggata atagaccttt gactaattta tcggatagtc ttttgatgtg    8340
agcttggtcg ttgtcaaatt cttttcttcat caatctcgca gcttccaa atcccgctac    8400 caatgggggg gccaaagtac cagatctcaa tcctctctct tggccaccac cggatagtaa    8460
aggttctaat ctaactcttg gtctccttct tacatagatg gcacctattc cctttggacc    8520
gtaaatcttg tgagaagaaa ttgatagtaa atcaatgttc atttcattga catcaatgtg    8580
aatcttacca taggcttgtg cggcgtcagt atgaaagtag atcttattct ttctacaaat    8640
tgcaccaatt tctttaatag gttgaatgac accgatttca ttattgacag ccatcacaga    8700
gacgagacag gtatctggtc taatggcatc ttccaattcc ttcaaatcga taagaccttg    8760
atcgtccaca tttaggaaag tgacttcaaa tccctccttc atcatggccc gtgcggcttc    8820
caagacacac ttgtgttccg ttctagtggt gatgatgtgt ttcttagtct tcttataaaa    8880
tcttgggaca cccttaagaa ccatattatt agattcggtc gctcccgaag tgaatattat    8940
ttccttgggg tcggcattga tcatcttttc tacgtaagct ctagcatttt ccacagcagt    9000
atttgtttcc caaccgtaag agtgagtgtt ggaatgagga ttaccataaa gtcccgtata    9060
aaacttcaac atcgtatcca aaaccctagg gtctgttggt gtagtggctt gcatgtcaag    9120
```

```
atatatggga cgagtaccaa aacctgtgtt tccttgataa gcatggctca ttgcagtgct    9180
accagaagct actacagcat ctggggtggt accggatgca ctcgcacggg cactagcctg    9240
tgcctttgca gcagcctgaa tatcggtatg cgtttccaga gagaagttgt cgtctaactt    9300
cacgcctgct gcagtctcaa tgatattcga atacgctttg aggagataca gcctaatatc    9360
cgacaaactg ttttacagat ttacgatcgt acttgttacc catcattgaa ttttgaacat    9420
ccgaacctgg gagttttccc tgaaacagat agtatatttg aacctgtata ataatatata    9480
gtctagcgct ttacggaaga caatgtatgt atttcggttc ctggagaaac tattgcatct    9540
attgcatagg taatcttgca cgtcgcatcc ccggttcatt ttctgcgttt ccatcttgca    9600
cttcaatagc atatctttgt taacgaagca tctgtgcttc attttgtaga acaaaaatgc    9660
aacgcgagag cgctaatttt tcaaacaaag aatctgagct gcatttttac agaacagaaa    9720
tgcaacgcga aagcgctatt ttaccaacga agaatctgtg cttcattttt gtaaaacaaa    9780
aatgcaacgc gagagcgcta atttttcaaa caaagaatct gagctgcatt tttacagaac    9840
agaaatgcaa cgcgagagcg ctattttacc aacaaagaat ctatacttct tttttgttct    9900
acaaaaatgc atcccgagag cgctattttt ctaacaaagc atcttagatt acttttttc     9960
tcctttgtgc gctctataat gcagtctctt gataacttttt tgcactgtag gtccgttaag   10020
gttagaagaa ggctactttg gtgtctattt tctcttccat aaaaaagcc tgactccact     10080
tcccgcgttt actgattact agcgaagctg cgggtgcatt ttttcaagat aaaggcatcc   10140
ccgattatat tctataccga tgtggattgc gcatactttg tgaacagaaa gtgatagcgt   10200
tgatgattct tcattggtca gaaaattatg aacggtttct tctattttgt ctctatatac   10260
tacgtatagg aaatgtttac attttcgtat tgttttcgat tcactctatg aatagttctt   10320
actacaattt ttttgtctaa agagtaatac tagagataaa cataaaaaat gtagaggtcg   10380
agtttagatg caagttcaag gagcgaaagg tggatgggta ggttatatag ggatatagca   10440
cagagatata tagcaaagag atactttga gcaatgtttg tggaagcggt attcgcaata   10500
ttttagtagc tcgttacagt ccggtgcgtt tttggttttt tgaaagtgcg tcttcagagc   10560
gcttttggtt ttcaaaagcg ctctgaagtt cctatacttt ctagagaata ggaacttcgg   10620
aataggaact tcaaagcgtt tccgaaaacg agcgcttccg aaaatgcaac gcgagctgcg   10680
cacatacagc tcactgttca cgtcgcacct atatctgcgt gttgcctgta tatatatata   10740
catgagaaga acggcatagt gcgtgtttat gcttaaatgc gtacttatat gcgtctattt   10800
atgtaggatg aaaggtagtc tagtacctcc tgtgatatta tcccattcca tgcgggtat    10860
cgtatgcttc cttcagcact accctttagc tgttctatat gctgccactc ctcaattgga   10920
ttagtctcat ccttcaatgc tatcatttcc tttgatattc gatcctaggc atagtaccga   10980
gaaactagtg cgaagtagtg atcaggtatt gctgttatct gatgagtata cgttgtcctg   11040
gccacggcag aagcacgctt atcgctccaa tttcccacaa cattagtcaa ctccgttagg   11100
cccttcattg aaagaaatga ggtcatcaaa tgtcttccaa tgtgagattt tgggccattt   11160
tttatagcaa agattgaata aggcgcattt ttcttcaa                           11198
```

<210> SEQ ID NO 24
<211> LENGTH: 11427
<212> TYPE: DNA
<213> ORGANISM: Saccharomyces cerevisiae

<400> SEQUENCE: 24

-continued

| | |
|---|---|
| agcttcgcgg ccgcctttcg attagcacgc acacacatca catagactgc gtcataaaaa | 60 |
| tacactacgg aaaaaccata aagagcaaag cgatacctac ttggaaggaa aaggagcacg | 120 |
| cttgtaaggg ggatgggggc taagaagtca ttcactttct tttcccttcg cggtccggac | 180 |
| ccgggacccc tcctctcccc gcacgatttc ttccttcat atcttccttt tattcctatc | 240 |
| ccgttgaagc aaccgcacta tgactaaatg gtgctggaca tctccatggc tgtgacttgt | 300 |
| gtgtatctca cagtggtaac ggcaccgtgg ctcggaaacg gttccttcgt gacaattcta | 360 |
| gaacaggggc tacagtctcg ataatagaat aataagcgca tttttgctag cgccgccgcg | 420 |
| gcgcccgttt cccaataggg aggcgcagtt tatcggcgga gctctacttc ttcctatttg | 480 |
| ggtaagcccc tttctgtttt cggccagtgg ttgctgcagg ctgcgccgga aacatagtg | 540 |
| ataagggatg taactttcga tgagagaatt agcaagcgga aaaaaactat ggctagctgg | 600 |
| gagttgtttt tcaatcatat aaagggaga aattgttgct cactatgtga cagtttctgg | 660 |
| gacgtcttaa cttttattgc agaggactat caaatcatac agatattgtc aaaaaaaaaa | 720 |
| aagactaata ataacatatg cggtccggat ccagtttaaa cagtagcttt ggacttcttc | 780 |
| gccagaggtt tggtcaagtc tccaatcaag gttgtcggct tgtctacctt gccagaaatt | 840 |
| tacgaaaaga tggaaaaggg tcaaatcgtt ggtagatacg ttgttgacac ttctaaataa | 900 |
| gcgaatttct tatgatttat gatttttatt attaaataag ttataaaaaa aataagtgta | 960 |
| tacaaatttt aaagtgactc ttaggttttta aaacgaaaat tcttgttctt gagtaactct | 1020 |
| ttcctgtagg tcaggttgct ttctcaggta tagcatgagg tcgctcttat tgaccacacc | 1080 |
| tctaccggca tgccgagcaa atgcctgcaa atcgctcccc atttcaccca attgtagata | 1140 |
| tgctaactcc agcaatgagt tgatgaatct cggtgtgtat tttatgtcct cagaagacaa | 1200 |
| cacctgttgt aatcgttctt ccacacggat cgcggccgct tgatcctcta cgccggacgc | 1260 |
| atcgtggccg gcatcaccgg cgccacaggt gcggttgctg cgcctatat cgccgacatc | 1320 |
| accgatgggg aagatcgggc tcgccacttc gggctcatga gcgcttgttt cggcgtgggt | 1380 |
| atggtggcag gccccgtggc cggggactg ttgggcgcca tctccttgca tgcaccattc | 1440 |
| cttgcggcgg cggtgctcaa cggcctcaac ctactactgg gctgcttcct aatgcaggag | 1500 |
| tcgcataagg gagagcgtcg accgatgccc ttgagagcct tcaacccagt cagctccttc | 1560 |
| cggtgggcgc ggggcatgac tatcgtcgcc gcacttatga ctgtcttctt tatcatgcaa | 1620 |
| ctcgtaggac aggtgccggc agcgctctgg gtcattttcg gcgaggaccg ctttcgctgg | 1680 |
| agcgcgacga tgatcggcct gtcgcttgcg gtattcggaa tcttgcacgc cctcgctcaa | 1740 |
| gccttcgtca ctggtcccgc caccaaacgt ttcggcgaga gcaggccat tatcgccggc | 1800 |
| atggcggccg acgcgctggg ctacgtcttg ctggcgttcg cgacgcgagg ctggatggcc | 1860 |
| ttccccatta tgattcttct cgcttccggc ggcatcggga tgcccgcgtt gcaggccatg | 1920 |
| ctgtccaggc aggtagatga cgaccatcag ggacagcttc aaggatcgct cgcggctctt | 1980 |
| accagcctaa cttcgatcac tggaccgctg atcgtcacgg cgatttatgc cgcctcggcg | 2040 |
| agcacatgga acgggttggc atggattgta ggcgccgccc tataccttgt ctgcctcccc | 2100 |
| gcgttgcgtc gcggtgcatg gagccgggcc acctcgacct gaatggaagc cggcggcacc | 2160 |
| tcgctaacgg attcaccact ccaagaattg gagccaatca attcttgcgg agaactgtga | 2220 |
| atgcgcaaac caacccttgg cagaacatat ccatcgcgtc cgccatctcc agcagccgca | 2280 |
| cgcggcgcat ctcgggcagc gttgggtcct ggccacgggt gcgcatgatc gtgctcctgt | 2340 |
| cgttgaggac ccggctaggc tggcggggtt gccttactgg ttagcagaat gaatcaccga | 2400 |

-continued

```
tacgcgagcg aacgtgaagc gactgctgct gcaaaacgtc tgcgacctga gcaacaacat    2460
gaatggtctt cggtttccgt gtttcgtaaa gtctggaaac gcggaagtca gcgccctgca    2520
ccattatgtt ccggatctgc atcgcaggat gctgctggct accctgtgga acacctacat    2580
ctgtattaac gaagcgctgg cattgaccct gagtgatttt tctctggtcc cgccgcatcc    2640
ataccgccag ttgtttaccc tcacaacgtt ccagtaaccg ggcatgttca tcatcagtaa    2700
cccgtatcgt gagcatcctc tctcgtttca tcggtatcat taccccatg aacagaaatt    2760 ccccctaca cggaggcatc aagtgaccaa acaggaaaaa accgcccta acatggcccg    2820 ctttatcaga agccagacat taacgcttct ggagaaactc aacgagctgg acgcggatga    2880
acaggcagac atctgtgaat cgcttcacga ccacgctgat gagctttacc gcagctgcct    2940
cgcgcgtttc ggtgatgacg gtgaaaacct ctgacacatg cagctcccgg agacggtcac    3000
agcttgtctg taagcggatg ccgggagcag acaagcccgt cagggcgcgt cagcgggtgt    3060
tggcgggtgt cggggcgcag ccatgaccca gtcacgtagc gatagcggag tgtatactgg    3120
cttaactatg cggcatcaga gcagattgta ctgagagtgc acgatatccg gtgtgaaata    3180
ccgcacagat gcgtaaggag aaaataccgc atcaggcgct cttccgcttc ctcgctcact    3240
gactcgctgc gctcggtcgt tcggctgcgg cgagcggtat cagctcactc aaaggcggta    3300
atacggttat ccacagaatc aggggataac gcaggaaaga acatgtgagc aaaaggccag    3360
caaaaggcca ggaaccgtaa aaaggccgcg ttgctggcgt ttttccatag gctccgcccc    3420
cctgacgagc atcacaaaaa tcgacgctca agtcagaggt ggcgaaaccc gacaggacta    3480
taaagatacc aggcgtttcc ccctggaagc tccctcgtgc gctctcctgt tccgaccctg    3540
ccgcttaccg gatacctgtc cgcctttctc ccttcgggaa gcgtggcgct ttctcaatgc    3600
tcacgctgta ggtatctcag ttcggtgtag gtcgttcgct ccaagctggg ctgtgtgcac    3660
gaaccccccg ttcagcccga ccgctgcgcc ttatccggta actatcgtct tgagtccaac    3720
ccggtaagac acgacttatc gccactggca gcagccactg gtaacaggat tagcagagcg    3780
aggtatgtag gcggtgctac agagttcttg aagtggtggc ctaactacgg ctacactaga    3840
aggacagtat ttggtatctg cgctctgctg aagccagtta ccttcggaaa aagagttggt    3900
agctcttgat ccggcaaaca aaccaccgct ggtagcggtg ttttttttgt ttgcaagcag    3960
cagattacgc gcagaaaaaa aggatctcaa gaagatcctt tgatctttct tacgggtct    4020 gacgctcagt ggaacgaaaa ctcacgttaa gggattttgg tcatgagatt atcaaaaagg    4080
atcttcacct agatcctttt aaattaaaaa tgaagtttta aatcaatcta agtatatat    4140 gagtaaactt ggtctgacag ttaccaatgc ttaatcagtg aggcacctat ctcagcgatc    4200
tgtctatttc gttcatccat agttgcctga ctccccgtcg tgtagataac tacgatacgg    4260
gagggcttac catctggccc cagtgctgca atgataccgc gagacccacg ctcaccggct    4320
ccagatttat cagcaataaa ccagccagcc ggaagggccg agcgcagaag tggtcctgca    4380
actttatccg cctccatcca gtctattaat tgttgccggg aagctagagt aagtagttcg    4440
ccagttaata gtttgcgcaa cgttgttgcc attgctgcag gcatcgtggt gtcacgctcg    4500
tcgtttggta tggcttcatt cagctccggt tcccaacgat caaggcgagt tacatgatcc    4560
cccatgttgt gcaaaaaagc ggttagctcc ttcggtcctc cgatcgttgt cagaagtaag    4620
ttggccgcag tgttatcact catggttatg gcagcactgc ataattctct tactgtcatg    4680
ccatccgtaa gatgcttttc tgtgactggt gagtactcaa ccaagtcatt ctgagaatag    4740
```

-continued

```
tgtatgcggc gaccgagttg ctcttgcccg gcgtcaacac gggataatac cgcgccacat    4800
agcagaactt taaaagtgct catcattgga aaacgttctt cggggcgaaa actctcaagg    4860
atcttaccgc tgttgagatc cagttcgatg taacccactc gtgcacccaa ctgatcttca    4920
gcatctttta ctttcaccag cgtttctggg tgagcaaaaa caggaaggca aaatgccgca    4980
aaaaagggaa taagggcgac acggaaatgt tgaatactca tactcttcct ttttcaatat    5040
tattgaagca tttatcaggg ttattgtctc atgagcggat acatatttga atgtatttag    5100
aaaaataaac aaatagggt tccgcgcaca tttccccgaa aagtgccacc tgacgtctaa    5160
gaaaccatta ttatcatgac attaacctat aaaaataggc gtatcacgag gccctttcgt    5220
cttcaagaat tccacggact atagactata ctagtatact ccgtctactg tacgatacac    5280
ttccgctcag gtccttgtcc tttaacgagg ccttaccact cttttgttac tctattgatc    5340
cagctcagca aaggcagtgt gatctaagat tctatcttcg cgatgtagta aaactagcta    5400
gaccgagaaa gagactagaa atgcaaaagg cacttctaca atggctgcca tcattattat    5460
ccgatgtgac gctgcagaag cagaaataca cgcggtcagt gaagctattc cgctattgaa    5520
taacctcagt caccttgtgc aagaacttaa caagaaacca attattaaag gcttacttac    5580
tgatagtaga tcaacgatca gtataattaa gtctacaaat gaagagaaat ttagaaacag    5640
attttttggc acaaaggcaa tgagacttag agatgaagta tcaggtaata atttatacgt    5700 atactcatc gagaccaaga gaacattgc tgatgtgatg acaaaacctc ttccgataaa    5760
aacatttaaa ctattaacta acaaatggat tcattagatc tattacatta tgggtggtat    5820
gttggaataa aaatcaacta tcatctacta actagtattt acgttactag tatattatca    5880
tatacggtgt tagaagatga cgcaaatgat gagaaatagt catctaaatt agtggaagct    5940
gaaacgcaag gattgataat gtaataggat caatgaatat taacatataa aatgatgata    6000
ataatattta tagaattgtg tagaattgca gattcccttt tatggattcc taaatcctcg    6060
aggagaactt ctagtatatc tacataccta atattattgc cttattaaaa atggaatccc    6120
aacaattaca tcaaatcca cattctcttc aaaatcaatt gtcctgtact ccttgttca    6180 tgtgtgttca aaaacgttat atttatagga taattatact ctatttctca acaagtaatt    6240
ggttgtttgg ccgagcggtc taaggcgcct gattcaagaa atatcttgac cgcagttaac    6300
tgtgggaata ctcaggtatc gtaagatgca agagttcgaa tctcttagca accattattt    6360
ttttcctcaa cataacgaga acacacaggg gcgctatcgc acagaatcaa attcgatgac    6420
tggaaatttt ttgttaattt cagaggtcgc ctgacgcata tacctttttc aactgaaaaa    6480
ttgggagaaa aaggaaaggt gagagccgcg gaaccggctt tcatataga atagagaagc    6540 gttcatgact aaatgcttgc atcacaatac ttgaagttga caatattatt taaggaccta    6600
ttgttttttc caataggtgg ttagcaatcg tcttacttc taactttct tacctttac    6660 atttcagcaa tatatatata tatatttcaa ggatatacca ttctaatgtc tgcccctaag    6720
aagatcgtcg ttttgccagg tgaccacgtt ggtcaagaaa tcacagccga agccattaag    6780
gttcttaaag ctatttctga tgttcgttcc aatgtcaagt tcgatttcga aaatcattta    6840
attggtggtg ctgctatcga tgctacaggt gtcccactc cagatgaggc gctggaagcc    6900
tccaagaagg ttgatgccgt tttgttaggt gctgtgggtg gtcctaaatg gggtaccggt    6960
agtgttagac ctgaacaagg tttactaaaa atccgtaaag aacttcaatt gtacgccaac    7020
ttaagaccat gtaactttgc atccgactct cttttagact tatctccaat caagccacaa    7080
tttgctaaag gtactgactt cgttgttgtc agagaattag tgggaggtat ttactttggt    7140
```

```
aagagaaagg aagacgatgg tgatggtgtc gcttgggata gtgaacaata caccgttcca   7200
gaagtgcaaa gaatcacaag aatggccgct ttcatggccc tacaacatga gccaccattg   7260
cctatttggt ccttggataa agctaatgtt ttggcctctt caagattatg gagaaaaact   7320
gtggaggaaa ccatcaagaa cgaattccct acattgaagg ttcaacatca attgattgat   7380
tctgccgcca tgatcctagt taagaaccca acccacctaa atggtattat aatcaccagc   7440
aacatgtttg gtgatatcat ctccgatgaa gcctccgtta tcccaggttc cttgggtttg   7500
ttgccatctg cgtccttggc ctcttttgcca gacaagaaca ccgcatttgg tttgtacgaa   7560
ccatgccacg gttctgctcc agatttgcca aagaataagg tcaaccctat cgccactatc   7620
ttgtctgctg caatgatgtt gaaattgtca ttgaacttgc ctgaagaagg taaggccatt   7680
gaagatgcag ttaaaaaggt tttggatgca ggtatcagaa ctggtgattt aggtggttcc   7740
aacagtacca cggaagtcgg tgatgctgtc gccgaagaag ttaagaaaat ccttgcttaa   7800
aaagattctc tttttttatg atatttgtac ataaacttta taatgaaat tcataataga   7860 aacgacacga aattacaaaa tggaatatgt tcatagggta gacgaaacta tatacgcaat   7920
ctacatacat ttatcaagaa ggagaaaaag gaggatgtaa aggaatacag gtaagcaaat   7980
tgatactaat ggctcaacgt gataaggaaa aagaattgca cttaacatt aatattgaca   8040 aggaggaggg caccacacaa aaagttaggt gtaacagaaa atcatgaaac tatgattcct   8100
aatttatata ttggaggatt ttctctaaaa aaaaaaaaat acaacaaata aaaaacactc   8160
aatgacctga ccatttgatg gagtttaagt caataccttc ttgaaccatt tcccataatg   8220
gtgaaagttc cctcaagaat tttactctgt cagaaacggc cttaacgacg tagtcgacct   8280
cctcttcagt actaaatcta ccaataccaa atctgatgga agaatgggct aatgcatcat   8340
ccttacccag cgcatgtaaa acataagaag gttctaggga agcagatgta caggctgaac   8400
ccgaggataa tgcgatatcc cttagtgcca tcaataaaga ttctccttcc acgtaggcga   8460
aagaaacgtt aacacaccct ggataacgat gatctggaga tccgttcaac gtggtatgtt   8520
cagcggataa tagaccttg actaatttat cggatagtct tttgatgtga gcttggtcgt   8580
tgtcaaattc tttcttcatc aatctcgcag cttcaccaaa tcccgctacc aatgggggg   8640 ccaaagtacc agatctcaat cctctctctt ggccaccacc ggatagtaaa ggttctaatc   8700
taactcttgg tctccttctt acatagatgg cacctattcc ctttggaccg taaatcttgt   8760
gagaagaaat tgatagtaaa tcaatgttca tttcattgac atcaatgtga atcttaccat   8820
aggcttgtgc ggcgtcagta tgaaagtaga tcttattctt tctacaaatt gcaccaattt   8880
ctttaatagg ttgaatgaca ccgatttcat tattgacagc catcacagag acgagacagg   8940
tatctggtct aatggcatct tccaattcct tcaaatcgat aagaccttga tcgtccacat   9000
ttaggaaagt gacttcaaat ccctccttca tcatggcccg tgcggcttcc aagacacact   9060
tgtgttccgt tctagtggtg atgatgtgtt tcttagtctt cttataaaat cttgggacac   9120
ccttaagaac catattatta gattcggtcg ctcccgaagt gaatattatt ccttgggggt   9180
cggcattgat catctttgct acgtaagctc tagcattttc cacagcagta tttgtttccc   9240
aaccgtaaga gtgagtgttg gaatgaggat taccataaag tcccgtataa aacttcaaca   9300
tcgtatccaa aaccctaggg tctgttggtg tagtggcttg catgtcaaga tatatgggac   9360
gagtaccaaa acctgtgttt tcttgataag catggctcat tgcagtgcta ccagaagcta   9420
ctacagcatc tggggtggta ccggatgcac tcgcacgggc actagcctgt gcctttgcag   9480
```

-continued

```
cagcctgaat atcggtatgc gtttccagag agaagttgtc gtctaacttc acgcctgctg   9540
cagtctcaat gatattcgaa tacgctttga ggagatacag cctaatatcc gacaaactgt   9600
tttacagatt tacgatcgta cttgttaccc atcattgaat tttgaacatc cgaacctggg   9660
agttttccct gaaacagata gtatatttga acctgtataa taatatatag tctagcgctt   9720
tacgaaagac aatgtatgta tttcggttcc tggagaaact attgcatcta ttgcataggt   9780
aatcttgcac gtcgcatccc cggttcattt tctgcgtttc catcttgcac ttcaatagca   9840
tatctttgtt aacgaagcat ctgtgcttca ttttgtagaa caaaaatgca acgcgagagc   9900
gctaattttt caaacaaaga atctgagctg catttttaca gaacagaaat gcaacgcgaa   9960
agcgctattt taccaacgaa gaatctgtgc ttcattttg taaaacaaaa atgcaacgcg  10020
agagcgctaa ttttttcaaac aaagaatctg agctgcattt ttacagaaca gaaatgcaac  10080
gcgagagcgc tattttacca acaagaatc tatacttctt ttttgttcta caaaaatgca  10140
tcccgagagc gctattttc taacaaagca tcttagatta cttttttttct cctttgtgcg  10200 ctctataatg cagtctcttg ataactttt gcactgtagg tccgttaagg ttagaagaag  10260
gctactttgg tgtctatttt ctcttccata aaaaaagcct gactccactt cccgcgttta  10320
ctgattacta gcgaagctgc gggtgcattt tttcaagata aaggcatccc cgattatatt  10380
ctataccgat gtggattgcg catactttgt gaacagaaag tgatagcgtt gatgattctt  10440
cattggtcag aaaattatga acggtttctt ctattttgtc tctatatact acgtatagga  10500
aatgtttaca ttttcgtatt gttttcgatt cactctatga atagttctta ctacaatttt  10560
tttgtctaaa gagtaatact agagataaac ataaaaaatg tagaggtcga gtttagatgc  10620
aagttcaagg agcgaaaggt ggatgggtag gttatatagg gatatagcac agagatatat  10680
agcaaagaga tacttttgag caatgtttgt ggaagcggta ttcgcaatat tttagtagct  10740
cgttacagtc cggtgcgttt ttggtttttt gaaagtgcgt cttcagagcg cttttggttt  10800
tcaaaagcgc tctgaagttc ctatactttc tagagaatag gaacttcgga ataggaactt  10860
caaagcgttt ccgaaaacga gcgcttccga aaatgcaacg cgagctgcgc acatacagct  10920
cactgttcac gtcgcaccta tatctgcgtg ttgcctgtat atatatatac atgagaagaa  10980
cggcatagtg cgtgtttatg cttaaatgcg tacttatatg cgtctattta tgtaggatga  11040
aaggtagtct agtacctcct gtgatattat cccattccat gcggggtatc gtatgcttcc  11100
ttcagcacta ccctttagct gttctatatg ctgccactcc tcaattggat tagtctcatc  11160
cttcaatgct atcatttcct ttgatattcg atcctaggca tagtaccgag aaactagtgc  11220
gaagtagtga tcaggtattg ctgttatctg atgagtatac gttgtcctgg ccacggcaga  11280
agcacgctta tcgctccaat ttcccacaac attagtcaac tccgttaggc ccttcattga  11340
aagaaatgag gtcatcaaat gtcttccaat gtgagatttt gggccatttt ttatagcaaa  11400
gattgaataa ggcgcatttt tcttcaa                                      11427
```

<210> SEQ ID NO 25
<211> LENGTH: 11201
<212> TYPE: DNA
<213> ORGANISM: Saccharomyces cerevisiae

<400> SEQUENCE: 25

```
aagcttcgcg gccgcgcaga atgatgaag ggtgttagcg ccgtccactg atgtgcctgg    60
tagtcatgat ttacgtataa ctaacacatc atgaggacgg cggcgtcacc ccaacgcaaa   120
agagtgactt ccctgcgctt tgccaaaacc ccatacatcg ccatctggct cctggcaggg   180
```

```
cggttgatgg acatcagccg cctcccttaa ttgctaaagc ctccacaagg cacaattaag    240
caatatttcg ggaaagtaca ccagtcagtt tgcgctttta tgactgggtt ctaaggtact    300
agatgtgaag tagtggtgac agaatcaggg agataagagg gagcagggtg gggtaatgat    360
gtgcgataac aatcttgctt ggctaatcac ccccatatct tgtagtgagt atataaatag    420
gagcctccct tcctattgca actccataaa attttttttt gtagccactt ctgtaacaag    480
ataaataaaa ccaactaatc gagatatcac atatgcggtc cggatccagt ttaaacagta    540
gctttggact tcttcgccag aggtttggtc aagtctccaa tcaaggttgt cggcttgtct    600
accttgccag aaatttacga aaagatggaa aagggtcaaa tcgttggtag atacgttgtt    660
gacacttcta aataagcgaa tttcttatga tttatgattt ttattattaa ataagttata    720
aaaaaaataa gtgtatacaa attttaaagt gactcttagg ttttaaaacg aaaattcttg    780
ttcttgagta actctttcct gtaggtcagg ttgctttctc aggtatagca tgaggtcgct    840
cttattgacc acacctctac cggcatgccg agcaaatgcc tgcaaatcgc tccccatttc    900
acccaattgt agatatgcta actccagcaa tgagttgatg aatctcggtg tgtattttat    960
gtcctcagaa gacaacacct gttgtaatcg ttcttccaca cggatcgcgg ccgcttgatc    1020
ctctacgccg gacgcatcgt ggccggcatc accggcgcca caggtgcggt tgctggcgcc    1080
tatatcgccg acatcaccga tggggaagat cgggctcgcc acttcgggct catgagcgct    1140
tgtttcggcg tgggtatggt ggcaggcccc gtggccgggg gactgttggg cgccatctcc    1200
ttgcatgcac cattccttgc ggcggcggtg ctcaacggcc tcaacctact actgggctgc    1260
ttcctaatgc aggagtcgca taaggggag cgtcgaccga tgcccttgag agccttcaac    1320
ccagtcagct ccttccggtg ggcgcgggc atgactatcg tcgccgcact tatgactgtc    1380
ttctttatca tgcaactcgt aggacaggtg ccggcagcgc tctgggtcat tttcggcgag    1440
gaccgctttc gctggagcgc gacgatgatc ggcctgtcgc ttgcggtatt cggaatcttg    1500
cacgccctcg ctcaagcctt cgtcactggt cccgccacca aacgtttcgg cgagaagcag    1560
gccattatcg ccggcatggc ggccgacgcg ctgggctacg tcttgctggc gttcgcgacg    1620
cgaggctgga tggccttccc cattatgatt cttctcgctt ccgcggcat cgggatgccc    1680 gcgttgcagg ccatgctgtc caggcaggta gatgacgacc atcagggaca gcttcaagga    1740
tcgctcgcgg ctcttaccag cctaacttcg atcactggac cgctgatcgt cacggcgatt    1800
tatgccgcct cggcgagcac atggaacggg ttggcatgga ttgtaggcgc cgccctatac    1860
cttgtctgcc tccccgcgtt gcgtcgcggt gcatggagcc gggccacctc gacctgaatg    1920
gaagccggcg gcacctcgct aacggattca ccactccaag aattggagcc aatcaattct    1980
tgcggagaac tgtgaatgcg caaaccaacc cttggcagaa catatccatc gcgtccgcca    2040
tctccagcag ccgcacgcgg cgcatctcgg gcagcgttgg gtcctggcca cggtgcgca    2100 tgatcgtgct cctgtcgttg aggacccggc taggctggcg gggttgcctt actggttagc    2160
agaatgaatc accgatacgc gagcgaacgt gaagcgactg ctgctgcaaa acgtctgcga    2220
cctgagcaac aacatgaatg gtcttcggtt tccgtgtttc gtaaagtctg gaaacgcgga    2280
agtcagcgcc ctgcaccatt atgttccgga tctgcatcgc aggatgctgc tggctaccct    2340
gtggaacacc tacatctgta ttaacgaagc gctggcattg accctgagtg attttctct    2400 ggtcccgccg catccatacc gccagttgtt taccctcaca cgttccagt aaccgggcat    2460 gttcatcatc agtaaccccgt atcgtgagca tcctctctcg tttcatcggt atcattaccc    2520
```

```
ccatgaacag aaattccccc ttacacggag gcatcaagtg accaaacagg aaaaaaccgc    2580
ccttaacatg gcccgcttta tcagaagcca gacattaacg cttctggaga aactcaacga    2640
gctggacgcg gatgaacagg cagacatctg tgaatcgctt cacgaccacg ctgatgagct    2700
ttaccgcagc tgcctcgcgc gtttcggtga tgacggtgaa aacctctgac acatgcagct    2760
cccggagacg tcacagcttg tctgtaagcg gatgccggg agcagacaag cccgtcaggg     2820
cgcgtcagcg ggtgttggcg ggtgtcgggg cgcagccatg acccagtcac gtagcgatag    2880
cggagtgtat actggcttaa ctatgcggca tcagagcaga ttgtactgag agtgcacgat    2940
atccggtgtg aaataccgca cagatgcgta aggagaaaat accgcatcag gcgctcttcc    3000
gcttcctcgc tcactgactc gctgcgctcg gtcgttcggc tgcggcgagc ggtatcagct    3060
cactcaaagg cggtaatacg gttatccaca gaatcagggg ataacgcagg aaagaacatg    3120
tgagcaaaag gccagcaaaa ggccaggaac cgtaaaaagg ccgcgttgct ggcgtttttc    3180
cataggctcc gcccccctga cgagcatcac aaaaatcgac gctcaagtca gaggtggcga    3240
aacccgacag gactataaag ataccaggcg tttccccctg gaagctccct cgtgcgctct    3300
cctgttccga ccctgccgct taccggatac ctgtccgcct ttctcccttc gggaagcgtg    3360
gcgctttctc aatgctcacg ctgtaggtat ctcagttcgg tgtaggtcgt tcgctccaag    3420
ctgggctgtg tgcacgaacc ccccgttcag cccgaccgct gcgccttatc cggtaactat    3480
cgtcttgagt ccaacccggt aagacacgac ttatcgccac tggcagcagc cactggtaac    3540
aggattagca gagcgaggta tgtaggcggt gctacagagt tcttgaagtg gtggcctaac    3600
tacggctaca ctagaaggac agtatttggt atctgcgctc tgctgaagcc agttaccttc    3660
ggaaaaagag ttggtagctc ttgatccggc aaacaaacca ccgctggtag cggtggtttt    3720
tttgtttgca agcagcagat tacgcgcaga aaaaaggat ctcaagaaga tcctttgatc      3780
ttttctacgg ggtctgacgc tcagtggaac gaaaactcac gttaagggat tttggtcatg    3840
agattatcaa aaaggatctt cacctagatc cttttaaatt aaaaatgaag ttttaaatca    3900
atctaaagta tatatgagta aacttggtct gacagttacc aatgcttaat cagtgaggca    3960
cctatctcag cgatctgtct atttcgttca tccatagttg cctgactccc cgtcgtgtag    4020
ataactacga tacgggaggg cttaccatct ggccccagtg ctgcaatgat accgcgagac    4080
ccacgctcac cggctccaga tttatcagca ataaaccagc cagccggaag ggccgagcgc    4140
agaagtggtc ctgcaacttt atccgcctcc atccagtcta ttaattgttg ccgggaagct    4200
agagtaagta gttcgccagt taatagtttg cgcaacgttg ttgccattgc tgcaggcatc    4260
gtggtgtcac gctcgtcgtt tggtatggct tcattcagct ccggttccca acgatcaagg    4320
cgagttacat gatcccccat gttgtgcaaa aaagcggtta gctccttcgg tcctccgatc    4380
gttgtcagaa gtaagttggc cgcagtgtta tcactcatgg ttatggcagc actgcataat    4440
tctcttactg tcatgccatc cgtaagatgc ttttctgtga ctggtgagta ctcaaccaag    4500
tcattctgag aatagtgtat gcggcgaccg agttgctctt gcccggcgtc aacacgggat    4560
aataccgcgc cacatagcag aactttaaaa gtgctcatca ttggaaaacg ttcttcgggg    4620
cgaaaactct caaggatctt accgctgttg agatccagtt cgatgtaacc cactcgtgca    4680
cccaactgat cttcagcatc ttttactttc accagcgttt ctgggtgagc aaaaacagga    4740
aggcaaaatg ccgcaaaaaa gggaataagg gcgacacgga aatgttgaat actcatactc    4800
ttcctttttc aatattattg aagcatttat cagggttatt gtctcatgag cggatacata    4860
tttgaatgta tttagaaaaa taaacaaata ggggttccgc gcacatttcc ccgaaaagtg    4920
```

```
ccacctgacg tctaagaaac cattattatc atgacattaa cctataaaaa taggcgtatc    4980
acgaggccct ttcgtcttca agaattccac ggactataga ctatactagt atactccgtc    5040
tactgtacga tacacttccg ctcaggtcct tgtcctttaa cgaggcctta ccactctttt    5100
gttactctat tgatccagct cagcaaaggc agtgtgatct aagattctat cttcgcgatg    5160
tagtaaaact agctagaccg agaaagagac tagaaatgca aaaggcactt ctacaatggc    5220
tgccatcatt attatccgat gtgacgctgc agaagcagaa atacacgcgg tcagtgaagc    5280
tattccgcta ttgaataacc tcagtcacct tgtgcaagaa cttaacaaga aaccaattat    5340
taaaggctta cttactgata gtagatcaac gatcagtata attaagtcta caaatgaaga    5400
gaaatttaga aacagatttt ttggcacaaa ggcaatgaga cttagagatg aagtatcagg    5460
taataattta tacgtatact acatcgagac caagaagaac attgctgatg tgatgacaaa    5520
acctcttccg ataaaaacat ttaaactatt aactaacaaa tggattcatt agatctatta    5580
cattatgggt ggtatgttgg aataaaaatc aactatcatc tactaactag tatttacgtt    5640
actagtatat tatcatatac ggtgttagaa gatgacgcaa atgatgagaa atagtcatct    5700
aaattagtgg aagctgaaac gcaaggattg ataatgtaat aggatcaatg aatattaaca    5760
tataaaatga tgataataat atttatagaa ttgtgtagaa ttgcagattc ccttttatgg    5820
attcctaaat cctcgaggag aacttctagt atatctacat acctaatatt attgccttat    5880
taaaaatgga atcccaacaa ttacatcaaa atccacattc tcttcaaaat caattgtcct    5940
gtacttcctt gttcatgtgt gttcaaaaac gttatattta taggataatt atactctatt    6000
tctcaacaag taattggttg tttggccgag cggtctaagg cgcctgattc aagaaatatc    6060
ttgaccgcag ttaactgtgg gaatactcag gtatcgtaag atgcaagagt tcgaatctct    6120
tagcaaccat tatttttttc ctcaacataa cgagaacaca caggggcgct atcgcacaga    6180
atcaaattcg atgactggaa atttttttgtt aatttcagag gtcgcctgac gcatatacct    6240
ttttcaactg aaaaattggg agaaaaagga aggtgagag ccgcggaacc ggcttttcat    6300
atagaataga gaagcgttca tgactaaatg cttgcatcac aatacttgaa gttgacaata    6360
ttatttaagg acctattgtt ttttccaata ggtggttagc aatcgtctta ctttctaact    6420
tttcttacct tttacatttc agcaatatat atatatatat ttcaaggata taccattcta    6480
atgtctgccc ctaagaagat cgtcgttttg ccaggtgacc acgttggtca agaaatcaca    6540
gccgaagcca ttaaggttct aaagctatt tctgatgttc gttccaatgt caagttcgat    6600
ttcgaaaatc atttaattgg tggtgctgct atcgatgcta caggtgtccc acttccagat    6660
gaggcgctgg aagcctccaa gaaggttgat gccgttttgt taggtgctgt gggtggtcct    6720
aaatggggta ccggtagtgt tagacctgaa caaggtttac taaaaatccg taaagaactt    6780
caattgtacg ccaacttaag accatgtaac tttgcatccg actctctttt agacttatct    6840
ccaatcaagc cacaatttgc taaaggtact gacttcgttg ttgtcagaga attagtggga    6900
ggtatttact ttggtaagag aaaggaagac gatggtgatg tgtcgcttg ggatagtgaa    6960 caatacaccg ttccagaagt gcaaagaatc acaagaatgg ccgctttcat ggccctacaa    7020
catgagccac cattgcctat ttggtccttg ataaagcta atgttttggc ctcttcaaga    7080
ttatggagaa aaactgtgga ggaaaccatc aagaacgaat tccctacatt gaaggttcaa    7140
catcaattga ttgattctgc cgccatgatc ctagttaaga acccaaccca cctaaatggt    7200
attataatca ccagcaacat gtttggtgat atcatctccg atgaagcctc cgttatccca    7260
```

-continued

```
ggttccttgg gtttgttgcc atctgcgtcc ttggcctctt tgccagacaa gaacaccgca    7320
tttggtttgt acgaaccatg ccacggttct gctccagatt tgccaaagaa taaggtcaac    7380
cctatcgcca ctatcttgtc tgctgcaatg atgttgaaat tgtcattgaa cttgcctgaa    7440
gaaggtaagg ccattgaaga tgcagttaaa aaggttttgg atgcaggtat cagaactggt    7500
gatttaggtg gttccaacag taccacggaa gtcggtgatg ctgtcgccga agaagttaag    7560
aaaatccttg cttaaaaaga ttctctttttt ttatgatatt tgtacataaa ctttataaat    7620
gaaattcata atagaaacga cacgaaatta caaaatggaa tatgttcata gggtagacga    7680
aactatatac gcaatctaca tacatttatc aagaaggaga aaaaggagga tgtaaaggaa    7740
tacaggtaag caaattgata ctaatggctc aacgtgataa ggaaaaagaa ttgcacttta    7800
acattaatat tgacaaggag gagggcacca cacaaaaagt taggtgtaac agaaaatcat    7860
gaaactatga ttcctaattt atatattgga ggattttctc taaaaaaaaa aaaatacaac    7920
aaataaaaaa cactcaatga cctgaccatt tgatggagtt taagtcaata ccttcttgaa    7980
ccatttccca taatggtgaa agttccctca agaattttac tctgtcagaa acggccttaa    8040
cgacgtagtc gacctcctct tcagtactaa atctaccaat accaaatctg atggaagaat    8100
gggctaatgc atcatcctta cccagcgcat gtaaaacata agaaggttct agggaagcag    8160
atgtacaggc tgaacccgag gataatgcga tatcccttag tgccatcaat aaagattctc    8220
cttccacgta ggcgaaagaa acgttaacac accctggata acgatgatct ggagatccgt    8280
tcaacgtggt atgttcagcg gataatagac ctttgactaa tttatcggat agtcttttga    8340
tgtgagcttg gtcgttgtca aattcttttct tcatcaatct cgcagcttca ccaaatcccg    8400
ctaccaatgg gggggccaaa gtaccagatc tcaatcctct ctcttggcca ccaccggata    8460
gtaaaggttc taatctaact cttggtctcc ttcttacata gatggcacct attccctttg    8520
gaccgtaaat cttgtgagaa gaaattgata gtaaatcaat gttcatttca ttgacatcaa    8580
tgtgaatctt accataggct tgtgcggcgt cagtatgaaa gtagatctta ttctttctac    8640
aaattgcacc aatttctttta ataggttgaa tgacaccgat ttcattattg acagccatca    8700
cagagacgag acaggtatct ggtctaatgg catcttccaa ttccttcaaa tcgataagac    8760
cttgatcgtc cacatttagg aaagtgactt caaatccctc cttcatcatg gcccgtgcgg    8820
cttccaagac acacttgtgt tccgttctag tggtgatgat gtgtttctta gtcttcttat    8880
aaaatcttgg gacacccctta agaaccatat tattagattc ggtcgctccc gaagtgaata    8940
ttatttcctt ggggtcggca ttgatcatct ttgctacgta agctctagca ttttccacag    9000
cagtatttgt ttcccaaccg taagagtgag tgttggaatg aggattacca taaagtcccg    9060
tataaaactt caacatcgta tccaaaaccc tagggtctgt tggtgtagtg gcttgcatgt    9120
caagatatat gggacgagta ccaaaacctg tgttttcttg ataagcatgg ctcattgcag    9180
tgctaccaga agctactaca gcatctgggg tggtaccgga tgcactcgca cgggcactag    9240
cctgtgcctt tgcagcagcc tgaatatcgg tatgcgtttc cagagagaag ttgtcgtcta    9300
acttcacgcc tgctgcagtc tcaatgatat tcgaatacgc tttgaggaga tacagcctaa    9360
tatccgacaa actgttttac agatttacga tcgtacttgt tacccatcat tgaattttga    9420
acatccgaac ctgggagttt tccctgaaac agatagtata tttgaacctg tataataata    9480
tatagtctag cgcttacgg aagacaatgt atgtatttcg gttcctggag aaactattgc    9540
atctattgca taggtaatct tgcacgtcgc atccccggtt cattttctgc gtttccatct    9600
tgcacttcaa tagcatatct ttgttaacga agcatctgtg cttcattttg tagaacaaaa    9660
```

-continued

```
atgcaacgcg agagcgctaa tttttcaaac aaagaatctg agctgcattt ttacagaaca      9720
gaaatgcaac gcgaaagcgc tattttacca acgaagaatc tgtgcttcat ttttgtaaaa      9780
caaaaatgca acgcgagagc gctaattttt caaacaaaga atctgagctg cattttaca       9840 gaacagaaat gcaacgcgag agcgctattt taccaacaaa gaatctatac ttcttttttg      9900
ttctacaaaa atgcatcccg agagcgctat ttttctaaca aagcatctta gattacttt      9960 tttctccttt gtgcgctcta taatgcagtc tcttgataac tttttgcact gtaggtccgt     10020
taaggttaga agaaggctac tttggtgtct atttttctctt ccataaaaaa agcctgactc    10080
cacttcccgc gtttactgat tactagcgaa gctgcgggtg cattttttca agataaaggc     10140
atccccgatt atattctata ccgatgtgga ttgcgcatac tttgtgaaca gaaagtgata     10200
gcgttgatga ttcttcattg gtcagaaaat tatgaacggt ttcttctatt ttgtctctat     10260
atactacgta taggaaatgt ttacattttc gtattgtttt cgattcactc tatgaatagt     10320
tcttactaca atttttttgt ctaaagagta atactagaga taaacataaa aaatgtagag     10380
gtcgagttta gatgcaagtt caaggagcga aggtggatg ggtaggttat atagggatat      10440
agcacagaga tatatagcaa agagatactt ttgagcaatg tttgtggaag cggtattcgc     10500
aatattttag tagctcgtta cagtccggtg cgttttttggt tttttgaaag tgcgtcttca    10560
gagcgctttt ggttttcaaa agcgctctga agttcctata ctttctagag aataggaact    10620
tcggaatagg aacttcaaag cgtttccgaa acgagcgct tccgaaaatg caacgcgagc     10680
tgcgcacata cagctcactg ttcacgtcgc acctatatct gcgtgttgcc tgtatatata    10740
tatacatgag aagaacggca tagtgcgtgt ttatgcttaa atgcgtactt atatgcgtct    10800
atttatgtag gatgaaaggt agtctagtac ctcctgtgat attatcccat tccatgcggg    10860
gtatcgtatg cttccttcag cactaccctt tagctgttct atatgctgcc actcctcaat    10920
tggattagtc tcatccttca atgctatcat ttcctttgat attcgatcct aggcatagta    10980
ccgagaaact agtgcgaagt agtgatcagg tattgctgtt atctgatgag tatacgttgt    11040
cctggccacg gcagaagcac gcttatcgct ccaatttccc acaacattag tcaactccgt    11100
taggcccttc attgaaagaa atgaggtcat caaatgtctt ccaatgtgag attttgggcc    11160
attttttata gcaaagattg aataaggcgc attttctc a                         11201
```

<210> SEQ ID NO 26
<211> LENGTH: 11204
<212> TYPE: DNA
<213> ORGANISM: Saccharomyces cerevisiae

<400> SEQUENCE: 26

```
aagcttcgcg gccgcggagg tctgcttcac gagcgcggtg tgcgcctagt attgccccga       60
cggtccgggt gcctatccct agatttcgtc gtgccccgac ccaaatagtt aaacgtgtgg     120
tttatgggtg caccagggct ttatcgtgtt ttatatcgat ggcgatttgt gcctccagtg     180 tattttttgta tatccaatta aggtttctta cctaattta tttttatcat ctttagttaa   240
tgctggtttg ctctgtttct gctgctttct gtgcggttct cctcttctct gtttcttcg     300 tgttgtcccc catcgccgat gggcttatat ggcgtatata tatagagcga ttttacgt       360 cgaagatcat ctcagtttgc ttgatagcct ttctacttta ttactttcgt ttttaacctc     420
attatacttt agttttcttt gatcggtttt tttctctgta tacttaaaag ttcaaatcaa     480
agaaacatac aaaactacgt ttatatcaat tacatatgcg gtccggatcc agtttaaaca    540
```

-continued

| | | |
|---|---|---|
| gtagctttgg acttcttcgc cagaggtttg gtcaagtctc caatcaaggt tgtcggcttg | 600 |
| tctaccttgc cagaaattta cgaaaagatg gaaaagggtc aaatcgttgg tagatacgtt | 660 |
| gttgacactt ctaaataagc gaatttctta tgatttatga tttttattat taaataagtt | 720 |
| ataaaaaaaa taagtgtata caaattttaa agtgactctt aggttttaaa acgaaaattc | 780 |
| ttgttcttga gtaactcttt cctgtaggtc aggttgcttt ctcaggtata gcatgaggtc | 840 |
| gctcttattg accacacctc taccggcatg ccagcaaat gcctgcaaat cgctccccat | 900 |
| ttcacccaat tgtagatatg ctaactccag caatgagttg atgaatctcg gtgtgtattt | 960 |
| tatgtcctca gaagacaaca cctgttgtaa tcgttcttcc acacggatcg cggccgcttg | 1020 |
| atcctctacg ccggacgcat cgtggccggc atcaccggcg ccacaggtgc ggttgctggc | 1080 |
| gcctatatcg ccgacatcac cgatggggaa gatcgggctc gccacttcgg gctcatgagc | 1140 |
| gcttgtttcg cgtgggtat ggtggcaggc ccgtggccg ggggactgtt gggcgccatc | 1200 |
| tccttgcatg caccattcct tgcggcggcg gtgctcaacg gcctcaacct actactgggc | 1260 |
| tgcttcctaa tgcaggagtc gcataaggga gagcgtcgac cgatgccctt gagagccttc | 1320 |
| aacccagtca gctccttccg gtgggcgcgg ggcatgacta tcgtcgccgc acttatgact | 1380 |
| gtcttcttta tcatgcaact cgtaggacag gtgccggcag cgctctgggt cattttcggc | 1440 |
| gaggaccgct ttcgctggag cgcgacgatg atcggcctgt cgcttgcggt attcggaatc | 1500 |
| ttgcacgccc tcgctcaagc cttcgtcact ggtcccgcca ccaaacgttt cggcgagaag | 1560 |
| caggccatta tcgccggcat ggcggccgac gcgctgggct acgtcttgct ggcgttcgcg | 1620 |
| acgcgaggct ggatggcctt ccccattatg attcttctcg cttccggcgg catcgggatg | 1680 |
| cccgcgttgc aggccatgct gtccaggcag gtagatgacg accatcaggg acagcttcaa | 1740 |
| ggatcgctcg cggctcttac cagcctaact tcgatcactg gaccgctgat cgtcacggcg | 1800 |
| atttatgccg cctcggcgag cacatggaac gggttggcat ggattgtagg cgccgccta | 1860 |
| taccttgtct gcctccccgc gttgcgtcgc ggtgcatgga gccgggccac ctcgacctga | 1920 |
| atggaagccg gcggcacctc gctaacggat tcaccactcc aagaattgga gccaatcaat | 1980 |
| tcttgcggag aactgtgaat gcgcaaacca acccttggca gaacatatcc atcgcgtccg | 2040 |
| ccatctccag cagccgcacg cggcgcatct cgggcagcgt tgggtcctgg ccacgggtgc | 2100 |
| gcatgatcgt gctcctgtcg ttgaggaccc ggctaggctg gcggggttgc cttactggtt | 2160 |
| agcagaatga atcaccgata cgcgagcgaa cgtgaagcga ctgctgctgc aaaacgtctg | 2220 |
| cgacctgagc aacaacatga atggtcttcg gtttccgtgt ttcgtaaagt ctggaaacgc | 2280 |
| ggaagtcagc gccctgcacc attatgttcc ggatctgcat cgcaggatgc tgctggctac | 2340 |
| cctgtggaac acctacatct gtattaacga agcgctggca ttgaccctga gtgatttttc | 2400 |
| tctggtcccg ccgcatccat accgccagtt gtttaccctc acaacgttcc agtaaccggg | 2460 |
| catgttcatc atcagtaacc cgtatcgtga gcatcctctc tcgtttcatc ggtatcatta | 2520 |
| cccccatgaa cagaaattcc cccttacacg gaggcatcaa gtgaccaaac aggaaaaaac | 2580 |
| cgcccttaac atgcccgct ttatcagaag ccagacatta acgcttctgg agaaactcaa | 2640 |
| cgagctggac gcggatgaac aggcagacat ctgtgaatcg cttcacgacc acgctgatga | 2700 |
| gctttaccgc agctgcctcg cgcgtttcgg tgatgacggt gaaaacctct gacacatgca | 2760 |
| gctcccggag acgtcacag cttgtctgta agcggatgcc gggagcagac aagcccgtca | 2820 |
| gggcgcgtca gcgggtgttg gcgggtgtcg ggcgcagcc atgacccagt cacgtagcga | 2880 |
| tagcggagtg tatactggct taactatgcg gcatcagagc agattgtact gagagtgcac | 2940 |

-continued

```
gatatccggt gtgaaatacc gcacagatgc gtaaggagaa ataccgcat caggcgctct    3000
tccgcttcct cgctcactga ctcgctgcgc tcggtcgttc ggctgcggcg agcggtatca    3060
gctcactcaa aggcggtaat acggttatcc acagaatcag gggataacgc aggaaagaac    3120
atgtgagcaa aaggccagca aaaggccagg aaccgtaaaa aggccgcgtt gctggcgttt    3180
ttccataggc tccgcccccc tgacgagcat cacaaaaatc gacgctcaag tcagaggtgg    3240
cgaaacccga caggactata aagataccag gcgtttcccc ctggaagctc cctcgtgcgc    3300
tctcctgttc cgaccctgcc gcttaccgga tacctgtccg cctttctccc ttcgggaagc    3360
gtggcgcttt ctcaatgctc acgctgtagg tatctcagtt cggtgtaggt cgttcgctcc    3420
aagctgggct gtgtgcacga acccccgtt cagcccgacc gctgcgcctt atccggtaac    3480
tatcgtcttg agtccaaccc ggtaagacac gacttatcgc cactggcagc agccactggt    3540
aacaggatta gcagagcgag gtatgtaggc ggtgctacag agttcttgaa gtggtggcct    3600
aactacggct acactagaag gacagtattt ggtatctgcg ctctgctgaa gccagttacc    3660
ttcggaaaaa gagttggtag ctcttgatcc ggcaaacaaa ccaccgctgg tagcggtggt    3720
ttttttgttt gcaagcagca gattacgcgc agaaaaaaag gatctcaaga agatcctttg    3780
atcttttcta cggggtctga cgctcagtgg aacgaaaact cacgttaagg gattttggtc    3840
atgagattat caaaaaggat cttcacctag atcctttta attaaaaatg aagttttaaa    3900
tcaatctaaa gtatatatga gtaaacttgg tctgacagtt accaatgctt aatcagtgag    3960
gcacctatct cagcgatctg tctatttcgt tcatccatag ttgcctgact ccccgtcgtg    4020
tagataacta cgatacggga gggcttacca tctggcccca gtgctgcaat gataccgcga    4080
gacccacgct caccggctcc agatttatca gcaataaacc agccagccgg aagggccgag    4140
cgcagaagtg gtcctgcaac tttatccgcc tccatccagt ctattaattg ttgccgggaa    4200
gctagagtaa gtagttcgcc agttaatagt ttgcgcaacg ttgttgccat tgctgcaggc    4260
atcgtggtgt cacgctcgtc gtttggtatg gcttcattca gctccggttc caacgatca    4320
aggcgagtta catgatcccc catgttgtgc aaaaaagcgg ttagctcctt cggtcctccg    4380
atcgttgtca gaagtaagtt ggccgcagtg ttatcactca tggttatggc agcactgcat    4440
aattctctta ctgtcatgcc atccgtaaga tgcttttctg tgactggtga gtactcaacc    4500
aagtcattct gagaatagtg tatgcggcga ccgagttgct cttgcccggc gtcaacacgg    4560
gataataccg cgccacatag cagaacttta aaagtgctca tcattggaaa acgttcttcg    4620
gggcgaaaac tctcaaggat cttaccgctg ttgagatcca gttcgatgta acccactcgt    4680
gcacccaact gatcttcagc atcttttact ttcaccagcg tttctgggtg agcaaaaaca    4740
ggaaggcaaa atgccgcaaa aaagggaata agggcgacac ggaaatgttg aatactcata    4800
ctcttccttt ttcaatatta ttgaagcatt tatcagggtt attgtctcat gagcggatac    4860
atatttgaat gtatttagaa aaataaacaa ataggggttc cgcgcacatt tccccgaaaa    4920
gtgccacctg acgtctaaga aaccattatt atcatgacat taacctataa aaataggcgt    4980
atcacgaggc cctttcgtct tcaagaattc cacggactat agactatact agtatactcc    5040
gtctactgta cgatacactt ccgctcaggt ccttgtcctt taacgaggcc ttaccactct    5100
tttgttactc tattgatcca gctcagcaaa ggcagtgtga tctaagattc tatcttcgcg    5160
atgtagtaaa actagctaga ccgagaaaga gactagaaat gcaaaaggca cttctacaat    5220
ggctgccatc attattatcc gatgtgacgc tgcagaagca gaaatacacg cggtcagtga    5280
```

```
agctattccg ctattgaata acctcagtca ccttgtgcaa gaacttaaca agaaaccaat      5340
tattaaaggc ttacttactg atagtagatc aacgatcagt ataattaagt ctacaaatga      5400
agagaaattt agaaacagat tttttggcac aaaggcaatg agacttagag atgaagtatc      5460
aggtaataat ttatacgtat actacatcga gaccaagaag aacattgctg atgtgatgac      5520
aaaacctctt ccgataaaaa catttaaact attaactaac aaatggattc attagatcta      5580
ttacattatg ggtggtatgt tggaataaaa atcaactatc atctactaac tagtatttac      5640
gttactagta tattatcata tacggtgtta aagatgacg caaatgatga gaaatagtca      5700
tctaaattag tggaagctga aacgcaagga ttgataatgt aataggatca atgaatatta      5760
acatataaaa tgatgataat aatatttata gaattgtgta gaattgcaga ttcccttta      5820 tggattccta aatcctcgag gagaacttct agtatatcta catacctaat attattgcct      5880
tattaaaaat ggaatcccaa caattacatc aaaatccaca ttctcttcaa aatcaattgt      5940
cctgtacttc cttgttcatg tgtgttcaaa aacgttatat ttataggata attatactct      6000
atttctcaac aagtaattgg ttgtttggcc gagcggtcta aggcgcctga ttcaagaaat      6060
atcttgaccg cagttaactg tgggaatact caggtatcgt aagatgcaag agttcgaatc      6120
tcttagcaac cattattttt ttcctcaaca taacgagaac acacaggggc gctatcgcac      6180
agaatcaaat tcgatgactg gaatttttt gttaatttca gaggtcgcct gacgcatata      6240
cctttttcaa ctgaaaaatt gggagaaaaa ggaaaggtga gagccgcgga accggctttt      6300
catatagaat agagaagcgt tcatgactaa atgcttgcat cacaatactt gaagttgaca      6360
atattattta aggacctatt gttttttcca ataggtggtt agcaatcgtc ttactttcta      6420
acttttctta ccttttacat ttcagcaata tatatatata tatttcaagg atataccatt      6480
ctaatgtctg cccctaagaa gatcgtcgtt ttgccaggtg accacgttgg tcaagaaatc      6540
acagccgaag ccattaaggt tcttaaagct atttctgatg ttcgttccaa tgtcaagttc      6600
gatttcgaaa atcatttaat tggtggtgct gctatcgatg ctacaggtgt cccacttcca      6660
gatgaggcgc tggaagcctc caagaaggtt gatgccgttt tgttaggtgc tgtgggtggt      6720
cctaaatggg gtaccggtag tgttagacct gaacaaggtt tactaaaaat ccgtaaagaa      6780
cttcaattgt acgccaactt aagaccatgt aactttgcat ccgactctct tttagactta      6840
tctccaatca agccacaatt tgctaaaggt actgacttcg ttgttgtcag agaattagtg      6900
ggaggtattt actttggtaa gagaaaggaa gacgatggtg atggtgtcgc ttgggatagt      6960
gaacaataca ccgttccaga agtgcaaaga atcacaagaa tggccgcttt catggcccta      7020
caacatgagc caccattgcc tatttggtcc ttggataaag ctaatgtttt ggcctcttca      7080
agattatgga gaaaaactgt ggaggaaacc atcaagaacg aattccctac attgaaggtt      7140
caacatcaat tgattgattc tgccgccatg atcctagtta agaacccaac ccacctaaat      7200
ggtattataa tcaccagcaa catgtttggt gatatcatct ccgatgaagc ctccgttatc      7260
ccaggttcct tgggttttgt tgccatctgc gtccttggcc ttttgccaga caagaacacc      7320
gcatttggtt tgtacgaacc atgccacggt tctgctccag atttgccaaa gaataaggtc      7380
aaccctatcg ccactatctt gtctgctgca atgatgttga aattgtcatt gaacttgcct      7440
gaagaaggta aggccattga agatgcagtt aaaaaggttt tggatgcagg tatcagaact      7500
ggtgatttag gtggttccaa cagtaccacg gaagtcggtg atgctgtcgc cgaagaagtt      7560
aagaaaatcc ttgcttaaaa agattctctt tttttatgat atttgtacat aaactttata      7620
aatgaaattc ataatagaaa cgacacgaaa ttacaaaatg gaatatgttc ataggggtaga      7680
```

```
cgaaactata tacgcaatct acatacattt atcaagaagg agaaaaagga ggatgtaaag   7740
gaatacaggt aagcaaattg atactaatgg ctcaacgtga taaggaaaaa gaattgcact   7800
ttaacattaa tattgacaag gaggagggca ccacacaaaa agttaggtgt aacagaaaat   7860
catgaaacta tgattcctaa tttatatatt ggaggatttt ctctaaaaaa aaaaaaatac   7920
aacaaataaa aaacactcaa tgacctgacc atttgatgga gtttaagtca ataccttctt   7980
gaaccatttc ccataatggt gaaagttccc tcaagaattt tactctgtca gaacggcct    8040 taacgacgta gtcgacctcc tcttcagtac taaatctacc aataccaaat ctgatggaag   8100
aatgggctaa tgcatcatcc ttacccagcg catgtaaaac ataagaaggt tctagggaag   8160
cagatgtaca ggctgaaccc gaggataatg cgatatccct tagtgccatc aataaagatt   8220
ctccttccac gtaggcgaaa gaaacgttaa cacaccctgg ataacgatga tctggagatc   8280
cgttcaacgt ggtatgttca gcggataata gacctttgac taatttatcg gatagtcttt   8340
tgatgtgagc ttggtcgttg tcaaattctt tcttcatcaa tctcgcagct tcaccaaatc   8400
ccgctaccaa tgggggggcc aaagtaccag atctcaatcc tctctcttgg ccaccaccgg   8460
atagtaaagg ttctaatcta actcttggtc tccttcttac atagatggca cctattccct   8520
ttggaccgta atcttgtga gaagaaattg atagtaaatc aatgttcatt tcattgacat    8580
caatgtgaat cttaccatag gcttgtgcgg cgtcagtatg aaagtagatc ttattctttc   8640
tacaaattgc accaatttct ttaataggtt gaatgacacc gatttcatta ttgacagcca   8700
tcacagagac gagacaggta tctggtctaa tggcatcttc caattccttc aaatcgataa   8760
gaccttgatc gtccacattt aggaaagtga cttcaaatcc ctccttcatc atggcccgtg   8820
cggcttccaa gacacacttg tgttccgttc tagtggtgat gatgtgtttc ttagtcttct   8880
tataaaatct tgggacaccc ttaagaacca tattattaga ttcggtcgct cccgaagtga   8940
atattatttc cttggggtcg gcattgatca tctttgctac gtaagctcta gcattttcca   9000
cagcagtatt tgtttcccaa ccgtaagagt gagtgttgga atgaggatta ccataaagtc   9060
ccgtataaaa cttcaacatc gtatccaaaa ccctagggtc tgttggtgta gtggcttgca   9120
tgtcaagata tatgggacga gtaccaaaac ctgtgttttc ttgataagca tggctcattg   9180
cagtgctacc agaagctact acagcatctg gggtggtacc ggatgcactc gcacgggcac   9240
tagcctgtgc ctttgcagca gcctgaatat cggtatgcgt ttccagagag aagttgtcgt   9300
ctaacttcac gcctgctgca gtctcaatga tattcgaata cgctttgagg agatacagcc   9360
taatatccga caaactgttt tacagattta cgatcgtact tgttacccat cattgaatt    9420 tgaacatccg aacctgggag ttttccctga aacagatagt atatttgaac ctgtataata   9480
atatatagtc tagcgcttta cggaagacaa tgtatgtatt tcggttcctg gagaaactat   9540
tgcatctatt gcataggtaa tcttgcacgt cgcatcccg gttcatttt tgcgtttcca     9600 tcttgcactt caatagcata tctttgttaa cgaagcatct gtgcttcatt ttgtagaaca   9660
aaaatgcaac gcgagagcgc taattttttca aacaaagaat ctgagctgca tttttacaga  9720
acagaaatgc aacgcgaaag cgctatttta ccaacgaaga atctgtgctt catttttgta   9780
aaacaaaaat gcaacgcgag agcgctaatt tttcaaacaa agaatctgag ctgcatttttt  9840 acagaacaga atgcaacgc gagagcgcta ttttaccaac aaagaatcta tacttctttt   9900
ttgttctaca aaaatgcatc ccgagagcgc tatttttcta acaaagcatc ttagattact   9960
ttttttctcc tttgtgcgct ctataatgca gtctcttgat aacttttttgc actgtaggtc   10020
```

```
cgttaaggtt agaagaaggc tactttggtg tctattttct cttccataaa aaaagcctga    10080
ctccacttcc cgcgtttact gattactagc gaagctgcgg gtgcattttt tcaagataaa    10140
ggcatccccg attatattct ataccgatgt ggattgcgca ctttgtga acagaaagtg    10200 atagcgttga tgattcttca ttggtcagaa aattatgaac ggtttcttct attttgtctc    10260
tatatactac gtataggaaa tgtttacatt ttcgtattgt tttcgattca ctctatgaat    10320
agttcttact acaattttt tgtctaaaga gtaatactag agataaacat aaaaaatgta    10380
gaggtcgagt ttagatgcaa gttcaaggag cgaaaggtgg atgggtaggt tatataggga    10440
tatagcacag agatatatag caaagagata cttttgagca atgtttgtgg aagcggtatt    10500
cgcaatattt tagtagctcg ttacagtccg gtgcgttttt ggtttttga aagtgcgtct    10560 tcagagcgct tttggttttc aaaagcgctc tgaagttcct atactttcta gagaatagga    10620
acttcggaat aggaacttca aagcgtttcc gaaaacgagc gcttccgaaa atgcaacgcg    10680
agctgcgcac atacagctca ctgttcacgt cgcacctata tctgcgtgtt gcctgtatat    10740
atatatacat gagaagaacg gcatagtgcg tgtttatgct taaatgcgta cttatatgcg    10800
tctatttatg taggatgaaa ggtagtctag tacctcctgt gatattatcc cattccatgc    10860
ggggtatcgt atgcttcctt cagcactacc ctttagctgt tctatatgct gccactcctc    10920
aattggatta gtctcatcct tcaatgctat catttccttt gatattcgat cctaggcata    10980
gtaccgagaa actagtgcga agtagtgatc aggtattgct gttatctgat gagtatacgt    11040
tgtcctggcc acggcagaag cacgcttatc gctccaattt cccacaacat tagtcaactc    11100
cgttaggccc ttcattgaaa gaatgaggt catcaaatgt cttccaatgt gagattttgg    11160
gccatttttt atagcaaaga ttgaataagg cgcattttc ttca                     11204

<210> SEQ ID NO 27
<211> LENGTH: 12008
<212> TYPE: DNA
<213> ORGANISM: Saccharomyces cerevisiae

<400> SEQUENCE: 27
gaattctcat gtttgacagc ttatcatcga taagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct     240
atatgcgttg atgcaatttc tatgcgcacc cgttctcgga gcactgtccg accgctttgg     300
ccgccgccca gtcctgctcg cttcgctact tggagccact atcgactacg cgatcatggc     360
gaccacaccc gtcctgtgga tcaagcggcc gcagtacgta atgcggtatc gtgaaagcga     420 aaaaaaact aacagtagat aagacagata gacagataga gatggacgag aaacaggggg     480
ggagaaaagg ggaaaagaga aggaaagaaa gactcatcta tcgcagataa gacaatcaac     540
cctcatggcg cctccaacca ccatccgcac tagggaccaa gcgctcgcac cgttagcaac     600
gcttgactca caaccaact gccggctgaa agagcttgtg caatgggagt gccaattcaa     660
aggagccgaa tacgtctgct cgccttttaa gaggcttttt gaacactgca ttgcacccga     720
caaatcagcc actaactacg aggtcacgga cacatatacc aatagttaaa aattacatat     780
actctatata gcacagtagt gtgataaata aaaaattttg ccaagacttt tttaaactgc     840
acccgacaga tcaggtctgt gcctactatg cacttatgcc cggggtcccg ggaggagaaa     900
```

-continued

| | | |
|---|---|---|
| aaacgagggc tgggaaatgt ccgtggactt taaacgctcc gggttagcag agtagcaggg | 960 |
| ctttcggctt tggaaattta ggtgacttgt tgaaaaagca aatttgggc tcagtaatgc | 1020 |
| cactgcagtg gcttatcacg ccaggactgc gggagtggcg ggggcaaaca cacccgcgat | 1080 |
| aaagagcgcg atgaatataa aaggggggcca atgttacgtc ccgttatatt ggagttcttc | 1140 |
| ccatacaaac ttaagagtcc aattagcttc atcgccaata aaaaaacaag ctaaacctaa | 1200 |
| ttctaacaag cacatatgcg gtccggatcc agtttaaaca gtagctttgg acttcttcgc | 1260 |
| cagaggtttg gtcaagtctc caatcaaggt tgtcggcttg tctaccttgc cagaaattta | 1320 |
| cgaaaagatg gaaaagggtc aaatcgttgg tagatacgtt gttgacactt ctaaataagc | 1380 |
| gaatttctta tgatttatga tttttattat taaataagtt ataaaaaaaa taagtgtata | 1440 |
| caaatttaa agtgactctt aggttttaaa acgaaaattc ttgttcttga gtaactcttt | 1500 |
| cctgtaggtc aggttgcttt ctcaggtata gcatgaggtc gctcttattg accacacctc | 1560 |
| taccggcatg ccgagcaaat gcctgcaaat cgctccccat ttcacccaat tgtagatatg | 1620 |
| ctaactccag caatgagttg atgaatctcg gtgtgtattt tatgtcctca gaagacaaca | 1680 |
| cctgttgtaa tcgttcttcc acacggatcg cggccgcttg atcctctacg ccggacgcat | 1740 |
| cgtggccggc atcaccggcg ccacaggtgc ggttgctggc gcctatatcg ccgacatcac | 1800 |
| cgatggggaa gatcgggctc gccacttcgg gctcatgagc gcttgtttcg gcgtgggtat | 1860 |
| ggtggcaggc cccgtggccg ggggactgtt gggcgccatc tccttgcatg caccattcct | 1920 |
| tgcggcggcg gtgctcaacg gcctcaacct actactgggc tgcttcctaa tgcaggagtc | 1980 |
| gcataaggga gagcgtcgac cgatgccctt gagagccttc aacccagtca gctccttccg | 2040 |
| gtgggcgcgg ggcatgacta tcgtcgccgc acttatgact gtcttcttta tcatgcaact | 2100 |
| cgtaggacag gtgccggcag cgctctgggt cattttcggc gaggaccgct ttcgctggag | 2160 |
| cgcgacgatg atcggcctgt cgcttgcggt attcggaatc ttgcacgccc tcgctcaagc | 2220 |
| cttcgtcact ggtcccgcca ccaaacgttt cggcgagaag caggccatta tcgccggcat | 2280 |
| ggcggccgac gcgctgggct acgtcttgct ggcgttcgcg acgcgaggct ggatggcctt | 2340 |
| ccccattatg attcttctcg cttccggcgg catcgggatg cccgcgttgc aggccatgct | 2400 |
| gtccaggcag gtagatgacg accatcaggg acagcttcaa ggatcgctcg cggctcttac | 2460 |
| cagcctaact tcgatcactg gaccgctgat cgtcacggcg atttatgccg cctcggcgag | 2520 |
| cacatggaac gggttggcat ggattgtagg cgccgcccta taccttgtct gcctccccgc | 2580 |
| gttgcgtcgc ggtgcatgga gccgggccac ctcgacctga atggaagccg gcggcacctc | 2640 |
| gctaacggat tcaccactcc aagaattgga gccaatcaat tcttgcggag aactgtgaat | 2700 |
| gcgcaaacca cccttggca gaacatatcc atcgcgtccg ccatctccag cagccgcacg | 2760 |
| cggcgcatct cggcagcgt tgggtcctgg ccacgggtgc gcatgatcgt gctcctgtcg | 2820 |
| ttgaggaccc ggctaggctg gcggggttgc cttactggtt agcagaatga atcaccgata | 2880 |
| cgcgagcgaa cgtgaagcga ctgctgctgc aaaacgtctg cgacctgagc aacaacatga | 2940 |
| atggtcttcg gtttccgtgt ttcgtaaagt ctggaaacgc ggaagtcagc gccctgcacc | 3000 |
| attatgttcc ggatctgcat cgcaggatgc tgctggctac cctgtggaac acctacatct | 3060 |
| gtattaacga agcgctggca ttgaccctga gtgatttttc tctggtcccg ccgcatccat | 3120 |
| accgccagtt gtttaccctc acaacgttcc agtaaccggg catgttcatc atcagtaacc | 3180 |
| cgtatcgtga gcatcctctc tcgtttcatc ggtatcatta cccccatgaa cagaaattcc | 3240 |
| cccttacacg gaggcatcaa gtgaccaaac aggaaaaaac cgcccttaac atggcccgct | 3300 |

```
ttatcagaag ccagacatta acgcttctgg agaaactcaa cgagctggac gcggatgaac    3360
aggcagacat ctgtgaatcg cttcacgacc acgctgatga gctttaccgc agctgcctcg    3420
cgcgtttcgg tgatgacggt gaaaacctct gacacatgca gctcccggag acggtcacag    3480
cttgtctgta agcggatgcc gggagcagac aagcccgtca gggcgcgtca gcgggtgttg    3540
gcgggtgtcg gggcgcagcc atgacccagt cacgtagcga tagcggagtg tatactggct    3600
taactatgcg gcatcagagc agattgtact gagagtgcac gatatccggt gtgaaatacc    3660
gcacagatgc gtaaggagaa ataccgcat caggcgctct tccgcttcct cgctcactga    3720
ctcgctgcgc tcggtcgttc ggctgcggcg agcggtatca gctcactcaa aggcggtaat    3780
acggttatcc acagaatcag gggataacgc aggaaagaac atgtgagcaa aaggccagca    3840
aaaggccagg aaccgtaaaa aggccgcgtt gctggcgttt ttccataggc tccgcccccc    3900
tgacgagcat cacaaaaatc gacgctcaag tcagaggtgg cgaaacccga caggactata    3960
aagataccag gcgtttcccc ctggaagctc cctcgtgcgc tctcctgttc cgaccctgcc    4020
gcttaccgga tacctgtccg cctttctccc ttcgggaagc gtggcgcttt ctcaatgctc    4080
acgctgtagg tatctcagtt cggtgtaggt cgttcgctcc aagctgggct gtgtgcacga    4140
accccccgtt cagcccgacc gctgcgcctt atccggtaac tatcgtcttg agtccaaccc    4200
ggtaagacac gacttatcgc cactggcagc agccactggt aacaggatta gcagagcgag    4260
gtatgtaggc ggtgctacag agttcttgaa gtggtggcct aactacggct acactagaag    4320
gacagtattt ggtatctgcg ctctgctgaa gccagttacc ttcggaaaaa gagttggtag    4380
ctcttgatcc ggcaaacaaa ccaccgctgg tagcggtggt ttttttgttt gcaagcagca    4440
gattacgcgc agaaaaaaag gatctcaaga agatcctttg atcttttcta cggggtctga    4500
cgctcagtgg aacgaaaact cacgttaagg gattttggtc atgagattat caaaaaggat    4560
cttcacctag atccttttaa attaaaaatg aagttttaaa tcaatctaaa gtatatatga    4620
gtaaacttgg tctgacagtt accaatgctt aatcagtgag gcacctatct cagcgatctg    4680
tctatttcgt tcatccatag ttgcctgact ccccgtcgtg tagataacta cgatacggga    4740
gggcttacca tctggcccca gtgctgcaat gataccgcga gacccacgct caccggctcc    4800
agatttatca gcaataaacc agccagccgg aagggccgag cgcagaagtg gtcctgcaac    4860
tttatccgcc tccatccagt ctattaattg ttgccgggaa gctagagtaa gtagttcgcc    4920
agttaatagt ttgcgcaacg ttgttgccat tgctgcaggc atcgtggtgt cacgctcgtc    4980
gtttggtatg gcttcattca gctccggttc ccaacgatca aggcgagtta catgatcccc    5040
catgttgtgc aaaaaagcgg ttagctcctt cggtcctccg atcgttgtca gaagtaagtt    5100
ggccgcagtg ttatcactca tggttatggc agcactgcat aattctctta ctgtcatgcc    5160
atccgtaaga tgcttttctg tgactggtga gtactcaacc aagtcattct gagaatagtg    5220
tatgcggcga ccgagttgct cttgcccggc gtcaacacgg gataataccg cgccacatag    5280
cagaacttta aaagtgctca tcattggaaa acgttcttcg gggcgaaaac tctcaaggat    5340
cttaccgctg ttgagatcca gttcgatgta acccactcgt gcacccaact gatcttcagc    5400
atcttttact ttcaccagcg tttctgggtg agcaaaaaca ggaaggcaaa atgccgcaaa    5460
aaagggaata agggcgacac ggaaatgttg aatactcata ctcttccttt ttcaatatta    5520
ttgaagcatt tatcagggtt attgtctcat gagcggatac atatttgaat gtatttagaa    5580
aaataaacaa ataggggttc cgcgcacatt tccccgaaaa gtgccacctg acgtctaaga    5640
```

```
aaccattatt atcatgacat taacctataa aaataggcgt atcacgaggc cctttcgtct   5700
tcaagaattc cacggactat agactatact agtatactcc gtctactgta cgatacactt   5760
ccgctcaggt ccttgtcctt taacgaggcc ttaccactct tttgttactc tattgatcca   5820
gctcagcaaa ggcagtgtga tctaagattc tatcttcgcg atgtagtaaa actagctaga   5880
ccgagaaaga gactagaaat gcaaaaggca cttctacaat ggctgccatc attattatcc   5940
gatgtgacgc tgcagaagca gaaatacacg cggtcagtga agctattccg ctattgaata   6000
acctcagtca ccttgtgcaa gaacttaaca agaaaccaat tattaaaggc ttacttactg   6060
atagtagatc aacgatcagt ataattaagt ctacaaatga agagaaattt agaaacagat   6120
tttttggcac aaaggcaatg agacttagag atgaagtatc aggtaataat ttatacgtat   6180
actacatcga gaccaagaag aacattgctg atgtgatgac aaaacctctt ccgataaaaa   6240
catttaaact attaactaac aaatggattc attagatcta ttacattatg ggtggtatgt   6300
tggaataaaa atcaactatc atctactaac tagtatttac gttactagta tattatcata   6360
tacggtgtta agatgacg caaatgatga gaaatagtca tctaaattag tggaagctga   6420
aacgcaagga ttgataatgt aataggatca atgaatatta acatataaaa tgatgataat   6480
aatatttata gaattgtgta gaattgcaga ttcccttta tggattccta atcctcgag   6540 gagaacttct agtatatcta catacctaat attattgcct tattaaaaat ggaatcccaa   6600
caattacatc aaaatccaca ttctcttcaa aatcaattgt cctgtacttc cttgttcatg   6660
tgtgttcaaa aacgttatat ttataggata attatactct atttctcaac aagtaattgg   6720
ttgtttggcc gagcggtcta aggcgcctga ttcaagaaat atcttgaccg cagttaactg   6780
tgggaatact caggtatcgt aagatgcaag agttcgaatc tcttagcaac cattatttt   6840 ttcctcaaca taacgagaac acacaggggc gctatcgcac agaatcaaat tcgatgactg   6900
gaaatttttt gttaatttca gaggtcgcct gacgcatata cctttttcaa ctgaaaaatt   6960
gggagaaaaa ggaaaggtga gagccgcgga accggctttt catatagaat agagaagcgt   7020
tcatgactaa atgcttgcat cacaatactt gaagttgaca atattattta aggacctatt   7080
gttttttcca ataggtggtt agcaatcgtc ttactttcta acttttctta ccttttacat   7140
ttcagcaata tatatatata tatttcaagg ataccatt ctaatgtctg ccctaagaa   7200 gatcgtcgtt ttgccaggtg accacgttgg tcaagaaatc acagccgaag ccattaaggt   7260
tcttaaagct atttctgatg ttcgttccaa tgtcaagttc gatttcgaaa atcatttaat   7320
tggtggtgct gctatcgatg ctacaggtgt cccacttcca gatgaggcgc tggaagcctc   7380
caagaaggtt gatgccgttt tgttaggtgc tgtgggtggt cctaaatggg gtaccggtag   7440
tgttagacct gaacaaggtt tactaaaaat ccgtaaagaa cttcaattgt acgccaactt   7500
aagaccatgt aactttgcat ccgactctct tttagactta tctccaatca agccacaatt   7560
tgctaaaggt actgacttcg ttgttgtcag agaattagtg ggaggtattt actttggtaa   7620
gagaaaggaa gacgatggtg atggtgtcgc ttgggatagt gaacaataca ccgttccaga   7680
agtgcaaaga atcacaagaa tggccgcttt catggcccta caacatgagc caccattgcc   7740
tatttggtcc ttggataaag ctaatgtttt ggcctcttca agattatgga gaaaaactgt   7800
ggaggaaacc atcaagaacg aattccctac attgaaggtt caacatcaat tgattgattc   7860
tgccgccatg atcctagtta agaacccaac ccacctaaat ggtattataa tcaccagcaa   7920
catgtttggt gatatcatct ccgatgaagc ctccgttatc ccaggttcct gggtttgtt   7980 gccatctgcg tccttggcct ctttgccaga caagaacacc gcatttggtt tgtacgaacc   8040
```

```
atgccacggt tctgctccag atttgccaaa gaataaggtc aaccctatcg ccactatctt    8100
gtctgctgca atgatgttga aattgtcatt gaacttgcct gaagaaggta aggccattga    8160
agatgcagtt aaaaaggttt tggatgcagg tatcagaact ggtgatttag gtggttccaa    8220
cagtaccacg gaagtcggtg atgctgtcgc cgaagaagtt aagaaaatcc ttgcttaaaa    8280
agattctctt tttttatgat atttgtacat aaactttata aatgaaattc ataatagaaa    8340
cgacacgaaa ttacaaaatg gaatatgttc atagggtaga cgaaactata tacgcaatct    8400
acatacattt atcaagaagg agaaaaagga ggatgtaaag gaatacaggt aagcaaattg    8460
atactaatgg ctcaacgtga taaggaaaaa gaattgcact ttaacattaa tattgacaag    8520
gaggagggca ccacacaaaa agttaggtgt aacagaaaat catgaaacta tgattcctaa    8580
tttatatatt ggaggatttt ctctaaaaaa aaaaaatac aacaaataaa aaacactcaa     8640
tgacctgacc atttgatgga gtttaagtca ataccttctt gaaccatttc ccataatggt    8700
gaaagttccc tcaagaattt tactctgtca gaaacggcct taacgacgta gtcgacctcc    8760
tcttcagtac taaatctacc aataccaaat ctgatggaag aatgggctaa tgcatcatcc    8820
ttacccagcg catgtaaaac ataagaaggt tctagggaag cagatgtaca ggctgaaccc    8880
gaggataatg cgatatccct tagtgccatc aataaagatt ctccttccac gtaggcgaaa    8940
gaaacgttaa cacaccctgg ataacgatga tctggagatc cgttcaacgt ggtatgttca    9000
gcggataata gacctttgac taatttatcg gatagtcttt tgatgtgagc ttggtcgttg    9060
tcaaattctt tcttcatcaa tctcgcagct tcaccaaatc ccgctaccaa tggggggcc     9120
aaagtaccag atctcaatcc tctctcttgg ccaccaccgg atagtaaagg ttctaatcta    9180
actcttggtc tccttcttac atagatggca cctattccct ttggaccgta aatcttgtga    9240
gaagaaattg atagtaaatc aatgttcatt tcattgacat caatgtgaat cttaccatag    9300
gcttgtgcgg cgtcagtatg aaagtagatc ttattctttc tacaaattgc accaatttct    9360
ttaataggtt gaatgacacc gatttcatta ttgacagcca tcacagagac gagacaggta    9420
tctggtctaa tggcatcttc caattccttc aaatcgataa gaccttgatc gtccacattt    9480
aggaaagtga cttcaaatcc ctccttcatc atggcccgtg cggcttccaa gacacacttg    9540
tgttccgttc tagtggtgat gatgtgtttc ttagtcttct tataaaatct tgggacaccc    9600
ttaagaacca tattattaga ttcggtcgct cccgaagtga atattatttc cttgggtcg    9660
gcattgatca tctttgctac gtaagctcta gcatttccca cagcagtatt tgtttcccaa    9720
ccgtaagagt gagtgttgga atgaggatta ccataaagtc ccgtataaaa cttcaacatc    9780
gtatccaaaa ccctagggtc tgttggtgta gtggcttgca tgtcaagata tatgggacga    9840
gtaccaaaac ctgtgttttc ttgataagca tggctcattg cagtgctacc agaagctact    9900
acagcatctg gggtggtacc ggatgcactc gcacgggcac tagcctgtgc ctttgcagca    9960
gcctgaatat cggtatgcgt ttccagagag aagttgtcgt ctaacttcac gcctgctgca   10020
gtctcaatga tattcgaata cgctttgagg agatacagcc taatatccga caaactgttt   10080
tacagattta cgatcgtact tgttacccat cattgaattt tgaacatccg aacctgggag   10140
tttccctga aacagatagt atatttgaac ctgtataata atatatagtc tagcgcttta    10200
cggaagacaa tgtatgtatt tcggttcctg gagaaactat tgcatctatt gcataggtaa   10260
tcttgcacgt cgcatccccg gttcatttc tgcgtttcca tcttgcactt caatagcata    10320
tctttgttaa cgaagcatct gtgcttcatt ttgtagaaca aaaatgcaac gcgagagcgc   10380
```

-continued

| | |
|---|---|
| taattttca aacaaagaat ctgagctgca tttttacaga acagaaatgc aacgcgaaag | 10440 |
| cgctatttta ccaacgaaga atctgtgctt cattttgta aaacaaaaat gcaacgcgag | 10500 |
| agcgctaatt tttcaaacaa agaatctgag ctgcattttt acagaacaga atgcaacgc | 10560 |
| gagagcgcta ttttaccaac aaagaatcta tacttctttt ttgttctaca aaatgcatc | 10620 |
| ccgagagcgc tattttctta acaaagcatc ttagattact ttttttctcc tttgtgcgct | 10680 |
| ctataatgca gtctcttgat aacttttgc actgtaggtc cgttaaggtt agaagaaggc | 10740 |
| tactttggtg tctattttct cttccataaa aaaagcctga ctccacttcc cgcgtttact | 10800 |
| gattactagc gaagctgcgg gtgcattttt tcaagataaa ggcatcccg attatattct | 10860 |
| ataccgatgt ggattgcgca actttgtga acagaaagtg atagcgttga tgattcttca | 10920 |
| ttggtcagaa aattatgaac ggtttcttct attttgtctc tatatactac gtataggaaa | 10980 |
| tgtttacatt ttcgtattgt tttcgattca ctctatgaat agttcttact acaatttttt | 11040 |
| tgtctaaaga gtaatactag agataaacat aaaaaatgta gaggtcgagt ttagatgcaa | 11100 |
| gttcaaggag cgaaaggtgg atgggtaggt tatataggga tatagcacag agatatatag | 11160 |
| caaagagata cttttgagca atgtttgtgg aagcggtatt cgcaatattt tagtagctcg | 11220 |
| ttacagtccg gtgcgttttt ggttttttga aagtgcgtct tcagagcgct tttggttttc | 11280 |
| aaaagcgctc tgaagttcct atactttcta gagaatagga acttcggaat aggaacttca | 11340 |
| aagcgtttcc gaaaacgagc gcttccgaaa atgcaacgcg agctgcgcac atacagctca | 11400 |
| ctgttcacgt cgcacctata tctgcgtgtt gcctgtatat atatatacat gagaagaacg | 11460 |
| gcatagtgcg tgtttatgct taaatgcgta cttatatgcg tctatttatg taggatgaaa | 11520 |
| ggtagtctag tacctcctgt gatattatcc cattccatgc ggggtatcgt atgcttcctt | 11580 |
| cagcactacc ctttagctgt tctatatgct gccactcctc aattggatta gtctcatcct | 11640 |
| tcaatgctat catttccttt gatattcgat cctaggcata gtaccgagaa actagtgcga | 11700 |
| agtagtgatc aggtattgct gttatctgat gagtatacgt tgtcctggcc acggcagaag | 11760 |
| cacgcttatc gctccaattt cccacaacat tagtcaactc cgttaggccc ttcattgaaa | 11820 |
| gaaatgaggt catcaaatgt cttccaatgt gagattttgg gccatttttt atagcaaaga | 11880 |
| ttgaataagg cgcattttc ttcaaagctt tattgtacga tctgactaag ttatcttta | 11940 |
| ataattggta ttcctgttta ttgcttgaag aattgccggt cctatttact cgttttagga | 12000 |
| ctggttca | 12008 |

<210> SEQ ID NO 28
<211> LENGTH: 13654
<212> TYPE: DNA
<213> ORGANISM: Saccharomyces cerevisiae

<400> SEQUENCE: 28

| | |
|---|---|
| gaattctcat gtttgacagc ttatcatcga taagctttaa tgcggtagtt tatcacagtt | 60 |
| aaattgctaa cgcagtcagg caccgtgtat gaaatctaac aatgcgctca tcgtcatcct | 120 |
| cggcaccgtc accctggatg ctgtaggcat aggcttggtt atgccggtac tgccgggcct | 180 |
| cttgcgggat atcgtccatt ccgacagcat cgccagtcac tatggcgtgc tgctagcgct | 240 |
| atatgcgttg atgcaatttc tatgcgcacc cgttctcgga gcactgtccg accgctttgg | 300 |
| ccgccgccca gtcctgctcg cttcgctact tggagccact atcgactacg cgatcatggc | 360 |
| gaccacaccc gtcctgtgga tcaagcggcc gcagtacgta atgcggtatc gtgaaagcga | 420 |
| aaaaaaaact aacagtagat aagacagata gacagataga gatggacgag aaacaggggg | 480 |

```
ggagaaaagg ggaaaagaga aggaaagaaa gactcatcta tcgcagataa gacaatcaac    540
cctcatggcg cctccaacca ccatccgcac tagggaccaa gcgctcgcac cgttagcaac    600
gcttgactca caaccaact gccggctgaa agagcttgtg caatgggagt gccaattcaa     660
aggagccgaa tacgtctgct cgccttttaa gaggcttttt gaacactgca ttgcacccga    720
caaatcagcc actaactacg aggtcacgga cacatatacc aatagttaaa aattacatat    780
actctatata gcacagtagt gtgataaata aaaaattttg ccaagacttt tttaaactgc    840
acccgacaga tcaggtctgt gcctactatg cacttatgcc cggggtcccg ggaggagaaa    900
aaacgagggc tgggaaatgt ccgtggactt taaacgctcc gggttagcag agtagcaggg    960
ctttcggctt tggaaattta ggtgacttgt tgaaaaagca aaatttgggc tcagtaatgc   1020
cactgcagtg gcttatcacg ccaggactgc gggagtggcg ggggcaaaca cacccgcgat   1080
aaagagcgcg atgaatataa aaggggccca atgttacgtc ccgttatatt ggagttcttc   1140
ccatacaaac ttaagagtcc aattagcttc atcgccaata aaaaaacaag ctaaacctaa   1200
ttctaacaag cacatatgga agacgccaaa aacataaaga aaggcccggc gccattctat   1260
ccgctggaag atggaaccgc tggagagcaa ctgcataagg ctatgaagag atacgccctg   1320
gttcctggaa caattgcttt tacagatgca catatcgagg tggacatcac ttacgctgag   1380
tacttcgaaa tgtccgttcg gttggcagaa gctatgaaac gatatgggct gaatacaaat   1440
cacagaatcg tcgtatgcag tgaaaactct cttcaattct ttatgccggt gttgggcgcg   1500
ttatttatcg gagttgcagt tgcgcccgcg aacgacattt ataatgaacg tgaattgctc   1560
aacagtatgg gcatttcgca gcctaccgtg gtgttcgttt ccaaaaaggg gttgcaaaaa   1620
attttgaacg tgcaaaaaaa gctcccaatc atccaaaaaa ttattatcat ggattctaaa   1680
acggattacc agggatttca gtcgatgtac acgttcgtca catctcatct acctcccggt   1740
tttaatgaat acgattttgt gccagagtcc ttcgatagggg acaagacaat tgcactgatc   1800
atgaactcct ctggatctac tggtctgcct aaaggtgtcg ctctgcctca tagaactgcc   1860
tgcgtgagat tctcgcatgc cagagatcct atttttggca atcaaatcat tccggatact   1920
gcgatttttaa gtgttgttcc attccatcac ggttttggaa tgtttactac actcggatat   1980
ttgatatgtg gatttcgagt cgtcttaatg tatagatttg aagaagagct gtttctgagg   2040
agccttcagg attacaagat tcaaagtgcg ctgctggtgc caaccctatt ctccttcttc   2100
gccaaaagca ctctgattga caaatacgat ttatctaatt tacacgaaat tgcttctggt   2160
ggcgctcccc tctctaagga agtcggggaa gcggttgcca agaggttcca tctgccaggt   2220
atcaggcaag gatatgggct cactgagact acatcagcta ttctgattac acccgagggg   2280
gatgataaac cgggcgcggt cggtaaagtt gttccatttt ttgaagcgaa ggttgtggat   2340
ctggataccg ggaaaacgct gggcgttaat caaagaggcg aactgtgtgt gagaggtcct   2400
atgattatgt ccggttatgt aaacaatccg gaagcgacca acgccttgat tgacaaggat   2460
ggatggctac attctggaga catagcttac tgggacgaag cgaacacttt cttcatcgtt   2520
gaccgcctga agtctctgat taagtacaaa ggctatcagg tggctcccgc tgaattggaa   2580
tccatcttgc tccaacaccc caacatcttc gacgcaggtg tcgcaggtct ccccgacgat   2640
gacgccggtg aacttcccgc cgccgttgtt gttttggagc acggaaagac gatgacggaa   2700
aaagagatcg tggattacgt cgccagtcaa gtaacaaccg cgaaaaagtt gcgcggagga   2760
gttgtgtttg tggacgaagt accgaaaggt cttaccggaa aactcgacgc aagaaaaatc   2820
```

-continued

```
agagagatcc tcataaaggc caagaagggc ggaaagatcg ccgtgtaatt ggatccagtt   2880
taaacagtag ctttggactt cttcgccaga ggtttggtca agtctccaat caaggttgtc   2940
ggcttgtcta ccttgccaga aatttacgaa agatggaaaa agggtcaaat cgttggtaga   3000
tacgttgttg acacttctaa ataagcgaat ttcttatgat ttatgatttt tattattaaa   3060
taagttataa aaaaaataag tgtatacaaa ttttaaagtg actcttaggt tttaaaacga   3120
aaattcttgt tcttgagtaa ctcttttcctg taggtcaggt tgctttctca ggtatagcat   3180
gaggtcgctc ttattgacca cacctctacc ggcatgccga gcaaatgcct gcaaatcgct   3240
ccccatttca cccaattgta gatatgctaa ctccagcaat gagttgatga atctcggtgt   3300
gtattttatg tcctcagaag acaacacctg ttgtaatcgt tcttccacac ggatcgcggc   3360
cgcttgatcc tctacgccgg acgcatcgtg gccggcatca ccggcgccac aggtgcggtt   3420
gctggcgcct atatcgccga catcaccgat ggggaagatc gggctcgcca cttcgggctc   3480
atgagcgctt gtttcggcgt gggtatggtg gcaggccccg tggccggggg actgttgggc   3540
gccatctcct tgcatgcacc attccttgcg gcggcggtgc tcaacggcct caacctacta   3600
ctgggctgct tcctaatgca ggagtcgcat aagggagagc gtcgaccgat gcccttgaga   3660
gccttcaacc cagtcagctc cttccggtgg gcgcggggca tgactatcgt cgccgcactt   3720
atgactgtct tctttatcat gcaactcgta ggacaggtgc cggcagcgct ctgggtcatt   3780
ttcggcgagg accgctttcg ctggagcgcg acgatgatcg gcctgtcgct tgcggtattc   3840
ggaatcttgc acgccctcgc tcaagccttc gtcactggtc ccgccaccaa cgtttcggc    3900 gagaagcagg ccattatcgc cggcatggcg gccgacgcgc tgggctacgt cttgctggcg   3960
ttcgcgacgc gaggctggat ggccttcccc attatgattc ttctcgcttc cggcggcatc   4020
gggatgcccg cgttgcaggc catgctgtcc aggcaggtag atgacgacca tcagggacag   4080
cttcaaggat cgctcgcggc tcttaccagc ctaacttcga tcactggacc gctgatcgtc   4140
acggcgattt atgccgcctc ggcgagcaca tggaacgggt tggcatggat tgtaggcgcc   4200
gccctatacc ttgtctgcct cccgcgttg cgtcgcggtg catggagccg gccacctcg     4260 acctgaatgg aagccggcgg cacctcgcta acggattcac cactccaaga attggagcca   4320
atcaattctt gcggagaact gtgaatgcgc aaaccaaccc ttggcagaac atatccatcg   4380
cgtccgccat ctccagcagc cgcacgcggc gcatctcggg cagcgttggg tcctggccac   4440
gggtgcgcat gatcgtgctc ctgtcgttga ggacccggct aggctggcgg ggttgccta   4500 ctggttagca gaatgaatca ccgatacgcg agcgaacgtg aagcgactgc tgctgcaaaa   4560
cgtctgcgac ctgagcaaca acatgaatgg tcttcggttt ccgtgtttcg taaagtctgg   4620
aaacgcggaa gtcagcgccc tgcaccatta tgttccggat ctgcatcgca ggatgctgct   4680
ggctaccctg tggaacacct acatctgtat taacgaagcg ctggcattga ccctgagtga   4740 ttttttctctg gtcccgccgc atccataccg ccagttgttt accctcacaa cgttccagta   4800
accgggcatg ttcatcatca gtaacccgta tcgtgagcat cctctctcgt ttcatcggta   4860
tcattacccc catgaacaga aattcccct tacacggagg catcaagtga ccaaacagga    4920 aaaaccgcc cttaacatgg cccgctttat cagaagccag acattaacgc ttctggagaa    4980
actcaacgag ctggacgcgg atgaacaggc agacatctgt gaatcgcttc acgaccacgc   5040
tgatgagctt taccgcagct gcctcgcgcg tttcggtgat gacggtgaaa acctctgaca   5100
catgcagctc ccggagacgg tcacagcttg tctgtaagcg gatgccggga gcagacaagc   5160
ccgtcagggc gcgtcagcgg gtgttggcgg gtgtcggggc gcagccatga cccagtcacg   5220
```

```
tagcgatagc ggagtgtata ctggcttaac tatgcggcat cagagcagat tgtactgaga    5280
gtgcacgata tccggtgtga aataccgcac agatgcgtaa ggagaaaata ccgcatcagg    5340
cgctcttccg cttcctcgct cactgactcg ctgcgctcgg tcgttcggct gcggcgagcg    5400
gtatcagctc actcaaaggc ggtaatacgg ttatccacag aatcagggga taacgcagga    5460
aagaacatgt gagcaaaagg ccagcaaaag gccaggaacc gtaaaaaggc cgcgttgctg    5520
gcgtttttcc ataggctccg ccccctgac gagcatcaca aaaatcgacg ctcaagtcag    5580
aggtggcgaa acccgacagg actataaaga taccaggcgt ttccccctgg aagctccctc    5640
gtgcgctctc ctgttccgac cctgccgctt accggatacc tgtccgcctt tctcccttcg    5700
ggaagcgtgg cgctttctca atgctcacgc tgtaggtatc tcagttcggt gtaggtcgtt    5760
cgctccaagc tgggctgtgt gcacgaaccc cccgttcagc ccgaccgctg cgccttatcc    5820
ggtaactatc gtcttgagtc aacccggta agacacgact tatcgccact ggcagcagcc    5880
actggtaaca ggattagcag agcgaggtat gtaggcggtg ctacagagtt cttgaagtgg    5940
tggcctaact acggctacac tagaaggaca gtatttggta tctgcgctct gctgaagcca    6000
gttaccttcg gaaaaagagt tggtagctct tgatccggca acaaaccac cgctggtagc    6060 ggtggttttt ttgtttgcaa gcagcagatt acgcgcagaa aaaaggatc tcaagaagat    6120 cctttgatct tttctacggg gtctgacgct cagtggaacg aaaactcacg ttaagggatt    6180
ttggtcatga gattatcaaa aaggatcttc acctagatcc ttttaaatta aaaatgaagt    6240
tttaaatcaa tctaaagtat atatgagtaa acttggtctg acagttacca atgcttaatc    6300
agtgaggcac ctatctcagc gatctgtcta tttcgttcat ccatagttgc ctgactcccc    6360
gtcgtgtaga taactacgat acgggagggc ttaccatctg gccccagtgc tgcaatgata    6420
ccgcgagacc cacgctcacc ggctccagat ttatcagcaa taaaccagcc agccggaagg    6480
gccgagcgca gaagtggtcc tgcaacttta tccgcctcca tccagtctat taattgttgc    6540
cgggaagcta gagtaagtag ttcgccagtt aatagtttgc gcaacgttgt tgccattgct    6600
gcaggcatcg tggtgtcacg ctcgtcgttt ggtatggctt cattcagctc cggttcccaa    6660
cgatcaaggc gagttacatg atcccccatg ttgtgcaaaa aagcggttag ctccttcggt    6720
cctccgatcg ttgtcagaag taagttggcc gcagtgttat cactcatggt tatggcagca    6780
ctgcataatt ctcttactgt catgccatcc gtaagatgct tttctgtgac tggtgagtac    6840
tcaaccaagt cattctgaga atagtgtatg cggcgaccga gttgctcttg cccggcgtca    6900
acacgggata ataccgcgcc acatagcaga actttaaaag tgctcatcat tggaaaacgt    6960
tcttcggggc gaaaactctc aaggatctta ccgctgttga gatccagttc gatgtaaccc    7020
actcgtgcac ccaactgatc ttcagcatct tttactttca ccagcgtttc tgggtgagca    7080
aaaacaggaa ggcaaaatgc cgcaaaaaag gaataagggc gacacggaa atgttgaata    7140 ctcatactct tcctttttca atattattga agcatttatc agggttattg tctcatgagc    7200
ggatacatat ttgaatgtat ttagaaaaat aaacaaatag gggttccgcg cacatttccc    7260
cgaaaagtgc cacctgacgt ctaagaaacc attattatca tgacattaac ctataaaaat    7320
aggcgtatca cgaggccctt tcgtcttcaa gaattccacg gactatagac tatactagta    7380
tactccgtct actgtacgat acacttccgc tcaggtcctt gtcctttaac gaggccttac    7440
cactcttttg ttactctatt gatccagctc agcaaaggca gtgtgatcta agattctatc    7500
ttcgcgatgt agtaaaacta gctagaccga gaaagagact agaaatgcaa aaggcacttc    7560
```

```
tacaatggct gccatcatta ttatccgatg tgacgctgca gaagcagaaa tacacgcggt      7620
cagtgaagct attccgctat tgaataacct cagtcacctt gtgcaagaac ttaacaagaa      7680
accaattatt aaaggcttac ttactgatag tagatcaacg atcagtataa ttaagtctac      7740
aaatgaagag aaatttagaa acagattttt tggcacaaag gcaatgagac ttagagatga      7800
agtatcaggt aataatttat acgtatacta catcgagacc aagaagaaca ttgctgatgt      7860
gatgacaaaa cctcttccga taaaaacatt taaactatta actaacaaat ggattcatta      7920
gatctattac attatgggtg gtatgttgga ataaaaatca actatcatct actaactagt      7980
atttacgtta ctagtatatt atcatatacg gtgttagaag atgacgcaaa tgatgagaaa      8040
tagtcatcta aattagtgga agctgaaacg caaggattga taatgtaata ggatcaatga      8100
atattaacat ataaaatgat gataataata tttatagaat tgtgtagaat tgcagattcc      8160
cttttatgga ttcctaaatc ctcgaggaga acttctagta tatctacata cctaatatta      8220
ttgccttatt aaaaatggaa tcccaacaat tacatcaaaa tccacattct cttcaaaatc      8280
aattgtcctg tacttccttg ttcatgtgtg ttcaaaaacg ttatatttat aggataatta      8340
tactctattt ctcaacaagt aattggttgt ttggccgagc ggtctaaggc gcctgattca      8400
agaaatatct tgaccgcagt taactgtggg aatactcagg tatcgtaaga tgcaagagtt      8460
cgaatctctt agcaaccatt attttttttcc tcaacataac gagaacacac aggggcgcta      8520
tcgcacagaa tcaaattcga tgactggaaa ttttttgtta atttcagagg tcgcctgacg      8580
catataccct tttcaactga aaaattggga gaaaaggaa aggtgagagc cgcggaaccg      8640
gcttttcata tagaatagag aagcgttcat gactaaatgc ttgcatcaca atacttgaag      8700
ttgacaatat tatttaagga cctattgttt tttccaatag gtggttagca atcgtcttac      8760
tttctaactt ttcttacctt ttacatttca gcaatatata tatatatatt tcaaggatat      8820
accattctaa tgtctgcccc taagaagatc gtcgttttgc caggtgacca cgttggtcaa      8880
gaaatcacag ccgaagccat taaggttctt aaagctattt ctgatgttcg ttccaatgtc      8940
aagttcgatt tcgaaaatca tttaattggt ggtgctgcta tcgatgctac aggtgtccca      9000
cttccagatg aggcgctgga agcctccaag aaggttgatg ccgttttgtt aggtgctgtg      9060
ggtggtccta aatgggggtac cggtagtgtt agacctgaac aaggtttact aaaaatccgt      9120
aaagaacttc aattgtacgc caacttaaga ccatgtaact ttgcatccga ctctctttta      9180
gacttatctc caatcaagcc acaatttgct aaaggtactg acttcgttgt tgtcagagaa      9240
ttagtgggag gtatttactt tggtaagaga aaggaagacg atggtgatgg tgtcgcttgg      9300
gatagtgaac aatacaccgt tccagaagtg caaagaatca caagaatggc cgctttcatg      9360
gccctacaac atgagccacc attgcctatt tggtccttgg ataaagctaa tgtttttggcc      9420 tcttcaagat tatggagaaa aactgtggag gaaaccatca agaacgaatt ccctacattg      9480
aaggttcaac atcaattgat tgattctgcc gccatgatcc tagttaagaa cccaacccac      9540
ctaaatggta ttataatcac cagcaacatg tttggtgata tcatctccga tgaagcctcc      9600
gttatcccag gttccttggg tttgttgcca tctgcgtcct ggcctctttt gccagacaag      9660
aacaccgcat ttggtttgta cgaaccatgc cacggttctg ctccagattt gccaaagaat      9720
aaggtcaacc ctatcgccac tatcttgtct gctgcaatga tgttgaaatt gtcattgaac      9780
ttgcctgaag aaggtaaggc cattgaagat gcagttaaaa aggttttgga tgcaggtatc      9840
agaactggtg atttaggtgg ttccaacagt accacggaag tcggtgatgc tgtcgccgaa      9900
gaagttaaga aaatccttgc ttaaaaagat tctcttttttt tatgatattt gtacataaac      9960
```

```
tttataaatg aaattcataa tagaaacgac acgaaattac aaaatggaat atgttcatag   10020
ggtagacgaa actatatacg caatctacat acatttatca agaaggagaa aaaggaggat   10080
gtaaaggaat acaggtaagc aaattgatac taatggctca acgtgataag gaaaaagaat   10140
tgcactttaa cattaatatt gacaaggagg agggcaccac acaaaaagtt aggtgtaaca   10200
gaaaatcatg aaactatgat tcctaattta tatattggag gattttctct aaaaaaaaaa   10260
aaatacaaca aataaaaaac actcaatgac ctgaccattt gatggagttt aagtcaatac   10320
cttcttgaac catttcccat aatggtgaaa gttccctcaa gaattttact ctgtcagaaa   10380
cggccttaac gacgtagtcg acctcctctt cagtactaaa tctaccaata ccaaatctga   10440
tggaagaatg ggctaatgca tcatccttac ccagcgcatg taaaacataa gaaggttcta   10500
gggaagcaga tgtacaggct gaacccgagg ataatgcgat atcccttagt gccatcaata   10560
aagattctcc ttccacgtag gcgaaagaaa cgttaacaca ccctggataa cgatgatctg   10620
gagatccgtt caacgtggta tgttcagcgg ataatagacc tttgactaat ttatcggata   10680
gtcttttgat gtgagcttgg tcgttgtcaa attctttctt catcaatctc gcagcttcac   10740
caaatcccgc taccaatggg ggggccaaag taccagatct caatcctctc tcttggccac   10800
caccggatag taaaggttct aatctaactc ttggtctcct tcttacatag atggcaccta   10860
ttcccttggg accgtaaatc ttgtgagaag aaattgatag taaatcaatg ttcatttcat   10920
tgacatcaat gtgaatctta ccataggctt gtgcggcgtc agtatgaaag tagatcttat   10980
tctttctaca aattgcacca atttctttaa taggttgaat gacaccgatt tcattattga   11040
cagccatcac agagacgaga caggtatctg gtctaatggc atcttccaat tccttcaaat   11100
cgataagacc ttgatcgtcc acatttagga aagtgacttc aaatccctcc ttcatcatgg   11160
cccgtgcggc ttccaagaca cacttgtgtt ccgttctagt ggtgatgatg tgtttcttag   11220
tcttcttata aaatcttggg acacccttaa gaaccatatt attagattcg gtcgctcccg   11280
aagtgaatat tatttccttg gggtcggcat tgatcatctt tgctacgtaa gctctagcat   11340
tttccacagc agtatttgtt tcccaaccgt aagagtgagt gttggaatga ggattaccat   11400
aaagtcccgt ataaaacttc aacatcgtat ccaaaaccct agggtctgtt ggtgtagtgg   11460
cttgcatgtc aagatatatg ggacgagtac caaaacctgt gttttcttga taagcatggc   11520
tcattgcagt gctaccagaa gctactacag catctggggt ggtaccggat gcactcgcac   11580
gggcactagc ctgtgccttt gcagcagcct gaatatcggt atgcgtttcc agagagaagt   11640
tgtcgtctaa cttcacgcct gctgcagtct caatgatatt cgaatacgct ttgaggagat   11700
acagcctaat atccgacaaa ctgttttaca gatttacgat cgtacttgtt acccatcatt   11760
gaattttgaa catccgaacc tgggagtttt ccctgaaaca gatagtatat ttgaacctgt   11820
ataataatat atagtctagc gctttacgga agacaatgta tgtatttcgg ttcctggaga   11880
aactattgca tctattgcat aggtaatctt gcacgtcgca tccccggttc attttctgcg   11940
tttccatctt gcacttcaat agcatatctt tgttaacgaa gcatctgtgc ttcattttgt   12000
agaacaaaaa tgcaacgcga gagcgctaat ttttcaaaca aagaatctga gctgcatttt   12060
tacagaacag aaatgcaacg cgaaagcgct atttttaccaa cgaagaatct gtgcttcatt   12120
tttgtaaaac aaaaatgcaa cgcgagagcg ctaattttc aaacaaagaa tctgagctgc   12180 attttttacag aacagaaatg caacgcgaga gcgctatttt accaacaaag aatctatact   12240
tcttttttgt tctacaaaaa tgcatcccga gagcgctatt tttctaacaa agcatcttag   12300
```

-continued

```
attactttt  ttctcctttg  tgcgtctat   aatgcagtct  cttgataact  ttttgcactg  12360
taggtccgtt  aaggttagaa  gaaggctact  ttggtgtcta  ttttctcttc  cataaaaaaa  12420
gcctgactcc  acttcccgcg  tttactgatt  actagcgaag  ctgcgggtgc  atttttcaa   12480 gataaaggca  tccccgatta  tattctatac  cgatgtggat  tgcgcatact  ttgtgaacag  12540
aaagtgatag  cgttgatgat  tcttcattgg  tcagaaaatt  atgaacggtt  tcttctattt  12600
tgtctctata  tactacgtat  aggaaatgtt  tacattttcg  tattgttttc  gattcactct  12660
atgaatagtt  cttactacaa  ttttttttgtc  taaagagtaa  tactagagat  aaacataaaa  12720
aatgtagagg  tcgagtttag  atgcaagttc  aaggagcgaa  aggtggatgg  gtaggttata  12780
tagggatata  gcacagagat  atatagcaaa  gagatacttt  tgagcaatgt  ttgtggaagc  12840
ggtattcgca  atattttagt  agctcgttac  agtccggtgc  gtttttggtt  ttttgaaagt  12900
gcgtcttcag  agcgcttttg  gttttcaaaa  gcgctctgaa  gttcctatac  tttctagaga  12960
ataggaactt  cggaatagga  acttcaaagc  gtttccgaaa  acgagcgctt  ccgaaaatgc  13020
aacgcgagct  gcgcacatac  agctcactgt  tcacgtcgca  cctatatctg  cgtgttgcct  13080
gtatatatat  atacatgaga  agaacggcat  agtgcgtgtt  tatgcttaaa  tgcgtactta  13140
tatgcgtcta  tttatgtagg  atgaaaggta  gtctagtacc  tcctgtgata  ttatcccatt  13200
ccatgcgggg  tatcgtatgc  ttccttcagc  actacccttt  agctgttcta  tatgctgcca  13260
ctcctcaatt  ggattagtct  catccttcaa  tgctatcatt  tcctttgata  ttcgatccta  13320
ggcatagtac  cgagaaacta  gtgcgaagta  gtgatcaggt  attgctgtta  tctgatgagt  13380
atacgttgtc  ctggccacgg  cagaagcacg  cttatcgctc  caattttccca  caacattagt  13440 caactccgtt  aggcccttca  ttgaaagaaa  tgaggtcatc  aaatgtcttc  caatgtgaga  13500
ttttgggcca  ttttttatag  caaagattga  ataaggcgca  tttttcttca  aagctttatt  13560
gtacgatctg  actaagttat  cttttaataa  ttggtattcc  tgtttattgc  ttgaagaatt  13620
gccggtccta  tttactcgtt  ttaggactgg  ttca                                13654
```

<210> SEQ ID NO 29
<211> LENGTH: 600
<212> TYPE: DNA
<213> ORGANISM: Saccharomyces cerevisiae

<400> SEQUENCE: 29

```
agaaccaaat  gggaaaatcg  gaatgggtcc  agaactgctt  tgagtgctgg  ctattggcgt   60
ctgatttccg  ttttgggaat  cctttgccgc  gcgcccctct  caaaactccg  cacaagtccc  120
agaaagcggg  aaagaaataa  aacgccacca  aaaaaaaaaa  aataaaagcc  aatcctcgaa  180
gcgtgggtgg  taggccctgg  attatcccgt  acaagtattt  ctcaggagta  aaaaaaccgt  240
ttgttttgga  attccccatt  tcgcggccac  ctacgccgct  atctttgcaa  caactatctg  300
cgataactca  gcaaattttg  catattcgtg  ttgcagtatt  gcgataatgg  gagtcttact  360
tccaacataa  cggcagaaag  aaatgtgaga  aaattttgca  tcctttgcct  ccgttcaagt  420
atataaagtc  ggcatgcttg  ataatctttc  tttccatcct  acattgttct  aattattctt  480
attctccttt  attctttcct  aacataccaa  gaaattaatc  ttctgtcatt  cgcttaaaca  540
ctatatcaat  aatgcaattt  tctactgtcg  cttctatcgc  cgctgtcgcc  gctgtcgctt  600
```

<210> SEQ ID NO 30
<211> LENGTH: 850
<212> TYPE: DNA
<213> ORGANISM: Saccharomyces cerevisiae

<400> SEQUENCE: 30

```
gccacgggtc aacccgattg ggatcacccc actggggccc aagcctgata tccgacctcc    60
atgaaatttt ttttttcttt tcgattagca cgcacacaca tcacatagac tgcgtcataa   120
aaatacacta cggaaaaacc ataaagagca aagcgatacc tacttggaag gaaaaggagc   180
acgcttgtaa gggggatggg ggctaagaag tcattcactt tcttttccct tcgcggtccg   240
gacccgggac ccctcctctc cccgcacgat ttcttccttt catatcttcc ttttattcct   300
atcccgttga agcaaccgca ctatgactaa atggtgctgg acatctccat ggctgtgact   360
tgtgtgtatc tcacagtggt aacggcaccg tggctcggaa acggttcctt cgtgacaatt   420
ctagaacagg ggctacagtc tcgataatag aataataagc gcattttgtc tagcgccgcc   480
gcggcgcccg tttcccaata gggaggcgca gtttatcggc ggagctctac ttcttcctat   540
ttgggtaagc ccctttctgt tttcggccag tggttgctgc aggctgcgcc ggagaacata   600
gtgataaggg atgtaacttt cgatgagaga attagcaagc ggaaaaaaac tatggctagc   660
tgggagttgt ttttcaatca tataaaaggg agaaattgtt gctcactatg tgacagtttc   720
tgggacgtct taacttttat tgcagaggac tatcaaatca tacagatatt gtcaaaaaaa   780
aaaaagacta ataataaaaa atgaagttat ctcaagttgt tgtttccgcc gtcgccttca   840
ctggtttagt                                                         850
```

<210> SEQ ID NO 31
<211> LENGTH: 600
<212> TYPE: DNA
<213> ORGANISM: Saccharomyces cerevisiae

<400> SEQUENCE: 31

```
aaagaatcca tcactatttg aaaaaaagtc atctggcacg tttaattatc agagcagaaa    60
tgatgaaggg tgttagcgcc gtccactgat gtgcctggta gtcatgattt acgtataact   120
aacacatcat gaggacggcg gcgtcacccc aacgcaaaag agtgacttcc ctgcgctttg   180
ccaaaacccc atacatcgcc atctggctcc tgcagggcg gttgatggac atcagccgcc   240
tcccttaatt gctaaagcct ccacaaggca caattaagca atatttcggg aaagtacacc   300
agtcagtttg cgcttttatg actgggttct aaggtactag atgtgaagta gtggtgacag   360
aatcagggag ataagaggga gcagggtggg gtaatgatgt gcgataacaa tcttgcttgg   420
ctaatcaccc ccatatcttg tagtgagtat ataaatagga gcctcccttc ctattgcaac   480
tccataaaat ttttttttgt agccacttct gtaacaagat aaataaaacc aactaatcga   540
gatatcaaat atgggtagtt tttgggacgc attcgcagta tacgacaaga aaaagcacgc   600
```

<210> SEQ ID NO 32
<211> LENGTH: 600
<212> TYPE: DNA
<213> ORGANISM: Saccharomyces cerevisiae

<400> SEQUENCE: 32

```
ttcaggagtc tctcgcgtta gagcagtacg tggcgcagct aaactcgccg ggaggtctgc    60
ttcacgagcg cggtgtgcgc ctagtattgc cccgacggtc cgggtgccta tccctagatt   120
tcgtcgtgcc ccgacccaaa tagttaaacg tgtggtttat gggtgcacca gggctttatc   180
gtgttttata tcgatggcga tttgtgcctc cagtgtattt ttgtatatcc aattaaggtt   240
tcttacctaa ttttatttttt atcatcttta gttaatgctg gtttgctctg tttctgctgc   300
```

```
tttctgtgcg gttctcctct tctcttgttt cttcgtgttg tccccatcg ccgatgggct      360 tatatggcgt atatatatag agcgagtttt tacgtcgaag atcatctcag tttgcttgat      420
agcctttcta ctttattact ttcgttttta acctcattat actttagttt tctttgatcg      480
gtttttttct ctgtatactt aaaagttcaa atcaaagaaa catacaaaac tacgtttata      540
tcaattaata atgtctgaaa ttcaaaacaa agctgaaact gccgcccaag atgtccaaca      600
```